United States Patent [19]
Dorsch et al.

[11] Patent Number: 6,017,939
[45] Date of Patent: Jan. 25, 2000

[54] 2,1,3-BENZOTHIA(OXA)DIAZOLE DERIVATIVES HAVING AN ENDOTHELIN RECEPTOR ANTAGONISTIC EFFECT

[75] Inventors: Dieter Dorsch, Ober-Ramstadt; Mathias Osswald, Sqingenberg; Werner Mederski, Erzhausen; Claudia Wilm, Mühltal; Claus Schmitges, Gross-Umstadt; Maria Christadler, Rödermark; Soheila Anzali, Darmstadt, all of Germany

[73] Assignee: Merck Patent Gesellschaft, Darmstadt, Germany

[21] Appl. No.: 09/142,408

[22] PCT Filed: Feb. 20, 1997

[86] PCT No.: PCT/EP97/00818

§ 371 Date: Nov. 12, 1998

§ 102(e) Date: Nov. 12, 1998

[87] PCT Pub. No.: WO97/30982

PCT Pub. Date: Aug. 28, 1997

[30] Foreign Application Priority Data

Feb. 24, 1996 [DE] Germany .................. 196 07 096

[51] Int. Cl.[7] .................. C07D 285/14; A01R 31/91
[52] U.S. Cl. .................. 514/362; 514/364; 548/126
[58] Field of Search .................. 548/126; 514/362, 514/364

[56] References Cited

FOREIGN PATENT DOCUMENTS

| 733626 | 3/1996 | European Pat. Off. . |
|---|---|---|
| 95/05376 | 2/1995 | WIPO . |

*Primary Examiner*—Robert Gerstl
*Attorney, Agent, or Firm*—Millen, White, Zelano & Branigan

[57] ABSTRACT

The invention concerns compounds of formula (I), in which R is (i), (ii) or (iii); n is 0, 1 or 2; X means O or S; and $R^1$, $R^2$, $R^3$ and $R^4$ have different meanings, or a cyclized tautomeric shape. The invention also concerns the (E) isomers and salts of these compounds which display endothelin receptor antagonistic properties.

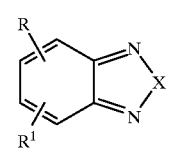

(I)

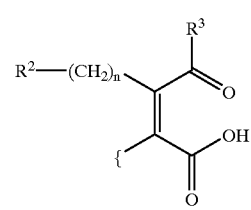

(I)

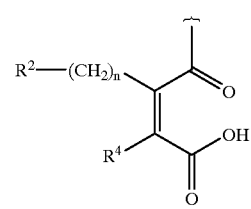

(II)

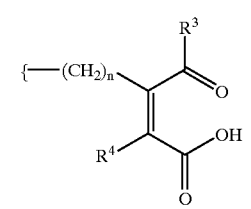

(III)

21 Claims, No Drawings

2,1,3-BENZOTHIA(OXA)DIAZOLE DERIVATIVES HAVING AN ENDOTHELIN RECEPTOR ANTAGONISTIC EFFECT

The invention relates to compounds of the formula I

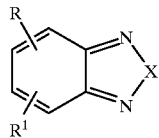

in which

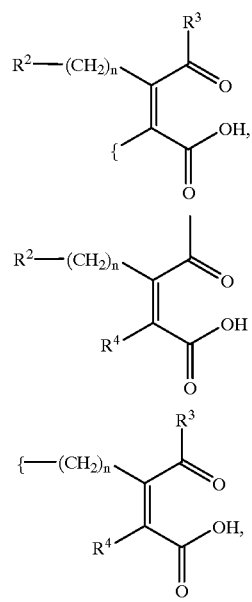

R is or

X is O or S, $R^1$ is H, Hal, OH, OA, A, alkylene-O-A, $NO_2$, $NH_2$, NHacyl, $SO_2NH_2$, $SO_3$-A, $SO_2NHA$, CN or formyl, $R^2$, $R^3$, $R^4$ in each case independently of one another are a phenyl group which is unsubstituted or mono- or polysubstituted by Hal, OH, OA, O-alkylene-$R^5$, A, S-A, S-OA, $SO_2A$, S-$OR^5$, $SO_2R^5$, $NO_2$, NHA, $NA_2$, NHacyl, $NHSO_2A$, $NHSO_2R^5$, $NASO_2A$, $NASO_2$-$R^5$, $NH(CO)NH_2$, NH(CO)NHA, formyl, $NH(CO)NHR^5$, NHCOOA, NAacyl, $NHCOOCH_2R^5$, $NHSO_2CH_2R^5$, NHCOO-alkylene-OA, $NH(CO)NA_2$, 1-piperidinyl-CO-NH, 1-pyrrolidinyl-CONH, $O(CH_2)_nCOOA$, $O(CH_2)_nCOOH$, $O(CH_2)_nOH$, $O(CH_2)_nOA$, $CH_2OH$, $CH_2OA$, COOH, COOA, $CH_2COOH$ or $CH_2COOA$,

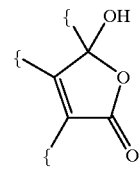

-continued

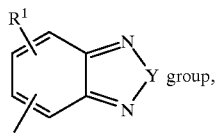

where $R^2$ is additionally A or cycloalkyl, $R^5$ is a phenyl group which is unsubstituted or mono- or polysubstituted by Hal, OH, OA, A, S-A, $NO_2$, $NH_2$, NHA, $NA_2$, NHacyl, $NHSO_2A$, $NASO_2A$, NH(CO)$NH_2$, NH(CO)NHA, formyl, NHCOOA, NAacyl, NHCOO-alkylene-OA, $NH(CO)NA_2$, N-piperidinyl-CO-NH, N-pyrrolidinyl-CONH, $O(CH_2)_nCOOA$, $O(CH_2)_nCOOH$, $O(CH_2)_nO$, $O(CH_2)_nOA$, $CH_2OH$, $CH_2OA$, COOH, COOA, $CH_2COOH$ or $CH_2COOA$, A is alkyl having 1–6 C atoms, in which one or two $CH_2$ groups can be replaced by O or S atoms or by —$CR^6$=$CR^6$ groups and/or 1–7 H atoms can be replaced by F, D is carbonyl or $[C(R^6R^{6'})]_m$, E is $CH_2$, S or O, Y is O or S, $R^6$ and $R^{6'}$ in each case independently of one another are H, F or A, Hal is fluorine, chlorine, bromine or iodine, n is 0, 1 or 2 and m is 1 or 2, or a ta tutomeric ring-closed form, and the (E) isomers and the salts of all isomers.

The tautomeric ring-closed hydroxylactone form

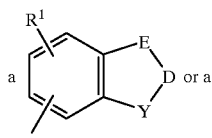

is present if the compounds of the formula I are isolated as carboxylic acids. If the compounds of the formula I are obtained as salts (carboxylates); the open-chain tautomer is obtained.

Similar compounds are disclosed in WO 95/05376.

The invention was based on the object of finding novel compounds having useful properties, in particular those which can be used for the production of medicaments.

It has been found that the compounds of the formula I and their salts have very useful pharmacological properties together with good tolerability. In particular, they show endothelin receptor-antagonistic properties and can therefore be employed for the treatment of diseases such as hypertension, cardiac insufficiency, coronary heart disease, renal, cerebral and myocardial ischaemia, renal insufficiency, cerebral infarct, subarachnoid haemorrhage, arteriosclerosis, pulmonary high blood pressure, infla nmations, asthma, prostate hyperplasia, endotoxic shock and in complications after the administration of substances such as, for example, cyclosporin, as well as other diseases associated with endothelin activities.

The compounds exhibit, inter alia, a high affinity for the endothelin subreceptors $ET_A$ and $ET_B$. These actions can be determined by customary in vitro or in vivo methods, such as described, for example, by P. D. Stein et al., J. Med. Chem. 37, 1994, 329–331 and E. Ohlstein et al., Proc. Natl. Acad. Sci. USA 91, 1994, 8052–8056.

A suitable method for the determination of the hypotensive action is described, for example, by M. K. Bazil et al., J. Cardiovasc. Pharmacol. 22, 1993, 897–905 and J. Lange et al., Lab Animal 20, 1991, Appl. Note 1016.

The compounds of the formula I can be employed as pharmaceutical active compounds in human and veterinary medicine, in particular for the prophylaxis and/or therapy of cardiac, circulatory and vascular diseases, especially of hypertension and cardiac insufficiency.

The invention relates to the compounds of the formula I and their salts, and to a process for the preparation of these compounds and their salts,
in which

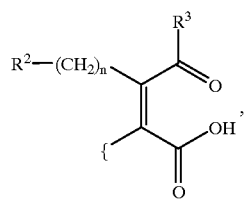

a) R is
characterized in that a compound of the formula II

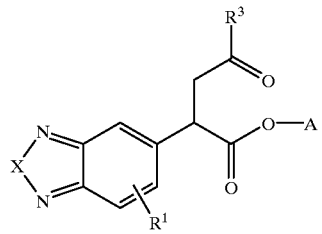

in which
R$^1$, R$^3$ and X have the meaning indicated in claim 1, and A is alkyl having 1–4 C atoms or benzyl,
is reacted with a compound of the formula III
III [sic]

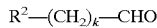

R$^2$—(CH$_2$)$_k$—CHO　　　　III in which
R$^2$ has the meaning indicated in claim 1 and
k is 0 or 1,
and then the ester is cleaved,
or in that, for the preparation of compounds of the formula I according to claim 1 and their salts,
in which

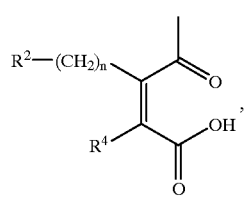

b) R is
a compound of the formula IV

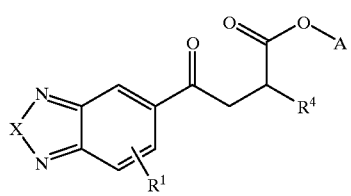

in which
R$^1$, R$^4$ and X have the meaning indicated in claim 1, and A is alkyl having 1–4 C atoms or benzyl,
is reacted with a compound of the formula III, as indicated,
and then the ester is cleaved,
or in that, for the preparation of compounds of the formula I according to claim 1, and their salts,
in which

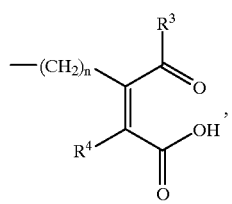

c) R is
a compound of the formula V

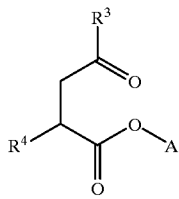

in which
R$^3$ and R$^4$ have the meaning indicated in claim 1, and A is alkyl having 1–4 C atoms or benzyl,
is reacted with a compound of the formula VI,

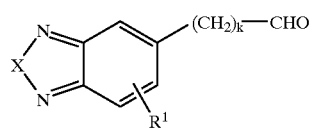

in which
R$^1$ and X have the meanings indicated in claim 1, and k is 0 or 1,
and then the ester is cleaved,
and/or in that, in a compound of the formula I, one or more radicals R$^1$, R$^2$, R$^3$ and/or R$^4$ are converted into one or more radicals R$^1$, R$^2$, R$^3$ and/or R$^4$,
by, for example,
　i) reducing a nitro group to an amino group,
　ii) acylating or alkylating an amino group, iii) converting an amino group into a sulfonamido group, and/or converting a base or acid of the formula I into one of its salts.

For all radicals which occur several times, such as, for example, $R^3$, $R^4$, or $R^5$, it holds that their meanings are independent of one another.

For X and Y, it likewise holds that their meanings are independent of one another.

Above and be lo w, the radicals or parameters R, X, $R^1$, $R^2$, $R^3$, $R^4$, A, k and n have the meanings indicated for the formulae I to VI, if not expressly stated otherwise.

In the above formulae, A is alkyl and has 1 to 6, preferably 1, 2, 3 or 4 C atoms. A is preferably methyl, furthermore ethyl, propyl, isopropyl, butyl, isobutyl, sec-butyl or tert-butyl, and further also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or , 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore trifluoromethyl, pentafluoroethyl, allyl or crotyl.

Cycloalkyl is preferably cyclopropyl, cyclobutyl, cyclopentyl or cyclohexyl.

Alkylene is preferably methylene, ethylene, propylene, butylene and further pentylene or hexylene.

Acyl is preferably formyl, acetyl, propionyl and further also butyryl, pentanoyl or hexanoyl.

E is preferably O, and further also $CH_2$ or S.

D is preferably $CH_2$, but carbonyl is also preferred.

Hal is preferably F, Cl or Br, but also I.

$R^1$ is preferably H, fluorine, chlorine, bromine, iodine, methoxy, ethoxy, propoxy, methoxymethyl, nitro, amino, formamido, acetamido, sulfonamido, methylsulfonamido, N-methylsulfonamido, cyano and further also formyl.

$R^2$, $R^3$ and $R^4$ are in each case independently of one another unsubstituted phenyl, or phenyl which is preferably monosubstituted by fluorine, chlorine, bromine, iodine, hydroxyl, methoxy, ethoxy, propoxy, butoxy, pentyloxy, hexyloxy, benzyloxy, phenethyloxy, methylthio, ethylthio, methylsulfinyl, ethylsulfinyl, methylsulfonyl, ethylsulfonyl, phenylsulfinyl, phenylsulfonyl, nitro, amino, methylamino, ethylamino, dimethylanino, diethylamino, formamido, acetamido, N-methylacetamido, N-ethylacetamido, N-propylacetamido, N-butylacetamido, propionylamino, butyrylamino, methylsulfonamido, ethylsulfonamido, propylsulfonamido, butylsulfonamido, N-methyl-methylsulfonamido, N-methylethylsulfonamido, N-ethyl-methylsulfonamido, N-ethylethylsulfonamido, N-propyl-methylsulfonamido, N-propylethylsulfonamido, N-butyl-methylsulfonmido, N-butylethylsulfonamido, phenylsulfonamido, (4-methylphenyl)-sulfonamido, ureido, methylureido, phenylureido, methoxycarbonylamino, ethoxycarbonylamino, formyl, hydroxmethyl, methoxymethyl, ethoxymethyl, anilino, phenoxycarbonylamino, benzyloxycarbonylamino, benzylsulfonamido, N,N-dimethylureido, 1-piperidinyl-CONH—, 1-pyrrolidinyl-CONH, hydroxyethoxycarbonylamino, methoxyethoxycarbonylamino, carboxymethoxy, carboxyethoxy, methoxycarbonylmethoxy, methoxycarbonylethoxy, hydroxyethoxy, methoxyethoxy, carboxyl-, methoxycarbonyl, ethoxycarbonyl, carboxymethyl, methoxycarbonylmethyl or ethoxycarbonylmethyl, where $R^2$ is further preferably A or cycloalkyl.

$R^2$, $R^3$ and $R^4$ are preferably o-, m- or p-tolyl, o, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-acetamidophenyl, o-, m- or p-methoxyphenyl, o-, m- or p-ethoxyphenyl, o-, m- or p-(N,N-dimethylamino)-phenyl, o-, m- or p- (N-ethyla mino)phenyl, o-, m- or p-(N,N-diethylamino)phenyl, o-, m- or p-fluorophenyl, o-, m- or p-bromophenyl, o-, m- or p-chlorophenyl, o-; m- or p-formylphenyl, o-, m- or p-(phenylsulfonamido)-phenyl, o-, m- or p-(methylsulfonamido)phenyl, o-, m- or p-methylthiophenyl, o-, m- or p-benzyloxyphenyl, o-, m- or p-ureidophenyl, o-, m- or p-(N-methylureido)-phenyl, phenyl, o-, m- or p- (hydroxymethyl)phenyl, o-, m- or p-(methoxymethyl)phenyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobezofuran-5- or -6-yl, 2,3-(2-oxomethylenedioxy)phenyl, 2,3-, 2,4-, 2,5-, 2,6-, 3,4- or 3,5-(difluoromethoxy) (carboxymethyloxy) phenyl, 2,3-, 2,4-, 2,5-, 2,6-, 3,4- or 3,5-methoxy (carboxymethyloxy)-phenyl, 2,3-, 2,4-, 2,5-, 2,6-, 3,4- or 3,5-hydroxy(carboxymethyloxy)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 2-amino-3-chloro-, 2-amino-4-chloro-, 2-amino-5-chloro- or 2-amino-6-chlorophenyl, 2-nitro-4-N,N-dim athylamino- or 3-nitro-4-N,N-dimethylaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, or further preferably 2,3-dihydrobenzofuranyl, 2,3-dihydro-2-oxofuranyl, 2,1,3-benzothiadiazol-4- or -5-yl or 2,1,3-benzoxadiazol-5-yl.

$R^5$ is un substituted phenyl, or phenyl which is preferably monosubstituted by fluorine, chlorine, bromine, iodine, hydroxyl, methoxy, ethoxy, propoxy, butoxy, pentyloxy, hexyloxy, mnethylthio, ethylthio, nitro, amino, methylamino, ethylamino, dimethylamino, diethylamino, formamido, aceta mido, N-methylacetamido, N-ethylacetamido, N-propylacetamido, N-butylacetamido, propionylamino, butyrylamino, methylsulfonamido, ethylsulfonamido, propylsulfonamido, butylsulfonamido, N-methyl-methylsulfonamido, N-methyl-ethylsulfonamido, N-ethyl-methylsulfonamido, N-ethyl-ethylsulfonamido, N-propyl-methylsulfonamido, N-propyl-ethylsulfonamido, N-butyl-methylsulfonamido, N-butyl-ethylsulfonamido, ureido, methylureido, phenylureido, methoxycarbonylamino, ethoxycarbonylamino, formyl, hydroxymethyl, methoxymethyl, ethoxymethyl, N,N-dimethylureido, N-piperidinyl-CONH-, N-pyrrolidinyl-CON , hydroxyethoxycarbonylamino, methoxyethoxycarbonylamino, carboxymethoxy, carboxyethoxy, methoxycarbonylmethoxy, methoxycarbonylethoxy, hydroxyethoxy or methoxyethoxy.

$R^5$ is preferably o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o- , m- or p-(N-methylamino)phenyl, o-, m- or p-acetamidophenyl, o-, m- or p-methoxyphenyl, o-, m- or p-ethoxyphenyl, o-, m- or p-(N,N-dimethylamino)-phenyl, o-, m- or p-(N-ethylamino) phenyl, o-, m- or p-(N,N-diethylamino)phenyl, o-, m- or p-fluorophenyl, o-, m- or p-bromophenyl, o-, m- or p-chlorophenyl, o-, m- or p-formylphenyl, o, m- or p-(methylsulfonamido)-phenyl, o-, m- or p-methylthiophenyl, o-, m- or p-ureidophenyl, o-, m- or p-(N-methylureido)phenyl, o-, m- or p-(hydroxymethyl) phenyl, o-, m- or p-(methoxymethyl)phenyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxo-methylenedioxy)phenyl, 2,3-, 2,4-, 2,5-, 2,6-, 3,4- or 3,5-(difluoromethoxy)-(carboxymethyloxy)phenyl, 2,3-, 2,4-, 2,5-, 2,6-, 3,4- or 3,5-methoxy(carboxymethyloxy)phenyl, 2,3-, 2,4-, 2,5-, 2,6-, 3,4- or 3,5-hydroxy (carboxymethyloxy)-phenyl, further preferably 2,3-, 2,4-, 2,5-, 2,6-, 3,4- or 3,5-difluorophenyl, 2.3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, or 2-amino-6-chlorophenyl, 2-nitro-4-N,N-dethylmino- or 3-nitro-4-N,N-dimethylaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 3-chloro-4-acetamidophenyl.

The compounds of the formula I can have one or more chiral centers and therefore occur in various stereoisomeric forms. The formula I includes all these forms.

The Z isomers of the formula I are particularly preferred, i.e. the compounds in which the C═C double bond is present in the radical R in the Z configuration.

Accordingly, the invention relates in particular to those compounds of the formula I in which at least one of the radicals mentioned has one of the preferred meanings indicated above. Some preferred groups o f compounds can be expressed by the following subformulae Ia to Ie, which correspond to the formula I and in which the radicals not described in greater detail have the meaning indicated for formula I, but in which

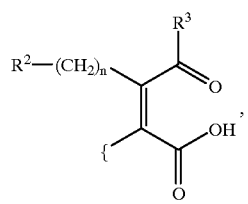

in Ia R is
$R^1$ is H,
X is S and
n is 1;

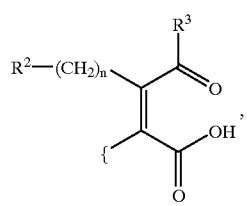

in Ib R is
$R^1$ is H,
X is O and
n is 1;

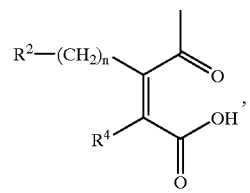

in Ic R is
$R^1$ is H,
X is S and
n is 1;

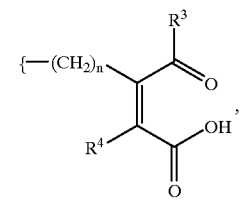

in Id R is
$R^1$ is H,
X is S and
n is 1;

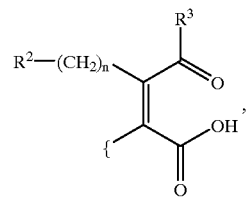

in Ie R is
$R^1$ is H,
$R^2$ and $R^3$ in each case independently of one another are a phenyl group which is unsubstituted or mono- or polysubstituted by Hal, OH, OA, O-alkylene-$R^5$; A, S-A, S-OA, $SO_2A$, S-$OR^5$, $SO_2R^5$, $NO_2$, $NH_2$, NHA, $NA_2$, NHacyl, $NHSO_2A$, $NHSO2R^5$, $NASO_2A$, $NASO_2$-$R^5$, NH(CO)$NH_2$, NH(CO)NHA, formyl, NH(CO)$NHR^5$, NHCOOA, NAacyl, NHCOO$CH_2R^5$, $NHSO_2CH_2R^5$, NHCOO-alkylene-OA, NH(CO)$NA_2$, 1-piperidinyl-CO-NH, 1-pyrrolidinyl-CONH, O$(CH_2)_n$COOA, O$(CH_2)_n$COOH, O$(CH_2)_n$OH, O$(CH_2)_n$OA, $CH_2$OH, $CH_2$OA, COOH, COOA, $CH_2$COOH, $CH_2$COOA, —O—$CH_2$—$CH_2$—O—, —O—$CH_2$—$CH_2$—, —O—$CF_2$—O— or —O—$CF_2$—$CF_2$—O—,

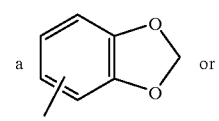

-continued

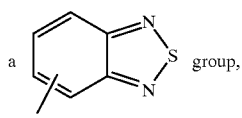 a    group, where $R^2$ is additionally A or cycloalkyl,
X is S and
n is 0, 1 or 2.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. Use can also be made in this case of variants which are known per se, but not mentioned here in greater detail.

If desired, the starting substances can also be formed in situ such that they are not isolated from the reaction mixture, but immediately reacted further to give the compounds of the formula I.

Compounds of the formula I, in which R is

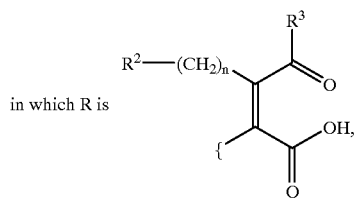

can preferably be obtained by reacting compounds of the fo rula II with compounds of the formula III, and then cleaving the ester.

As a rule, the reaction is carried out in an inert solvent, preferably in the presence of a base. The base used is, for example, a potassium or sodium alkoxide such as potassium or sodium methoxide, ethoxide or tert-butoxide. Preferred solvents are particularly the underlying alcohols.

Depending on the conditions used, the reaction time i s between a few minutes and 14 days, and the reaction temperature between approximately 0° and 150°, normally between 20° and 130°.

Suitable inert solvents are, for example, hydrocarbons such as hexane, petroleum ether, benzene, toluene. or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the solvents mentioned.

As a rule, the starting compounds of the formula II are novel, while as a rule those of the formula III are known. However, the compounds of the formula II can be prepared by methods known per se. Thus, for example, ethyl 2-(2,1,3-benzothiadiazol-5-yl)-4-(4-methoxyphenyl)-4-oxobutanoate can be obtained by reaction of ethyl 2-(2,1,3-benzothia idiazol-5-yl)-acetate with 2'-bromo-4-methoxyacetophenone in an inert solvent with addition of an acid-binding agent, preferably of an alkali metal or alkaline earth metal hydroxide, carbonate or bicarbonate or another salt of a weak acid of the alkali metals or alkaline earth metals, preferably of potassium, sodi im, calcium or caesium. The addition of an organic base such as triethylamine, dimethylaniline, pyridine or quinoline can also be favorable.

Preferably, the reaction is carried out at temperatures between 0° and 150°. Suitable inert solvents are those already mentioned above.

Compounds of the formula I

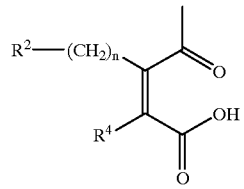

in which R is
can preferably be, obtained by reacting compounds of the formula IV with compounds of the formula III, and then cleaving the ester.

As a rule, the reaction is carried out in an inert solvent, in the presence of an acid-binding agent and at temperatures as indicated above.

As a rule, the starting compounds of the formula IV are novel, but can be prepared by methods known per se:

Thus, for example, by reaction of compounds of the formula VII

VII

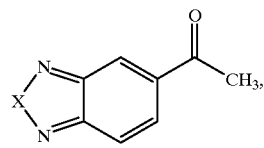

in which X is O or S,
with compounds of the formula VIII $R^4$—CHO                                            VIII, in which $R^4$ has the meaning indicated in claim 1, compounds of the formula IX

IX

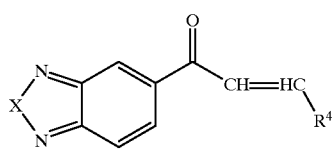

in which X and $R^4$ have the meanings indicated, are obtained.

By subsequent addition of hydrocyanic acid, compounds of the formula X

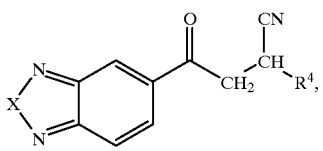

are obtained, which can be converted by subsequent transformation of the nitrile group into a COOH group and subsequent esterification into compounds of the formula IV, in which $R^1$ is H.

Compounds of the formula I, in which R is

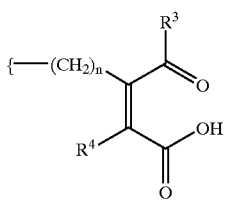

can preferably be obtained by reacting compounds of the formula V with compounds of the formula VI, and then cleaving the ester.

As a rule, the reaction is carried out in an inert solvent, in the presence of an acid-binding agent and at temperatures as indicated above.

Esters can be hydrolysed, for example, using acetic acid or using NaOH or KOH in water, water-THF or water-dioxane at temperatures between 0 and 100°.

As a rule, the starting compounds of the formula V are novel, but can be obtained analogously to the preparation of the compounds of the formula X with subsequent transformation of the nitrile group into an ester function.

As a rule, the starting compounds of the formula VI are known or can be prepared by known methods.

It is further possible to convert a compound of the formula I into another compound of the formula I by converting one or more radicals $R^1$, $R^2$, $R^3$ and/or $R^4$ into one or more radicals $R^1$, $R^2$, $R^3$ and/or $R^4$, e.g. by reducing f litro groups (for example by hydrogenation on Raney nickel or Pd-carbon in an inert solvent such as methanol or ethanol) to amino groups.

Free amino groups can further be acylated in a customary manner using an acid chloride or anhydride or alkylated using an unsubstituted or substituted alkyl halide, expediently in an inert solvent such as dichloromethane or THF and/or in the presence of a base such as triethylamine or pyridine at temperatures between −60 and +30°.

If desired, a functionally modified amino and/or hydroxyl group in a compound of the formula I can be liberated by solvolysis or hydrogenolysis according to customary methods. Thus, for example, a compound of the formula I which contains an NH-acyl or a COOA group can be converted into the corresponding compound of the formula I which, instead of this, contains an $NH_2$ or an HOOC group.

A base of the formula I can be converted into the associated acid addition salt using an acid, for example by reaction of equivalent amounts of the base and of the acid in an inert solvent such as ethanol and subsequent evaporation. Suitable acids for this reaction are particularly those which give physiologically acceptable salts. Thus inorganic acids can be used, e.g. sulfuric acid, nitric acid, hydrohalic acids such as, hydrochloric acid or hydrobromic acid, phosphoric acids such as orthophosphoric acid, sulfamic acid, further organic acids, in particular aliphatic, alicyclic, araliphatic, aromatic or heterocyclic mono- or polybasic carboxylic, sulfonic or sulfuric acids, e.g. formic acid. acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids and laurylsulfuric acid. Salts with physiologically unacceptable acids, e.g. picrates, can be used for the isolation and/or purification of the compounds of the formula I.

On the other hand, compounds of the formula I can be converted using bases (e.g. sodium or potassium hydroxide or carbonate) into the corresponding metal salts, in particular alkali metal salts or alkaline earth metal salts, or into the corresponding ammonium salts.

The invention further relates to the use of the compounds of the formula I and/or their physiologically acceptable salts for the production of pharmaceutical preparations, in particular by a non-chemical route. In this connection, they can be brought into a suitable dose form together with at least one solid, liquid and/or semiliquid excipient or auxiliary and, if appropriate, in combination with one or more further active compounds.

The invention further relates to pharmaceutical preparations, comprising at least one compound of the formula I and/or of one [sic] of its physiologically acceptable salts.

These preparations can be used as medicaments in human or veterinary medicine. Possible excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatine, carbohydrates such as lactose or starch, magnesium stearate, talc, petroleum jelly. In particular, tablets, pills, coated tablets, capsules, powders, granules, syrups, juices or drops are used for oral administration, suppositories for rectal administration, solutions, preferably oily or aqueous solutions, further suspensions, emulsions or implants for parenteral administration and ointments, creams or powders for topical application. The novel compounds can also be lyophilized and the lyophilizates obtained used, for example, for the production of injection preparations. The preparations indicated can be sterilized and/or contain auxiliaries such as lubricants, preservatives, stabilizers and/or wetting agents, emulsifiers, salts for affecting the osmotic pressure, buffer substances, colourants, flavourings and/or [lacuna] more further active compounds, e.g. one or more vitamins.

The compounds of the formula I and their physiologically acceptable salts can be used in the control of diseases, in particular of hypertension and cardiac insufficiency.

In this case, as a rule the substances according to the invention are preferably administered in doses of between approximately 1 and 500 mg, in particular between 5 and 100 mg per dose unit The daily dose is preferably between approximately 0.02 and 10 mg/kg of body weight. However, the specific dose for each patient depends on all sorts of factors, for example on the activity of the specific compound employed, on the age, body weight, general state of health, sex, on the diets on the time and route of administration, on the excretion rate, pharmaceutical substance combination and severity of the particular disorder to which the therapy relates. Oral administration is preferred.

Above and below, all the temperatures are indicated in ° C. In the following examples, "customary working up" means: if necessary, water is added, the mixture, is adjusted, if necessary, depending on the constitution of the final product, to a pH of between 2 and 10, extracted with ethyl acetate or dichloromethane, and the organic phase is separated off, dried over sodium sulfate, evaporated and purified by chromatography on silica gel and/or by crystallization. Rf on silica gel; eluant: ethyl acetate/methanol 9:1.

Mass spectrometry (MS); EI (electron impact ionization) M$^+$; FAB (fast atom bombardment).(M+H)$^+$.

EXAMPLE 1

0.38 g of benzaldehyde and 120 g of ethyl 2-(2,1,3-benzothiadiazol-5-yl)-4-(4-methoxyphenyl)-4-oxobutanoate ("A"), m.p. 89°, (obtainable by reaction of 5.5 g of ethyl 2-(2,1,3-benzothiadiazol-5-yl) acetate with 5.5 g of 2'-bromo-4-methoxyacetophenone and 4 g of potassium carbonate in 200 ml of acetone, 18 hours under reflux; ethyl 2-(2,1,3-benzothiadiazol-5-yl) acetate, m.p. 40–41°, is obtained by reaction of 24.3 g of ethyl 3,4-diaminophenyl acetate and 26.9 ml of thionylaniline in 80 ml of toluene, 4 hours under reflux) are added to a solution of 80 mg of sodium in 5 ml of methanol and the mixture is heated under reflux for one hour. After addition of 5 ml of acetic acid, it is heated for a further 16 hours. The solvent is removed and the residue is worked up in the customary manner. 3-(2,1,3-Benzothiadiazol-5-yl)-4-benzyl- 5-hydroxy-5-(4-methoxy-phenyl)-5H-furan-2-one, FAB 431, is obtained.

The following are obtained analogously by reaction of "A"

with 2-methoxybenzaldehyde
   3-(2,1,3-benzothiadiazol-5-yl)-4-(2-methoxybenzyl)-5-hydroxy-5-(4-methoxyphenyl)-5H-furan-2-one, m.p. 131° with 3-methoxybenzaldehyde
   3-(2,1,3-benzothiadiazol-5-yl)-4-(3-methoxybenzyl)-5-hydroxy-5-(4-methoxyphenyl)-5H-furan-2-one, FAB 460 with 4-methoxybenzaldehyde
   3-(2,1,3-benzothiadiazol-5-yl)-4-(4-methoxybenzyl)-5-hydroxy-5-(4-methoxyphenyl)-5H-furan-2-one, m.p. 70° C., and, as a by-product, 2-(2,1,3-benzothiadiazol-5-yl)-3-(4-methoxybenzyl)-4-(4-methoxyphenyl)-4-oxo-2-butenoic acid, m.p. 184° with 3,4-dimethoxybenzaldehyde
   3-(2,1,3-benzothiadiazol-5-yl)-4-(3,4-dimethoxybenzyl)-5-hydroxy-5-(4-methoxyphenyl)-5H-furan-2-one, m.p. 62° with 3,4,5-trimethoxybenzaldehyde
   3-(2,1,3-benzothiadiazol-5-yl)-4-(3,4,5-trimethoxybenzyl)-5-hydroxy-5-(4-methoxyphenyl)-5H-furan-2-one, m.p. 164°, FAB 543 with 3,4-diisopropoxy-5-methoxybenzaldehyde
   3-(2,1,3-benzothiadiazol-5-yl)-4-(3,4-diisopropoxy-5-methoxybenzyl)-5-hydroxy-5-(4-methoxyphenyl)-5H-furan-2-one, m.p. 136° with 3,4,5-triisopropoxybenzaldehyde
   3-(2,1,3-benzothiadiazol-5-yl)-4-(3,4,5-triisopropoxybenzyl)-5-hydroxy-5-(4-methoxyphenyl)-5H-furan-2-one, m.p. 149° with 4-trifluoromethylbenzaldehyde
   3-(2,1,3-benzothiadiazol-5-yl)-4-(4-trifluoromethylbenzyl)-5-hydroxy-5-(4-methoxyphenyl)-5H-furan-2-one, with 4-cyanobenzaldehyde
   3-(2,1,3-benzothiadiazol-5-yl)-4-(4-cyanobenzyl)-5-hydroxy-5-(4-methoxyphenyl)-5H-furan-2-one, with 4-methylbenzaldehyde
   3-(2,1,3-benzothiadiazol-5-yl)-4-(4-methylbenzyl)-5-hydroxy-5-(4-methoxyphenyl )-5H-furan-2-one, m.p. 58° with 3-methyl-4-methoxybenzaldehyde
   3-(2,1,3-benzothiadiazol-5-yl)-4-(3-methyl-4-methoxybenzyl)-5-hydroxy-5-(4-methoxhenyl)-5H-furan-2-one, with 4-tert-butylbenzaldehyde
   3-(2,1,3-benzothiadiazol-5-yl)-4-(4-tert-butylbenzyl)-5-hydroxy-5-(4-methoxyphenyl)-5H-furan-2-one, with (2-methoxycarbonylmethyloxy-4-methoxy)benzaldehyde
   3-(2,1,3-benzothiadiazol-5-yl)-4-[(2-methoxycarbonylmethyloxy-4-methoxy)benzyl]-5-hydroxy-5-(4-methoxyphenyl)-5H-furan-2-one, with (2-carboxymethyloxy-4-methoxy) benzaldehyde
   3-(2,1,3-benzothiadiazol-5-yl)-4-[(2-carboxymethyloxy-4-methoxy)benzyl]-5-hydroxy-5-(4-methoxyphenyl)-5H-furan-2-one, with 4-ethoxycarbonylbenzaldehyde
   3-(2,1,3-benzothiadiazol-5-yl)-4-(4-ethoxycarbonylbenzyl)-5-hydroxy-5-(4-methoxyphenyl)-5H-furan-2-one, with 4-benzyloxybenzaldehyde
   3-(2,1,3-benzothiadiazol-5-yl)-4-(4-benzyloxybenzyl)-5-hydroxy-5-(4-methoxphenyl)-5H-furan-2-one, with 4-dimethylaminobenzaldehyde
   3-(2,1,3-benzothiadiazol-5-yl)-4-(4-dimethylaminobenzyl)-5-hydroxy-5-(4-methoxyphenyl)-5H-furan-2-one, m.p. 70° with 4-nitrobenzaldehyde
   3-(2,1,3-benzothiadiazol-5-yl)-4-(4-nitrobenzyl)-5-hydroxy-5-(4-methoxyphenyl)-5H-furan-2-one, with (1,3-benzodioxol-5-yl)carbaldehyde
   3-(2,1,3-benzothiadiazol-5-yl)-4-[(1,3-benzodioxol-5-yl)methyl]-5-hydroxy-5-(4-methoxyphenyl)-5H-furan-2-one, m.p. 67° with 3-fluoro-4-methoxybenzaldehyde
   3-(2,1,3-benzothiadiazol-5-yl)-4-(3-fluoro-4-methoxybenzyl)-5-hydroxy-5-(4-methoxyphenyl)-5H-furan-2-one, m.p. 66° with 3-(N,N-dimethylamino)benzaldehyde
   3-(2,1,3-benzothiadiazol-5-yl)-4-[3-(N,N-dimethylamino)benzyl]-5-hydroxy-5-(4-methoxyphenyl)-5H-furan-2-one, with cyclohexanecarbaldehyde
   3-(2,1,3-benzothiadiazol-5-yl)-4-cyclohexylmethyl-5-hydroxy-5-(4-methoxyphenyl)-5H-furan-2-one, m.p. 153°, and with cyclopentanecarbaldehyde
   3-(2,1,3-benzothiadiazol-5-yl)-4-cyclopentylmethyl-5-hydroxy-5-(4-methoxyphenyl)-5H-furan-2-one.

The following are obtained analogously by reaction of ethyl 2-(2,1,3-benzothiadiazol-5-yl)-4-(1,4-benzodioxan-6-yl)-4-oxobutanoate with benzaldehyde
   3-(2,1,3-benzothiadiazol-5-yl)-4-benzyl-5-hydroxy-5-(1,4-benzodioxan-6-yl)-5H-furan-2-one, m.p. 98° with 2-methoxybenzaldehyde
   3-(2,1,3-benzothiadiazol-5-yl)-4-(2-methoxybenzyl)-5-hydroxy-5-(1,4-benzodioxan-6-yl)-5H-furan-2-one, with 3-methoxybenzaldehyde
>3-(2,1,3-benzothiadiazol-5-yl)-4-(3-methoxybenzyl)-5-hydroxy-5-(1,4-benzodioxan-6-yl)-5H-furan-2-one, with 4-methoxybenzaldehyde
>3-(2,1,3-benzothiadiazol-5-yl)-4-(4-methoxybenzyl)-5-hydroxy-5-(1,4-benzodioxan-6-yl)-5H-furan-2-one, with 3,4-dimethoxybenzaldehyde
>3-(2,1,3-benzothiadiazol-5-yl)-4-(3,4-dimethoxybenzyl)-5-hydroxy-5-(1,4-benzodioxan-6-yl)-5H-furan-2-one, with 3,4,5-trimethoxybenzaldehyde
>3-(2,1,3-benzothiadiazol-5-yl)-4-(3,4,5-trimethoxybenzyl)-5-hydroxy-5-(1,4-benzodioxan-6-yl)-5H-furan-2-one, m.p. 82° with 3,4-diisopropoxy-5-methoxybenzaldehyde
>3-(2,1,3-benzothiadiazol-5-yl)-4-(3,4-diisopropoxy-5-methoxybenzyl)-5-hydroxy-5-(1,4-benzodioxan-6-yl)-5H-furan-2-one, m.p. 173° with 3,4,5-triisopropoxybenzaldehyde
>3-(2,1,3-benzothiadiazol-5-yl)-4-(3,4,5-triisopropoxybenzyl)-5-hydroxy-5-(1,4-benzodioxan-6-yl)-5H-furan-2-one, with 4-trifluoromethylbenzaldehyde
>3-(2,1,3-benzothiadiazol-5-yl)-4-(4-trifluoromethylbenzyl)-5-hydroxy-5-(1,4-benzodioxan-6-yl)-5H-furan-2-one, with 4-cyanobenzaldehyde
>3-(2,1,3-benzothiadiazol-5-yl)-4-(4-cyanobenzyl)-5-hydroxy-5-(1,4-benzodioxan-6-yl)-5H-furan-2-one, with 4-methylbenzaldehyde
>3-(2,1,3-benzothiadiazol-5-yl)-4-(4-methylbenzyl)-5-hydroxy-5-(1,4-benzodioxan-6-yl)-5H-furan-2-one, with 3-methyl-4-methoxybenzaldehyde
>3-(2,1,3-benzothiadiazol-5-yl)-4-(3-methyl-4-methoxybenzyl)-5-hydroxy-5-(1,4-benzodioxan-6-yl)-5H-furan-2-one, with 4-tert-butylbenzaldehyde
>3-(2,1,3-benzothiadiazol-5-yl)-4-(4-tertbutylbenzyl)-5-hydroxy-5-(1,4-benzadioxan-6-yl)-5H-furan-2-one, with (2-methoxycarbonylmethyloxy-4-methoxy)benzaldehyde
>3-(2,1,3-benzothiadiazol-5-yl)-4-[(2-methoxycarbonylmethyloxy-4-methoxy)benzyl]-5-hydroxy-5-(1,4-benzodioxan-6-yl)-5H-furan-2-one, with (2-carboxymethyloxy-4-methoxy)benzaldehyde
>3-(2,1,3-benzothiadiazol-5-yl)-4-[(2-carboxymethyloxy-4-methoxy)benzyl]-5-hydroxy-5-(1,4-benzodioxan-6-yl)-5H-furan-2-one, with 4-ethoxycarbonylbenzaldehyde
>3-(2,1,3-benzothiadiazol-5-yl)-4-(4-ethoxycarbonylbenzyl)-5-hydroxy-5-(1,4-benzodioxan-6-yl)-5H-furan-2-one, with 4-benzyloxybenzaldehyde
>3-(2,1,3-benzothiadiazol-5-yl)-4-(4-benzyloxybenzyl)-5-hydroxy-5-(1,4-benzodioxan-6-yl)-5H-furan-2-one, with 4-dimethylaminobenzaldehyde
>3-(2,1,3-benzothiadiazol-5-yl)-4-(4-dimethylaminobenzyl)-5-hydroxy-5-(1,4-benzodioxan-6-yl)-5H-furan-2-one, with 4-nitrobenzaldehyde
>3-(2,1,3-benzothiadiazol-5-yl)-4-(4-nitrobenzyl)-5-hydroxy-5-(1,4-benzodioxan-6-yl)-5H-furan-2-one, with (1,3-benzodioxol-5-yl)carbaldehyde
>3-(2,1,3-benzothiadiazol-5-yl)-4-[(1,3-benzodioxol-5-yl)methyl]-5-hydroxy-5-(1,4-benzodioxan-6-yl)-5H-furan-2-one, with 3-fluoro-4-methoxybenzaldehyde
>3-(2,1,3-benzothiadiazol-5-yl)-4-(3-fluoro-4-methoxybenzyl)-5-hydroxy-5-(1,4-benzodioxan-6-yl)-5H-furan-2-one, with 3-(N,N-dimethylamino)benzaldehyde
>3-(2,1,3-benzothiadiazol-5-yl)-4-[3-(N,N-dimethylamino)benzyl]-5-hydroxy-5-(1,4-benzodioxan-6-yl)-5H-furan-2-one, with cyclohexanecarbaldehyde
>3-(2,1,3-benzothiadiazol-5-yl)-4-cyclohexylmethyl-5-hydroxy-5-(1,4-benzodioxan-6-yl)-5H-furan-2-one, m.p. 81°, and with cyclopentanecarbaldehyde
>3-(2,1,3-benzothiadiazol-5-yl)-4-cyclopentylmethyl-5-hydroxy-5-(1,4-benzodioxan-6-yl)-5H-furan-2-one.

The following are obtained analogously by reaction of ethyl 2-(2,1,3-benzothiadiazol-5-yl)-4-(4-methylphenyl)-4-oxobutanoate with benzaldehyde
>3-(2,1,3-benzothiadiazol-5-yl)-4-benzyl-5-hydroxy-5-(4-methylphenyl)-5H-furan-2-one, with 2-methoxybenzaldehyde
>3-(2,1,3-benzothiadiazol-5-yl)-4-(2-methoxybenzyl)-5-hydroxy-5-(4-methylphenyl)-5H-furan-2-one, with 3-methoxybenzaldehyde
>3-(2,1,3-benzothiadiazol-5-yl)-4-(3-methoxybenzyl)-5-hydroxy-5-(4-methylphenyl)-5H-furan-2-one, with 4-methoxybenzaldehyde
>3-(2,1,3-benzothiadiazol-5-yl)-4-(4-methoxybenzyl)-5-hydroxy-5-(4-methylphenyl)-5H-furan-2-one, with 3,4-dimethoxybenzaldehyde
>3-(2,1,3-benzothiadiazol-5-yl)-4-(3,4-dimethoxybenzyl)-5-hydroxy-5-(4-methylphenyl)-5H-furan-2-one, with 3,4,5-trimethoxybenzaldehyde
>3-(2,1,3-benzothiadiazol-5-yl)-4-(3,4,5-trimethoxybenzyl)-5-hydroxy-5-(4-methylphenyl)-5H-furan-2-one, with 3,4-diisopropoxy-5-methoxybenzaldehyde
>3-(2,1,3-benzothiadiazol-5-yl)-4-(3,4-diisopropoxy-5-methoxybenzyl)-5-hydroxy-5-(4-methylphenyl)-5H-furan-2-one, with 3,4,5-triisopropoxybenzaldehyde
>3-(2,1,3-benzothiadiazol-5-yl)-4-(3,4,5-triisopropoxybenzyl)-5-hydroxy-5-(4-methylphenyl)-5H-furan-2-one, with 4-trifluoromethylbenzaldehyde
>3-(2,1,3-benzothiadiazol-5-yl)-4-(4-trifluoromethylbenzyl)-5-hydroxy-5-(4-methylphenyl)-5H-furan-2-one, with 4-cyanobenzaldehyde
>3-(2,1,3-benzothiadiazol-5-yl)-4-(4-cyanobenzyl)-5-hydroxy-5-(4-methylphenyl)-5H-furan-2-one, with 4-methylbenzaldehyde
>3-(2,1,3-benzothiadiazol-5-yl)-4-(4-methylbenzyl)-5-hydroxy-5-(4-methylphenyl)-5H-furan-2-one, with 3-methyl-4-methoxybenzaldehyde
>3-(2,1,3-benzothiadiazol-5-yl)-4-(3-methyl-4-methoxybenzyl)-5-hydroxy-5-(4-methylphenyl)-5H-furan-2-one, with 4-tert-butylbenzaldehyde
>3-(2,1,3-benzothiadiazol-5-yl)-4-(4-tert-butylbenzyl)-5-hydroxy-5-(4-methylphenyl)-5H-furan-2-one, with (2-methoxycarbonylmethyloxy-4-methoxy) benzaldehyde 3-(2,1,3-benzothiadiazol-5-yl)-4-[(2-methoxycarbonylmethyloxy-4-methoxy)benzyl]-5-hydroxy-5-(4-methylphenyl)-5H-furan-2-one, with (2-carboxymethyloxy-4-methoxy)benzaldehyde 3-(2,1,3-benzothiadiazol-5-yl)-4-[(2-carboxymethyloxy-4-methoxy)benzyl]-5-hydroxy-5-(4-methylphenyl)-5H-furan-2-one, with 4-ethoxycarbonylbenzaldehyde 3-(2,1,3-benzothiadiazol-5-yl)-4-(4-ethoxycarbonylbenzyl)-5-hydroxy-5-(4-methylphenyl)-5H-furan-2-one, with 4-benzyloxybenzaldehyde 3-(2,1,3-benzothiadiazol-5-yl)-4-(4-benzyloxybenzyl)-5-hydroxy-5-(4-methylphenyl)-5H-furan-2-one, with 4-dimethylaminobenzaldehyde 3-(2,1,3-benzothiadiazol-5-yl)-4-(4-dimethylaminobenzyl)-5-hydroxy-5-(4-methylphenyl)-5H-furan-2-one, with 4-nitrobenzaldehyde 3-(2,1,3-benzothiadiazol-5-yl)-4-(4-nitrobenzyl)-5-hydroxy-5-(4-methylphenyl)-5H-furan-2-one, with (1,3-benzodioxol-5-yl)carbaldehyde 3-(2,1,3-benzothiadiazol-5-yl)-4-[(1,3-benzodioxol-5-yl)methyl]-5-hydroxy-5-(4-methylphenyl)-5H-furan-2-one, with 3-fluoro-4-methoxybenzaldehyde 3-(2,1,3-benzothiadiazol-5-yl)-4-(3-fluoro-4-methoxybenzyl)-5-hydroxy-5-(4-methylphenyl)-5H-furan-2-one, with 3-(N,N-dimethylamino)benzaldehyde 3-(2,1,3-benzothiadiazol-5-yl)-4-[3-(N,N-dimethylamino)benzyl]-5-hydroxy-5-(4-methylphenyl)-5H-furan-2-one;

with cyclohexanecarbaldehyde 3-(2,1,3-benzothiadiazol-5-yl)-4-(cyclohexylmethyl)-5-hydroxy-5-(4-methylphenyl-5H-furan-2-one [sic] and with cyclopentanecarbaldehyde 3-(2,1,3-benzothiadiazol-5-yl)-4-(cyclopentylmethyl)-5-hydroxy-5-(4-methylphenyl)-5H-furan-2-one [sic].

The following are obtained analogously by reaction of ethyl 2-(2,1,3-benzothiadiazol-5-yl)-4-phenyl-4-oxobutanoate with benzaldehyde 3-(2,1,3-benzothiadiazol-5-yl)-4-benzyl-5-hydroxy-5-phenyl-5H-furan-2-one, with 2-methoxybenzaldehyde 3-(2,1,3-benzothiadiazol-5-yl)-4-(2-methoxybenzyl)-5-hydroxy-5-phenyl-5H-furan-2-one, with 3-methoxybenzaldehyde 3-(2,1,3-benzothiadiazol-5-yl)-4-(3-methoxybenzyl)-5-hydroxy-5-phenyl-5H-furan-2-one, with 4-methoxybenzaldehyde 3-(2,1,3-benzothiadiazol-5-yl)-4-(4-methoxybenzyl)-5-hydroxy-5-phenyl-5H-furan-2-one, with 3,4-dimethoxybenzaldehyde 3-(2,1,3-benzothiadiazol-5-yl)-4-(3,4-dimethoxybenzyl)-5-hydroxy-5-phenyl-5H-furan-2-one, with 3,4,5-trimethoxybenzaldehyde 3-(2,1,3-benzothiadiazol-5-yl)-4-(3,4,5-trimethoxybenzyl)-5-hydroxy-5-phenyl-5H-furan-2-one, m.p. 174° with 3,4-diisopropoxy-5-methoxybenzaldehyde 3-(2,1,3-benzothiadiazol-5-yl)-4-(3,4-diisopropoxy-5-methoxybenzyl)-5-hydroxy-5-phenyl-5H-furan-2-one, with 3,4,5-triisopropoxybenzaldehyde 3-(2,1,3-benzothiadiazol-5-yl)-4-(3,4,5-triisopropoxybenzyl)-5-hydroxy-5-phenyl-5H-furan-2-one, with 4-trifluoromethylbenzaldehyde 3-(2,1,3-benzothiadiazol-5-yl)-4-(4-trifluoromethylbenzyl)-5-hydroxy-5-phenyl-5-furan-2-one, with 4-cyanobenzaldehyde 3-(2,1,3-benzothiadiazol-5-yl)-4-(4-cyanobenzyl)-5-hydroxy-5-phenyl-5H-furan-2-one, with 4-methylbenzaldehyde 3-(2,1,3-benzothiadiazol-5-yl)-4-(4-methylbenzyl)-5-hydroxy-5-phenyl-5H-furan-2-one, with 3-methyl-4-methoxybenzaldehyde 3-(2,1,3-benzothiadiazol-5-yl)-4-(3-methyl-4-methoxybenzyl)-5-hydroxy-5-phenyl-5H-furan-2-one, with 4-tert-butylbenzaldehyde 3-(2,1,3-benzothiadiazol-5-yl)-4-(4-tert-butylbenzyl)-5-hydroxy-5-phenyl-5H-furan-2-one, with (2-methoxycarbonylmethyloxy-4-methoxy) benzaldehyde 3-(2,1,3-benzothiadiazol-5-yl)-4-[(2-methoxycarbonylmethyloxy-4-methoxy)benzyl]-5-hydroxy-5-phenyl-5H-furan-2-one, with (2-carboxymethyloxy-4-methoxy)benzaldehyde 3-(2,1,3-benzothiadiazol-5-yl)-4-[(2-carboxymethyloxy-4-methoxy)benzyl]-5-hydroxy-5-phenyl-5H-furan-2-one, with 4-ethoxycarbonylbenzaldehyde 3-(2,1,3-benzothiadiazol-5-yl)-4-(4-ethoxycarbonylbenzyl)-5-hydroxy-5-phenyl-5H-furan-2-one, with 4-benzyloxybenzaldehyde 3-(2,1,3-benzothiadiazol-5-yl)-4-(4-benzyloxybenzyl)-5-hydroxy-5-phenyl-5H-furan-2-one, with 4-dimethylaminobenzaldehyde 3-(2,1,3-benzothiadiazol-5-yl)4-(4-dimethylaminobenzyl)-5-hydroxy-5-phenyl-5H-furan-2-one, with 4-nitrobenzaldehyde 3-(2,1,3-benzothiadiazol-5-yl)-4-(4-nitrobenzyl)-5-hydroxy-5-phenyl-5H-furan-2-one, with (1,3-benzodioxol-5-yl)carbaldehyde 3-(2,1,3-benzothiadiazol-5-yl)-4-[(1,3-benzodioxol-5-yl)methyl]-5-hydroxy-5-phenyl-5H-furan-2-one, with 3-fluoro-4-methoxybenzaldehyde 3-(2,1,3-benzothiadiazol-5-yl)-4-(3-fluoro-4-methoxybenzyl)-5-hydroxy-5-phenyl-5H-furan-2-one, with 3-(N,N-dimethylamino)benzaldehyde 3-(2,1,3-benzothiadiazol-5-yl)-4-[3-(N,N-dimethylamino)benzyl]-5-hydroxy-5-phenyl-5H-furan-2-one, with cyclohexanecarbaldehyde 3-(2,1,3-benzothiadiazol-5-yl)-4-cyclohexylmethyl-5-hydroxy-5-phenyl-5H-furan-2-one and with cyclopentanecarbaldehyde 3-(2,1,3-benzothiadiazol-5-yl)-4-cyclopentylmethyl-5-hydroxy-5-phenyl-5H-furan-2-one.

The following are obtained analogously by reaction of ethyl 2-(2,1,3-benzothiadiazol-5-yl)-4-(4-isopropoxyphenyl)-4-oxobutanoate with benzaldehyde
  3-(2,1,3-benzothiadiazol-5-yl)-4-benzyl-5-hydroxy-5-(4-isopropoxyphenyl)-5H-furan-2-one,
with 2-methoxybenzaldehyde
  3-(2,1,3-benzothiadiazol-5-yl)-4-(2-methoxybenzyl)-5-hydroxy-5-(4-isopropoxyphenyl)-5H-furan-2-one,
with 3-methoxybenzaldehyde
  3-(2,1,3-benzothiadiazol-5-yl)-4-(3-methoxybenzyl)-5-hydroxy-5-(4-isopropoxyphenyl)-5H-furan-2-one,
with 4-methoxybenzaldehyde
  3-(2,1,3-benzothiadiazol-5-yl)-4-(4-methoxybenzyl)-5-hydroxy-5-(4-isopropoxyphenyl)-5H-furan-2-one,
with 3,4-methoxybenzaldehyde
  3-(2,1,3-benzothiadiazol-5-yl)-4-(3,4-dimethoxybenzyl)-5-hydroxy-5-(4-isopropoxyphenyl)-5H-furan-2-one,
with 3,4,5-trimethoxybenzaldehyde
  3-(2,1,3-benzothiadiazol-5-yl)-4-(3,4,5-trimethoxybenzyl)-5-hydroxy-5-(4-isopropoxyphenyl)-5H-furan-2-one, m.p. 180°
with 3,4-diisopropoxy-5-methoxybenzaldehyde
  3-(2,1,3-benzothiadiazol-5-yl)-4-(3,4-diisopropoxy-5-methoxybenzyl)-5-hydroxy-5-(4-isopropoxyphenyl)-5H-furan-2-one, m.p. 170°
with 3,4,5-triisopropoxybenzaldehyde
  3(2,1,3-benzothiadiazol-5-yl)-4-(3,4,5-triisopropoxybenzyl)-5-hydroxy-5-(4-isopropoxyphenyl)-5H-furan-2-one,
with 4-trifluoromethylbenzaldehyde
  3-(2,1,3-benzothiadiazol-5-yl)-4-(4-trifluoromethylbenzyl)-5-hydroxy-5-(4-isopropoxyphenyl)-5H-furan-2-one,
with 4-cyanobenzaldehyde
  3-(2,1,3-benzothiadiazol-5-yl)-4-(4-cyanobenzyl)-5-hydroxy-5-(4-isopropoxyphenyl)-5H-furan-2-one,
with 4-methylbenzaldehyde
  3-(2,1,3-benzothiadiazol-5-yl)-4-(4-methylbenzyl)-5-hydroxy-5-(4-isopropoxyphenyl)-5H-furan-2-one,
with 3-methyl-4-methoxybenzaldehyde
  3-(2,1,3-benzothiadiazol-5-yl)-4(3-methyl-4-methoxybenzyl)-5-hydroxy-5-(4-isopropoxyphenyl)-5H-furan-2-one,
with 4-tert-butylbenzaldehyde
  3-(2,1,3-benzothiadiazol-5-yl)-4-(4-tert-butylbenzyl)-5-hydroxy-5-(4-isopropoxyphenyl)-5H-furan-2-one,
with (2-methoxycarbonylmethyloxy-4-methoxy)benzaldehyde
  3-(2,1,3-benzothiadiazol-5-yl)-4-[(2-methoxycarbonylmethyloxy-4-methoxy)benzyl]-5-hydroxy-5-(4-5isopropoxyphenyl)-5H-furan-2-one,
with (2-carboxymethyloxy-4-methoxy)benzaldehyde
  3-(2,1,3-benzothiadiazol-5-yl)-4-[(2-carboxymethyloxy-4-methoxy)benzyl]-5-hydroxy-5-(4-isopropoxyphenyl)-5H-furan-2-one,
with 4-ethoxycarbonylbenzaldehyde
  3-(2,1,3-benzothiadiazol-5-yl)-4-(4-ethoxycarbonylbenzyl)-5-hydroxy-5-(4-isopropoxyphenyl)-5H-furan-2-one,
with 4-benzyloxybenzaldehyde
  3-(2,1,3-benzothiadiazol-5-yl)-4-(4-benzyloxybenzyl-5-hydroxy-5-(4-isopropoxyphenyl)-5H-furan-2-one,
with 4-dimethylaminobenzaldehyde
  3-(2,1,3-benzothiadiazol-5-yl)-4-(4-dimethylaminobenzyl)-5-hydroxy-5-(4-isopropoxyphenyl)-5H-furan-2-one,
with 4-nitrobenzaldehyde
  3-(2,1,3-benzothiadiazol-5-yl)-4-(4-nitrobenzyl)-5-hydroxy-5-(4-isopropoxyphenyl)-5H-furan-2-one,
with (1,3-benzodioxol-5-yl)carbaldehyde
  3-(2,1,3-benzothiadiazol-5-yl)-4-[(1,3-benzodioxol-5-yl)methyl]-5-hydroxy-5-(4-isopropoxyphenyl)-5H-furan-2-one,
with 3-fluoro-4-methoxybenzaldehyde
  3-(2,1,3-benzothiadiazol-5-yl)-4-(3-fluoro-4-methoxybenzyl)-5-hydroxy-5-(4-isopropoxyphenyl)-5H-furan-2-one,
with 3-(N,N-dimethylamino)benzaldehyde
  3-(2,1,3-benzothiadiazol-5-yl)-4-[3-(N,N-dimethylamino)benzyl]-5-hydroxy-5-(4-isopropoxyphenyl)-5H-furan-2-one,
with cyclohexanecarbaldehyde
  3-(2,1,3-benzothiadiazol-5-yl)-4-cyclohexylmethyl-5-hydroxy-5-(4-isopropoxyphenyl)-5H-furan-2-one and
with cyclopentanecarbaldehyde
  3-(2,1,3-benzothiadiazol-5-yl)-4-cyclopentylmethyl-5-hydroxy-5-(4-isopropoxyphenyl)-5H-furan-2-one.

The following are obtained analogously by reaction of ethyl 2-(2,1,3-benzothiadiazol-5-yl)-4-(4-benzyloxyphenyl)-4-oxobutanoate
with benzaldehyde
  3-(2,1,3-benzothiadiazol-5-yl)-4-benzyl-5-hydroxy-5-(4-benzyloxyphenyl)-5H-furan-2-one,
with 2-methoxybenzaldehyde
  3-(2,1,3-benzothiadiazol-5-yl)-4-(2-methoxybenzyl)-5-hydroxy-5-(4-benzyloxyphenyl)-5H-furan-2-one,
with 3-methoxybenzaldehyde
  3-(2,1,3-benzothiadiazol-5-yl)-4-(3-methoxybenzyl)-5-hydroxy-5-(4-benzyloxyphenyl)-5H-furan-2-one,
with 4-methoxybenzaldehyde
  3-(2,1,3-benzothiadiazol-5-yl)-4-(4-methoxybenzyl)-5-hydroxy-5-(4-benzyloxyphenyl)-5H-furan-2-one,
with 3,4-dimethoxybenzaldehyde
  3-(2,1,3-benzothiadiazol-5-yl)-4-(3,4-dimethoxybenzyl)-5-hydroxy-5-(4-benzyloxyphenyl)-5H-furan-2-one,
with 3,4,5-trimethoxybenzaldehyde
  3-(2,1,3-benzothiadiazol-5-yl)-4-(3,4,5-trimethoxybenzyl)-5-hydroxy-5-(4-benzyloxyphenyl)-5H-furan-2-one,
with 3,4-diisopropoxy-5-methoxybenzaldehyde
  3-(2,1,3-benzothiadiazol-5-yl)-4-(3,4-diisopropoxy-5-methoxybenzyl)-5-hydroxy-5-(4-benzyloxyphenyl)-5H-furan-2-one,
with 3,4,5-triisopropoxybenzaldehyde
  3-(2,1,3-benzothiadiazol-5-yl)-4-(3,4,5-triisopropoxybenzyl)-5-hydroxy-5-(4-benzyloxyphenyl)-5H-furan-2-one,
with 4-trifluorobenzaldehyde
  3-(2,1,3-benzothiadiazol-5-yl)-4-(4-trifluoromethylbenzyl)-5-hydroxy-5-(4-benzyloxyphenyl)-5H-furan-2-one,
with 4-cyanobenzaldehyde
  3-(2,1,3-benzothiadiazol-5-yl)-4-(4-cyanobenzyl)-5-hydroxy-5-(4-benzyloxyphenyl)-5H-furan-2-one,
with 4-methylbenzaldehyde
  3-(2,1,3-benzothiadiazol-5-yl)-4-(4-methylbenzyl)-5-hydroxy-5-(4-benzyloxyphenyl)-5H-furan-2-one,
with 3-methyl-4-methoxybenzaldehyde
  3-(2,1,3-benzothiadiazol-5-yl)-4-(3-methyl-4-methoxybenzyl)-5-hydroxy-5-(4-benzyloxyphenyl)-5H-furan-2-one, with 4-tert-butylbenzaldehyde
    3-(2,1,3-benzothiadiazol-5-yl)-4-(4-tert-butylbenzyl)-5-hydroxy-5-(4-benzyloxyphenyl)-5H-furan-2-one,
with (2-methoxycarbonylmethyloxy-4-methoxy)benzaldehyde
    3-(2,1,3-benzothiadiazol-5-yl)-4-[(2-methoxycarbonylmethyloxy-4-methoxy)benzyl]-5-hydroxy-5-(4-benzyloxyphenyl)-5H-furan-2-one,
with (2-carboxymethyloxy-4-methoxy)benzaldehyde
    3-(2,1,3-benzothiadiazol-5-yl)-4-[(2-carboxymethyloxy-4-methoxy)benzyl]-5-hydroxy-5-(4-benzyloxyphenyl)-5H-furan-2-one,
with 4-ethoxycarbonylbenzaldehyde
    3-(2,1,3-benzothiadiazol-5-yl)-4-(4-ethoxycarbonylbenzyl)-5-hydroxy-5-(4-benzyloxyphenyl)-5H-furan-2-one,
with 4-benzyloxybenzaldehyde
    3-(2,1,3-benzothiadiazol-5-yl)-4-(4-benzyloxybenzyl)-5-hydroxy-5-(4-benzyloxyphenyl)-5H-furan-2-one,
with 4-dimethylaminobenzaldehyde
    3-(2,1,3-benzothiadiazol-5-yl)-4-(4-dimethylaminobenzyl)-5-hydroxy-5-(4-benzyloxyphenyl)-5H-furan-2-one,
with 4-nitrobenzaldehyde
    3-(2,1,3-benzothiadiazol-5-yl)-4-(4-nitrobenzyl)-5-hydroxy-5-(4-benzyloxyphenyl)-5H-furan-2-one,
with (1,3-benzodioxol-5-yl)carbaldehyde
    3-(2,1,3-benzothiadiazol-5-yl)-4-[(1,3-benzodioxol-5-yl)methyl]-5-hydroxy-5-(4-benzyloxyphenyl)-5H-furan-2-one,
with 3-fluoro-4-methoxybenzaldehyde
    3-(2,1,3-benzothiadiazol-5-yl)-4-(3-fluoro-4-methoxybenzyl)-5-hydroxy-5-(4-benzyloxyphenyl)-5H-furan-2-one,
with 3-(N,N-dimethylamino)benzaldehyde
    3-(2,1,3-benzothiadiazol-5-yl)-4-[3-(N,N-dimethylamino)benzyl]-5-hydroxy-5-(4-benzyloxyphenyl)-5H-furan-2-one,
with cyclohexanecarbaldehyde
    3-(2,1,3-benzothiadiazol-5-yl)-4-cyclohexylmethyl-5-hydroxy-5-(4-benzyloxyphenyl)-5H-furan-2-one and
with cyclopentanecarbaldehyde
    3-(2,1,3-benzothiadiazol-5-yl)-4-cyclopentylmethyl-5-hydroxy-5-(4-benzyloxyphenyl)-5H-furan-2-one.

The following are obtained analogously by reaction of ethyl 2-(2,1,3-benzothiadiazol-5-yl)-4-(3,4-dimethylphenyl)-4-oxobutanoate
with benzaldehyde
    3-(2,1,3-benzothiadiazol-5-yl)-4-benzyl-5-hydroxy-5-(3,4-dimethylphenyl)-5H-furan-2-one,
with 2-methoxybenzaldehyde
    3-(2,1,3-benzothiadjazol-5-yl)-4-(2-methoxybenzyl)-5-hydroxy-5-(3,4-dimethylphenyl)-5H-furan-2-one,
with 3-methoxybenzaldehyde
    3-(2,1,3-berizothiadiazol-5-yl)-4-(3-methoxybenzyl)-5-hydroxy-5-(3,4-dimethylphenyl)-5H-furan-2-one,
with 4-methoxybenzaldehyde
    3-(2,1,3-benzothiadiazol-5-yl)-4-(4-methoxybenzyl)-5-hydroxy-5-(3,4-dimethylphenyl)-5H-furan-2-one,
with 3,4-dimethoxybenzaldehyde
    3-(2,1,3-benzothiadiazol-5-yl)-4-(3,4-dimethoxybenzyl)-5-hydroxy-5-(3,4-dimethylphenyl)-5H-furan-2-one,
with 3,4,5-trimethoxybenzaldehyde
    3-(2,1,3-benzothiadiazol-5-yl)-4-(3,4,5-trimechoxybenzyl)-5-hydroxy-5-(3,4-dimethylphenyl)-5H-furan-2-one,
with 3,4-diisopropoxy-5-methoxybenzaldehyde
    3-(2,1,3-benzothiadiazol-5-yl)-4-(3,4-diisopropoxy-5-methoxybenzyl)-5-hydroxy-5-(3,4-dimethylphenyl)-5H-furan-2-one,
with 3,4,5-triisopropoxybenzaldehyde
    3-(2,1,3-benzothiadiazol-5-yl)-4-(3,4,5-triisopropoxybenzyl)-5-hydroxy-5-(3,4-dimethylphenyl)-5H-furan-2-one,
with 4-trifluoromethylbenzaldehyde
    3-(2,1,3-benzothiadiazol-5-yl)-4-(4-trifluoromethylbenzyl)-5-hydroxy-5-(3,4-dimethylphenyl)-5H-furan-2-one,
with 4-cyanobenzaldehyde
    3-(2,1,3-benzothiadiazol-5-yl)-4-(4-cyanobenzyl)-5-hydroxy-5-(3,4-dimethylphenyl)-5H-furan-2-one,
with 4-methylbenzaldehyde
    3-(2,1,3-benzothiadiazol-5-yl)-4-(4-methylbenzyl)-5-hydroxy-5-(3,4-dimethylphenyl-5H-furan-2-one,
with 3-methyl-4-methoxybenzaldehyde
    3-(2,1,3-benzothiadiazol-5-yl)-4-(3-methyl-4-methoxybenzyl)-5-hyydroxy-5-(3,4-dimethylphenyl)-5H-furan-2-one,
with 4-tert-butylbenzaldehyde
    3-(2,1,3-benzothiadiazol-5-yl)-4-(4-tert-butylbenzyl)-5-hydroxy-5-(3,4-dimethylphenyl)-5H-furan-2-one,
with (2-methoxycarbonylmethyloxy-4-methoxy)benzaldehyde
    3-(2,1,3-benzothiadiazol-5-yl)-4-[(2-methoxycarbonylmethyloxy-4-methoxy)benzyl]-5-hydroxy-5-(3,4-dimethylphenyl)-5H-furan-2-one,
with (2-carboxymethyloxy-4-methoxy)benzaldehyde
    3-(2,1,3-benzothiadiazol-5-yl)-4-[(2-carboxymethyloxy-4-methoxy)benzyl]-5-hydroxy-5-(3,4-dimethylphenyl)-5H-furan-2-one,
with 4-ethoxycarbonylbenzaldehyde
    3-(2,1,3-benzothiadiazol-5-yl)-4-(4-ethoxycarbonylbenzyl)-5-hydroxy-5-(3,4-dimethylphenyl)-5H-furan-2-one,
with 4-benzyloxybenzaldehyde
    3-(2,1,3-benzothiadiazol-5-yl)-4-(4-benzyloxybenzyl)-5-hydroxy-5-(3,4-dimethylphenyl)-5H-furan-2-one,
with 4-dimethylaminobenzaldehyde p1 3-(2,1,3-benzothiadiazol-5-yl)-4-(4-dimethylaminobenzyl)-5-hydroxy-5-(3,4-dimethylphenyl)-5H-furan-2-one,
with 4-nitrobenzaldehyde
    3-(2,1,3-benzothiadiazol-5-yl)-4-(4-nitrobenzyl)-5-hydroxy-5-(3,4-dimethylphenyl)-5H-furan-2-one,
with (1,3-benzodioxol-5-yl)carbaldebyde
    3-(2,1,3-benzothiadiazol-5-yl)-4-[(1,3-benzodioxol-5-yl)methyl]-5-hydroxy-5-(3,4-dimethylphenyl)-5H-furan-2-one,
with 3-fluoro-4-methoxybenzaldehyde
    3-(2,1,3-benzothiadiazol-5-yl)-4-(3-fluoro-4-methoxybenzyl)-5-hydroxy-5-(3,4-dimethylphenyl)-5H-furan-2-one,
with 3-(N,N-dimethylamino)benzaldehyde
    3-(2,1,3-benzothiadiazol-5-yl)-4-[3-(N,N-dimethylamino)benzyl]-5-hydroxy-5-(3,4-dimethylphenyl)-5H-furan-2-one,
with cyclohexanecarbaldehyde
    3-(2,1,3-benzothiadiazol-5-yl)-4-cyclohexylmethyl-5-hydroxy-5-(3,4-diethylphenyl)-5H-furan-2-one and
with cyclopentanecarbaldehyde
    3-(2,1,3-benzothiadiazol-5-yl)-4-cyclopentylmethyl-5-hydroxy-5-(3,4-dimethylphenyl)-5H-furan-2-one.

The following are obtained analogously by reaction of ethyl 2-(2,1,3-benzothiadiazol-5-yl)-4-(1,3-benzodioxol-5-yl)-4-oxobutanoate with benzaldehyde
   3-(2,1,3-benzothiadiazol-5-yl)-4-benzyl-5-hydroxy-5-(1,3-benzo dioxol-5-yl)-5H-furan-2-one, m.p. 71°
with 2-methoxybenzaldehyde
   3-(2,1,3-benzothiadiazol-5-yl)-4-(2-methoxybenzyl)-5-hydroxy-5-(1,3-benzodioxol-5-yl)-5H-furan-2-one,
with 3-methoxybenzaldehyde
   3-(2,1,3-benzothiadiazol-5-yl)-4-(3-methoxybenzyl)-5-hydroxy-5-(1,3-benzodioxol-5-yl)-5H-furan-2-one,
with 4-methoxybenzaldehyde
   3-(2,1,3-benzothiadiazol-5-yl)-4-(4-methoxybenzyl)-5-hydroxy-5-(1,3-benzodioxol-5-yl)-5H-furan-2-one,
with 3,4-dimethoxybenzaldehyde
   3-(2,1,3-benzothiadiazol-5-yl)-4-(3,4-dimethoxybenzyl)-5-hydroxy-5-(1,3-benzodioxol-5-yl)-5H-furan-2-one,
with 3,4,5-trimethoxybenzaldehyde
   3-(2,1,3-benzothiadiazol-5-yl)-4-(3,4,5-trimethoxybenzyl)-5-hydroxy-5-(1,3-benzodioxol-5-yl)-5H-furan-2-one, m.p. 86°
with 3,4-diisopropoxy-5-methoxybenzaldehyde
   3-(2,1,3-benzothiadiazol-5-yl)-4-(3,4-diisopropoxy-5-methoxybenzyl)-5-hydroxy-5-(1,3-benzodioxol-5-yl)-5H-furan-2-one,
with 3,4,5-triisopropoxybenzaldehyde
   3-(2,1,3-benzothiadiazol-5-yl)-4-(3,4,5-triisopropoxybenzyl)-5-hydroxy-5-(1,3-benzodioxol-5-yl)-5H-furan-2-one,
with 4-trifluoromethylbenzaldehyde
   3-(2,1,3-benzothiadiazol-5-yl)-4-(4-trifluoromethylbenzyl)-5-hydroxy-5-(1,3-benzodioxol-5-yl)-5H-furan-2-one,
with 4-cyanobenzaldehyde
   3-(2,1,3-benzothiadiazol-5-yl)-4-(4-cyanobenzyl)-5-hydroxy-5-(1,3-benzodioxol-5-yl)-5H-furan-2-one,
with 4-methylbenzaldehyde
   3-(2,1,3-benzothiadiazol-5-yl)-4-(4-methylbenzyl)-5-hydroxy-5-(1,3-benzodioxol-5-yl)-5H-furan-2-one,
with 3-methyl-4-methoxybenzaldehyde
   3-(2,1,3-benzothiadiazol-5-yl)-4-(3-methyl-4-methoxybenzyl)-5-hydroxy-5-(1,3-benzodioxol-5-yl)-5H-furan-2-one,
with 4-tert-butylbenzaldehyde
   3-(2,1,3-benzothiadiazol-5-yl)-4-(4-tert-butylbenzyl)-5-hydroxy-5-(1,3-benzodioxol-5-yl)-5H-furan-2-one,
with (2-methoxycarbonylmethyloxy-4-methoxy)benzaldehyde
   3-(2,1,3-benzothiadiazol-5-yl)-4-[(2-methoxycarbonylmethyloxy-4-methoxy)benzyl]-5-hydroxy-5-(1,3-benzodioxol-5-yl)-5H-furan-2-one,
with (2-carboxyethyloxy-4-methoxy)benzaldehyde
   3-(2,1,3-benzothiadiazol-5-yl)-4-[(2-carboxymethyloxy-4-methoxy)benzyl]-5-hydroxy-5-(1,3-benzodioxol-5-yl)-5H-furan-2-one,
with 4-ethoxycarbonylbenzaldehyde
   3-(2,1,3-benzothiadiazol-5-yl)-4-(4-ethoxycarbonylbenzyl)-5-hydroxy-5-(1,3-benzodioxol-5-yl)-5H-furan-2-one,
with 4-benzyloxybenzaldehyde
   3-(2,1,3-benzothiadiazol-5-yl)-4-(4-benzyloxybenzyl)-5-hydroxy-5-(1,3-benzodioxol-5-yl)-5H-furan-2-one,
with 4-dimethylaminobenzaldehyde
   3-(2,1,3-benzothiadiazol-5-yl)-4-(4-dimethylaminobenzyl)-5-hydroxy-5-(1,3-benzodioxol-5-yl)-5H-furan-2-one,
with 4-nitrobenzaldehyde
   3-(2,1,3-benzothiadiazol-5-yl)-4-(4-nitrobenzyl)-5-hydroxy-5-(1,3-benzodioxol-5-yl)-5H-furan-2-one,
with (1,3-benzodioxol-5-yl)carbaldehyde
   3-(2,1,3-benzothiadiazol-5-yl)-4-[(1,3-benzodioxol-5-yl)methyl]-5-hydroxy-5-(1,3-benzodioxol-5-yl)-5H-furan-2-one,
with 3-fluoro-4-methoxybenzaldehyde
   3-(2,1,3-benzothiadiazol-5-yl)-4-(3-fluoro-4-methoxybenzyl)-5-hydroxy-5-(1,3-benzodioxol-5-yl)-5H-furan-2-one,
with 3-(N,N-dimethylamino)benzaldehyde
   3-(2,1,3-benzothiadiazol-5-yl)-4-[3-(N,N-dimethylamino)benzyl]-5-hydroxy-5-(1,3-benzodioxol-5-yl)-5H-furan-2-one,
with cyclohexanecarbaldehyde
   3-(2,1,3-benzothiadiazol-5-yl)-4-cyclohexylmethyl-5-hydroxy-5-(1,3-benzodioxol-5-yl)-5H-furan-2-one and
with cyclopentamecarbaldehyde
   3-(2,1,3-benzothiadiazol-5-yl)-4-cyclopentylmethyl-5-hydroxy-5-(1,3-benzodioxol-5-yl)-5H-furan-2-one.

The following are obtained analogously by reaction of ethyl 2-(2,1,3-benzothiadiazol-5-yl)-4-(3,4,5-trimethoxyphenyl)-4-oxobutanoate with benzaldehyde
   3-(2,1,3-benzothiadiazol-5-yl)-4-benzyl-5-hydroxy-5-(3,4,5-trimethoxyphenyl)-5H-furan-2-one,
with 2-methoxybenzaldehyde
   3-(2,1,3-benzothiadiazol-5-yl)-4-(2-methoxybenzyl)-5-hydroxy-5-(3,4,5-trimethoxypheryl)-5H-furan-2-one,
with 3-methoxybenzaldehyde
   3-(2,1,3-benzothiadiazl-5-yl)-4-(3-methoxybenzyl)-5-hydroxy-5-(3,4,5-trimethoxyphenyl)-5H-furan-2-one,
with 4- methoxybenzaldehyde
   3-(2,1,3-benzothiadiazol-5-yl)-4-(4-methoxybenzyl)-5-hydroxy-5-(3,4,5-trimethoxyphenyl)-5H-furan-2-one,
with 3,4-dimethoxybenzaldehyde
   3-(2,1,3-benzothiadiazol-5-yl)-4-(3,4-dimethoxybenzyl)-5-hydroxy-5-(3,4,5-trimethoxyphenyl)-5H-furan-2-one,
with 3,4,5-trimethoxybenzaldehyde
   3-(2,1,3-benzothiadiazol-5-yl)-4-(3,4,5-trimethoxybenzyl)-5-hydroxy-5-(3,4,5-trimethoxyphenyl)-5H-furan -2-one, m.p. 70°
with 3,4-diisopropoxy -5-methoxybenzaldehyde
   3-(2,1,3-benzothiadiazol-5-yl)-4-(3,4-diisopropoxy-5-methoxybenzyl)-5-hydroxy-5-(3,4,5-trimethoxyphenyl)-5H-furan-2-one, m.p. 61°
with 3,4,5-triisopropoxybenzaldehyde
   3-(2,1,3-benzothiadiazol-5-yl)-4-(3,4,5-triisopropoxybenzyl)-5-hydroxy-5-(3,4,5-trimethoxyphenyl)-5H-furan-2-one,
with 4-trifluoromethylbenzaldehyde
   3-(2,1,3-benzothiadiazol-5-yl)-4-(4-trifluoromethylbenzyl)-5-hydroxy-5-(3,4,5-trimethoxyphenyl)-5H-furan-2-one,
with 4-cyanobenzaldehyde
   3-(2,1,3-benzothiadiazol-5-yl)-4-(4-cyanobenzyl)-5-hydroxy-5-(3,4,5-trimethoxyphenyl)-5H-furan-2-one, with 4-methylbenzaldehyde
  3-(2,1,3-benzothiadiazol-5-yl)-4-(4-methylbenzyl)-5-hydroxy-5-(3,4,5-trimethoxyphenyl)-5H-furan-2-one,
with 3-methyl-4-methoxybenzaldehyde
  3-(2,1,3-benzothiadiazol-5-yl)-4-(3-methyl-4-methoxybenzyl)-5-hydroxy-5-(3,4,5-trimethoxyphenyl)-5H-furan-2-one,
with 4-tert-butylbenzaldehyde
  3-(2,1,3-benzothiadiazol-5-yl)-4-(4-tert-butylbenzyl)-5-hydroxy-5-(3,4,5-trimethoxyphenyl)-5H-furan-2-one,
with (2-methoxycarbonylmethyloxy-4-methoxy)benzaldehyde
  3-(2,1,3-benzothiadiazol-5-yl)-4-[(2-methoxycarbonylmethyloxy-4-methoxy)benzyl]-5-hydroxy-5-(3,4,5-trimethoxyphenyl)-5H-furan-2-one,
with (2-carboxymethyloxy-4-methoxy)benzaldehyde
  3-(2,1,3-benzothiadiazol-5-yl)-4-[(2-carboxymethyloxy-4-methoxy)benzyl]-5-hydroxy-5-(3,4,5-trimethoxyphenyl)-5H-furan-2-one,
with 4-ethoxycarbonylbenzaldehyde
  3-(2,1,3-benzothiadiazol-5-yl)-4-(4-ethoxycarbonylbenzyl)-5-hydroxy-5-(3,4,5-trimethoxyphenyl)-5H-furan-2-one,
with 4-benzyloxybenzaldehyde
  3-(2,1,3-benzothiadiazol-5-yl)-4-(4-benzyloxybenzyl)-5-hydroxy-5-(3,4,5-trimethoxyphenyl)-5H-furan-2-one,
with 4-dimethylaminobenzaldehyde
  3-(2,1,3-benzothiadiazol-5-yl)-4-(4-dimethylaminobenzyl)-5-hydroxy-5-(3,4,5-trimethoxyphenyl)-5H-furan-2-one,
with 4-nitrobenzaldehyde
  3-(2,1,3-benzothiadiazol-5-yl)-4-(4-nitrobenzyl)-5-hydroxy-5-(3,4,5-trimethoxyphenyl)-5H-furan-2-one,
with (1,3-benzodioxol-5-yl)carbaldehyde
  3-(2,1,3-benzothiadiazol-5-yl)-4-[(1,3-benzodioxol-5-yl)methyl]-5-hydroxy-5-(3,4,5-trimethoxyphenyl)-5H-furan-2-one,
with 3-fluoro-4-methoxybenzaldehyde
  3-(2,1,3-benzothiadiazol-5-yl)-4-(3-fluoro-4-methoxybenzyl)-5-hydroxy-5-(3,4,5-trimethoxyphenyl)-5H-furan-2-one,
with 3-(N,N-dimethylamino)benzaldehyde
  3-(2,1,3-benzothiadiazol-5-yl)-4-[3-(N,N-dimethylamino)benzyl]-5-hydroxy-5-(3,4,5-trimethoxyphenyl)-5H-furan-2-one and
with cyclohexanecarbaldehyde
  3-(2,1,3-benzothiadiazol-5-yl)-4-cyclohexylmethyl-5-hydroxy-5-(3,4,5-trimethoxyphenyl)-5H-furan-2-one and
with cyclopentanecarbaldehyde
  3-(2,1,3-benzothiadiazol-5-yl)-4-cyclopentylmethyl-5-hydoxy-5-(3,4,5-trimethoxyphenyl)-5H-furan-2-one.

The following are obtained analogously by reaction of ethyl 2-(2,1,3-benzothiadiazol-5-yl)-4-(3,4-dimethoxyphenyl)-4-oxobutanoate
with benzaldehyde
  3-(2,1,3-benzothiadiazol-5-yl)-4-benzyl-5-hydroxy-5-(3,4-dimethoxyphenyl)-5H-furan-2-one,
with 2-methoxybenzaldehyde
  3-(2,1,3-benzothiadiazol-5-yl)-4-(2-methoxybenzyl)-5-hydroxy-5-(3,4-dimethoxyphenyl )-5H-furan-2-one,
with 3-methoxybenzaldehyde
  3-(2,1,3-benzothiadiazol-5-yl)-4-(3-methoxybenzyl)-5-hydroxy-5-(3,4-dimethoxyphenyl)-5H-furan -2-one,
with 4-methoxybenzaldehyde
  3-(2,1,3-benzothiadiazol-5-yl)-4-(4-methoxybenzyl)-5-hydroxy-5-(3,4-dimethoxphenyl)-5H-furan-2-one,
with 3,4-dimethoxybenzaldehyde
  3-(2,1,3-benzothiediazol-5-yl)-4-(3,4-dimethoxybenzyl)-5-hydroxy-5-(3,4-dimethoxyphenyl)-5H-furan-2-one,
with 3,4,5-trimethoxybenzaldehyde
  3-(2,1,3-benzothiadiazol-5-yl)-4-(3,4,5-trimethoxybenzyl)-5-hydroxy-5-(3,4-dimethoxyphenyl)-5H-furan-2-one,
with 3,4-diisopropoxy-5-methoxybenzaldehyde
  3-(2,1,3-benzothiadiazol-5-yl)-4-(3,4-diisopropoxy-5-methoxybenzyl)-5-hydroxy-5-(3,4-dimethoxyphenyl)-5H-furan-2-one,
with 3,4,5-triisopropoxybenzaldehyde
  3-(2,1,3-benzothiadiazol-5-yl)-4-(3,4,5-triisopropoxybenzyl)-5-hydroxy-5-(3,4-dimethoxyphenyl)-5H-furan-2-one,
with 4-trifluoromethylbenzaldehyde
  3-(2,1,3-benzothiadiazol-5-yl)-4-(4-trifluoromethylbenzyl)-5-hydroxy-5-(3,4-dimethoxyphenyl)-5H-furan-2-one,
with 4-cyanobenzaldehyde
  3-(2,1,3-benzothiadiazol-5-yl)-4-(4-cyanobenzyl)-5-hydroxy-5-(3,4-dimethoxyphenyl)-5H-furan-2-one,
with 4-methylbenzaldehyde
  3-(2,1,3-benzothiadiazol-5-yl)-4-(4-methylbenzyl)-5-hydroxy-5-(3,4-dimethoxyphenyl)-5H-furan-2-one,
with 3-methyl-4-methoxybenzaldehyde
  3-(2,1,3-benzothiadiazol-5-yl)-4-(3-methyl-4-methoxybenzyl)-5-hydroxy-5-(3,4-dimethoxyphenyl)-5H-furan-2-one,
with 4-tert-butylbenzaldehyde
  3-(2,1,3-benzothiadiazol-5-yl)-4-(4-tert-butylbenzyl)-5-hydroxy-5-(3,4-dimethoxyphenyl)-5H-furan-2-one,
with (2-methoxycarbonylmethyloxy-4-methoxy)benzaldehyde
  3-(2,1,3-benzothiadiazol-5-yl)-4-[(2-methoxycarbonylmethyloxy-4-methoxy)benzyl]-5-hydroxy-5-(3,4-dimethoxyphenyl)-5H-furan-2-one,
with (2-carboxymethyloxy-4-methoxy)benzaldehyde
  3-(2,1,3-benzothiadiazol-5-yl)-4-[(2-carboxymethyloxy-4-methoxy)benzyl]-5-hydroxy-5-(3,4-dimethoxyphenyl)-5H-furan-2-one,
with 4- rethoxycarbonylbenzaldehyle
  3-(2,1,3-benzothiadiazol-5-yl)-4-(4-ethoxycarbonylbenzyl)-5-hydroxy-5-(3,4-dimethoxyphenyl)-5H-furan-2-one,
with 4-benzyloxybenzaldehyde
  3-(2,1,3-benzothiadiazol-5-yl)-4-(4-benzyloxybenzyl)-5-hydroxy-5-(3,4-dimethoxyphenyl)-5H-furan-2-one,
with 4-dimethylaminobenzaldehyde
  3-(2,1,3-benzothiadiazol-5-yl)-4-(4-dimethylaminobenzyl)-5-hydroxy-5-(3,4-dimethoxyphenyl)-5H-furan-2-one,
with 4-nitrobenzaldehyde
  3-(2,1,3-benzothiadiazol-5-yl)-4-(4-nitrobenzyl)-5-hydroxy-5-(3,4-dimethoxyphenyl)-5H-furan-2-one ,
with (1,3-benzodioxol-5-yl)carbaldehyde
  3-(2,1,3-benzothiadiazol-5-yl)-4-[(1,3-benzodioxol-5-yl)methyl]-5-hydroxy-5-(3,4-dimethoxyphenyl)-5H-furan-2-one,
with 3-fluoro-4-methoxybenzaldehyde
  3-(2,1,3-benzothiadiazol-5-yl)-4-(3-fluoro-4-methoxybenzyl)-5-hydroxy-5-(3,4-dimethoxyphenyl)-5H-furan-2-one, with 3-(N,N-dimethylamino)benzaldehyde
   3-(2,1,3-benzothiadiazol-5-yl)-4-[3-(N,N-dimethylamino)benzyl]-5-hydroxy-5-(3,4-dimethoxyphenyl)-5H-furan-2-one,
with cyclohexanecarbaldehyde
   3-(2,1,3-benzothiadiazol-5-yl)-4-cyclohexylmethyl-5-hydroxy-5-(3,4-dimethoxyphenyl)-5H-furan-2-one and
with cyclopentanecarbaldehyde
   3-(2,1,3-benzothiadiazol-5-yl)-4-cyclopentylmethyl-5-hydroxy-5-(3,4- dimethoxyphenyl)-5H-furan-2-one.

The following are obtained analogously by reaction of ethyl 2-(2,1,3-benzothiadiazol-5-yl)-4-(4-methylthiophenyl)-4-oxobutanoate
with benzaldehyde
   3-(2,1,3-benzothiadiazol-5-yl)-4-benzyl-5-hydroxy-5-(4-methylthiophenyl)-5H-furan-2-one,
with 2-methoxybenzaldehyde
   3-(2,1,3-benzothiadiazol-5-yl)-4-(2-methoxybenzyl)-5-hydroxy-5-(4-methylthiophenyl)-5H-furan-2-one,
with 3-methoxybenzaldehyde
   3-(2,1, 3-benzothiadiazol-5-yl)-4-(3-methoxybenzyl)-5-hydroxy-5-(4-methylthiophenyl)-5H-furan-2- one,
with 4-methoxybenzaldehyde
   3-(2,1,3-benzothiadiazol-5-yl)-4-(4-methoxybenzyl)-5-hydroxy-5-(4-methylthiophenyl)-5H-furan-2-one,
with 3,4-dimethoxybenzaldehyde
   3-(2,1,3-benzothiadiazol-5-yl)-4-(3,4-dimethoxybenzyl)-5-hydroxy-5-(4-methylthiophenyl)-5H-furan-2-one ,
with 3,4,5-trimethoxybenzaldehyde
   3-(2,1,3-benzothiadiazol-5-yl)-4-(3,4,5-trimethoxybenzyl)-5-hydroxy-5-(4-methylthiophenyl)-5H-furan-2-one,
with 3,4-diisopropoxy-5-methoxybenzaldehyde
   3-(2,1,3-benzothiadiazol-5-yl)-4-(3,4-diisopropoxy-5-methoxybenzyl)-5-hydroxy-5-(4-methylthiophenyl)-5H-furan-2-one,
with 3,4,5-triisopropoxybenzaldehyde
   3-(2,1,3-benzothiadiazol-5-yl)-4-(3,4,5-triisopropoxybenzyl)-5-hydroxy-5-(4-methylthiophenyl)-5H-furan-2-one,
with 4-trifluorobenzaldehyde
   3-(2,1,3-benzothiadiazol-5-yl)-4-(4-trifluoromethylbenzyl)-5-hydroxy-5-(4-methylthiophenyl)-5H-furan-2-one,
with 4-cyanobenzaldehyde
   3-(2,1,3-benzothiadiazol-5-yl)-4-(4-cyanobenzyl)-5-hydroxy-5-(4-methylthiophenyl)-5H-furan-2-one,
with 4-methylbenzaldehyde
   3-(2,1,3-benzothiadiazol-5-yl)-4-(4-methylbenzyl)-5-hydroxy-5-(4-methylthiophenyl)-5H-furan-2-one,
with 3-methyl-4-methoxybenzaldehyde
   3-(2,1,3-benzothiadiazol-5-yl)-4-(3-methyl-4-methoxybenzyl)-5-hydroxy-5-(4-methylthiophenyli-5H-furan-2-one,
with 4-tert-butylbenzaldehyde
   3-(2,1,3-benzothiadiazol-5-yl)-4-(4-tert-butylbenzyl)-5-hydroxy-5-(4-methylthiophenyl)-5H-furan-2-one,
with (2-methoxycarbonylmethyloxy-4-methoxy)benzaldehyde
   3-(2,1,3-benzothiadiazol-5-yl)-4-[(2-methoxycarbonylmethyloxy-4-methoxy)benzyl]-5-hydroxy-5-(4-methylthiophenyl)-5H-furan-2-one,
with (2-carboxymethyloxy-4-methoxy)benzaldehyde
   3-(2,1,3-benzothiadiazol-5-yl)-4-[(2-carboxymethyloxy-4-methoxy)benzyl]-5-hydroxy-5-(4-methylthiophenyl)-5H-furan-2-one,
with 4-ethoxycarbonylbenzaldehyde
   3-(2,1,3-benzothiadiazol-5-yl)-4-(4-ethoxycarbonylbenzyl)-5-hydroxy-5-(4-methylthiophenyl)-5H-furan-2-one,
with 4-benzyloxybenzaldehyle
   3-(2,1,3-benzothiadiazol-5-yl)-4-(4-benzyloxybenzyl)-5-hydroxy-5-(4-methylthiophenyl)-5H-furan-2-one,
with 4-dimethylaminobenzaldehyde
   3-(2,1,3-benzothiadiazol-5-yl)-4-(4-dimethylaminobenzyl)-5-hydroxy-5-(4-methylthiophenyl)-5H-furan-2-one,
with 4-nitrobenzaldehyde
   3-(2,1,3-benzothiadiazol-5-yl)-4-(4-nitrobenzyl)-5-hydroxy-5-(4-methylthiophenyl)-5H-furan-2-one ,
with (1,3-benzodioxol-5-yl)carbaldehyde
   3-(2,1,3-benzothiadiazol-5-yl)-4-[(1,3-benzodioxol-5-yl)methyl]-5-hydroxy-5-(4-methylthiophenyl)-5H-furan-2-one,
with 3-fluoro-4-methoxybenzaldehyde
   3-(2,1,3-benzothiadiazol-5-yl)-4-(3-fluoro-4-methoxybenzyl)-5-hydroxy-5-(4-methylthiophenyl)-5H-furan-2-one,
with 3-(N,N-dimethylamino)benzaldehyde
   3-(2,1,3-benzothiadiazol-5-yl)-4-[3-(N,N-dimethylamino)benzyl]-5-hydroxy-5-(4-methylthiopheyl)-5H-furan-2-one,
with cyclohexanecarbaldehyde
   3-(2,1,3-benzothiadiazol-5-yl)-4-cyclohexylmethyl-5-hydroxy-5-(4-methylthiophenyl)-5H-furan-2-one and
with cyclopentanecarbaldehyde.
   3-(2,1,3-benzothiadiazol-5-yl)-4-cyclopentylmethyl-5-hydroxy-5-(4-methylthiophenyl)-5H-furan-2-one.

The following are obtained analogously by reaction of ethyl 2-(2,1,3-benzoxadiazol-5-yl)-4-(4-methoxyphenyl)-4-oxobutanoate
with benzaldehyde
   3-(2,1,3-benzoxadiazol-5-yl)-4-benzyl-5-hydroxy-5-(4-methoxyphenyl)-5H-furan-2-one,
with 2-methoxybenzaldehyde
   3-(2,1,3-benzoxa diazol-5-yl)-4-(2-methoxybenzyl)-5-hydroxy-5-(4-methoxyphenyl)-5H-furan-2-one,
with 3-methoxybenzaldehyde
   3-(2,1,3-benzoxadiazol-5-yl)-4-(3-methoxybenzyl)-5-hyldroxy-5-(4-methoxyphenyl)-5H-furan-2-one,
with 4-methoxybenzaldehyde
   3-(2,1,3-benzoxadiazol-5-yl)-4-(4-methoxybenzyl)-5-hydroxy-5-(4-methoxyphenyl)-5H-furan-2-one,
with 3,4-dimethoxybenzaldehyde
   3-(2,1,3-benzoxadiazol-5-yl)-4-(3,4-dimethoxybenzyl)-5-hydroxy-5-(4-methoxyphenyl)-5H-furan-2-one,
with 3,4,5-trimethoxybenzaldehyde
   3-(2,1,3-benzoxadiazol-5-yl)-4-(3,4,5-trimethoxybenzyl)-5-hydroxy-5-(4-methoxyphenyl)-5H-furan-2-one,
with 3,4-diisopropoxy-5-methoxybenzaldehyde
   3-(2,1,3-benzoxadiazol-5-yl)-4-(3,4-diisopropoxy-5-methoxybenzyl)-5-hydroxy-5-(4-methoxyphenyl)-5H-furan-2-one,
with 3,4,5-triisopropoxybenzaldehyde
   3-(2,1,3-benzoxadiazol-5-yl)-4-(3,4,5-triisopropoxybenzyl)-5-hydroxy-5-(4-methoxyphenyl)-5H-furan-2-one,
with 4-trifluoromethylbenzaldehyde
   3-(2,1,3-benzoxadiazol-5-yl)-4-(4-trifluoromethylbenzyl)-5-hydroxy-5-(4-methoxyphenyl)-5H-furan-2-one, with 4-cyanobenzaldehyde
  3-(2,1,3-benzoxadiazol-5-yl)-4-(4-cyanobenzyl)-5-hydroxy-5-(4-methoxyphenyl)-5H-furan-2-one,
with 4-methylbenzaldehyde
  3-(2,1,3-benzox odiazol-5-yl)-4-(4-methylbenzyl)-5-hydroxy-5-(4-methoxyphenyl)-5H-furan-2-one,
with 3-methyl-4-methoxybenzaldehyde
  3-(2,1,3-benzoxadiazol-5-yl)-4-(3-methyl-4-methoxybenzyl)-5-hydroxy-5-(4-methoxyphenyl)-5H-furan-2-one,
with 4-tert-butylbenzaldehyde
  3-(2,1,3-benzoxadiazol-5-yl)-4-(4-tert-butylbenzyl)-5-hydroxy-5-(4-methoxyphenyl)-5H-furan-2-one,
with (2-methoxycarbonylmethyloxy-4-methoxy)benzaldehyde
  3-(2,1,3-benzoxadiazol-5-yl)-4-[(2-methoxycarbonylmethyloxy-4-methoxy)benzyl]-5-hydroxy-5-(4-methoxyphenyl)-5H-furan-2-one,
with (2-carboxmethyloxy-4-methoxy)benzaldehyde
  3-(2,1,3-benzoxadiazol-5-yl)-4-[(2-carboxymethyloxy-4-methoxy)benzyl]-5-hydroxy-5-(4-methoxyphenyl)-5H-furan-2-one,
with 4-ethoxycarbonylbenzaldehyde
  3-(2,1,3-benzoxadiazol-5-yl)-4-(4-ethoxycarbonylbenzyl)-5-hydroxy-5-(4-methoxyphenyl)-5H-furan-2-one,
with 4-benzyloxybenzaldehyde
  3-(2,1,3-benzoxadiazol-5-yl)-4-(4-benzyloxybenzyl)-5-hydroxy-5-(4-methoxyphenyl)-5H-furan-2-one,
with 4-dimethylaminobenzaldehyde
  3-(2,1,3-benzoxadiazol-5-yl)-4-(4-dimethylaminobenzyl)-5-hydroxy-5-(4-methoxyphenyl)-5H-furan-2-one,
with 4-nitrobenzaldehyde
  3-(2,1,3-benzoxadiazol-5-yl)-4-(4-nitrobenzyl)-5-hydroxy-5-(4-methoxyphenyl)-5H-furan-2-one,
with (1,3-benzodioxol-5-yl)carbaldehyde
  3-(2,1,3-benzoxadiazol-5-yl)-4-[(1,3-benzodioxol-5-yl)methyl]-5-hydroxy-5-(4-methoxyphenyl)-5H-furan-2-one,
with 3-fluoro-4-methoxybenzaldehyde
  3-(2,1,3-benzoxadiazol-5-yl)-4-(3-fluoro-4-methoxybenzyl)-5-hydroxy-5-(4-methoxyphenyl)-5H-furan-2-one,
with 3-(N,N-dimethylamino)benzaldehyde
  3-(2,1,3-benzoxadiazol-5-yl)-4-[3-(N,N-dimethylamino)benzyl]-5-hydroxy-5-(4-methoxyphemyl)-5H-furan-2-one,
with cyclohexanecarbaldehyde
  3-(2,1,3-benzoxadiazol-5-yl)-4-cyclohexylmethyl-5-hydroxy-5-(4-methoxyphenyl)-5H-furan-2-one and
with cyclopentanecarbaldehyde
  3-(2,1,3-benzoxadiazol-5-yl)-4-cyclopentylmethyl-5-hydroxy-5-(4-methoxyphenyl)-5H-furan-2-one.

EXAMPLE 2

0.7 ml of 0.1 N NaOH is added to a suspension of 30 mg of 3-(2,1,3-benzothiadiazol-5-yl)-4-benzyl-5-hydroxy-5-(4-methoxyphenyl)-5H-furan-2-one in 1 ml of methanol and the mixture is stirred at room temperature. The solvent is removed, the residue is partitioned between water and diethyl ether, and the agueous phase is then lyophilized. Sodium 2-(2,1,3-benzothiadiazol-5-yl)- 3-benzyl-4-(4-methoxyphenyl)-4-oxo-2-butenoate, FAB 453, is obtained.

Analogously, by treatment of the furan derivatives mentioned in Example 1 with NAOH, the sodium salts of the corresponding open-chain 4-oxo-2-butenoic acid derivatives are obtained:

sodium 2-(2,1,3-benzothiadiazol-5-yl)-3-(2-methoxybenzyl)-4-(4-methoxyphenyl)-4-oxo-2-butenoate, sodium 2-(2,1,3-benzothiadiazol-5-yl)-3-(3-methoxybenzyl)-4-(4-methoxyphenyl)-4-oxo-2-butenoate, sodium 2-(2,1,3-benzothiadiazol-5-yl)-3-(4-methoxybenzyl)-4-(4-methoxyphenyl)-4-oxo-2-butenoate, sodium 2-(2,1,3-benzothiadiazol-5-yl)-3-(3,4-dimethoxybenzyl)-4-(4-methoxyphenyl)-4-oxo-2-butenoate, sodium 2-(2,1,3-benzothiadiazol-5-yl)-3-(3,4,5-trimethoxybenzyl)-4-(4-methoxyphenyl)-4-oxo-2-butenoate, m.p , 245° (dec.)

sodium 2-(2,1,3-benzothiadiazol-5-yl)-3-(3,4-diisopropoxy-5-methoxybenzyl)-4-(4-methoxyphenyl)-4-oxo-2-butenoate, FAB 599 sodium 2-(2,1,3-benzothiadiazol-5-yl)-3-(3,4,5-triisopropoxybenzyl)-4-(4-methoxyphenyl)-4-oxo-2-butenoate, sodium 2-(2,1,3-benzothiadiazol-5-yl)-3-(4-trifluoromethylbenzyl)-4-(4-methoxyphenyl)-4-oxo-2-butenoate, sodium 2-(2,1,3-benzothiadiazol-5-yl)-3-(4-cyanobenzyl)-4-(4-methoxyphenyl)-4-oxo-2-butenoate, sodium 2-(2,1,3-benzothiadiazol-5-yl)-3-(4-methylbenzyl)-4-(4-methoxyphenyl)-4-oxo-2-butenoate, sodium 2-(2,1,3-benzothiadiazol-5-yl)-3-(3-methyl-4-methoxybenzyl)-4-(4-methoxyphenyl)-4-oxo-2-butenoate, sodium 2-(2,1,3-benzothiadiazol-5-yl)-3-(4-tert-butylbenzyl)--4-(4-methoxyphenyl)-4-oxo-2-butenoate, sodium 2-(2,1,3-benzothiadiazol-5-yl)-3-[(2-methoxycarbonylmethyloxy-4-methoxy)benzyl]-4-(4-methoxyphenyl)-4-oxo-2-butenoate, sodium 2-(2,1,3-benzothiadiazol-5-yl)-3-[(2-carboxymethyloxy-4-methoxy)benzyl]-4-(4-methoxyphenyl)-4-oxo-2-butenoate, sodium 2-(2,1,3-benzothiadiazol-5-yl)-3-(4-ethoxycarbonylbenzyl)-4-(4-methoxyphenyl)-4-oxo-2-butenoate, sodium 2-(2,1,3-benzothiadiazol-5-yl)-3-(4-benzyloxybenzyl)-4-(4-metboxyphenyl)-4-oxo-2-butenoate, sodium 2-(2,1,3-benzothiadiazol-5-yl)-3-(4-dimethylaminobenzyl)-4-(4-methoxyphenyl)-4-oxo-2-butenoate, sodium 2-(21,3-benzothiadiazol-5-yl)-3-(4-nitrobenzyl)-4-(4-methoxyphenyl)-4-oxo-2-butenoate, sodium 2-(2,1,3-benzothiadiazol-5-yl)-3-[(1,3-benzodioxol-5-yl)methyl]-4-(4-methoxyphenyl)-4-oxo-2-butenoate, sodium 2-(2,1,3-benzothiadiazol-5-yl)-3-(3-fluoro-4-methoxybenzyl)-4-(4-methoxyphenyl)-4-oxo-2-butenoate, sodium 2-(2,1,3-benzothiadiazol-5-yl)-3-[3-(N,N-dimethylamino)benzyl]-4-(4-methoxyphenyl)-4-oxo-2-butenoate, sodium 2-(2,1,3-benzothiadiazol-5-yl)-3-cyclohexylmethyl-4-(4-methoxyphenyl)-4-oxo-2-butenoate, sodium 2-(2,1,3-benzothiadiazol-5-yl)-3-cyclopentylmethyl-4-(4-methoxyphenyl)-4-oxo-2-butenoate, sodium 2-(2,1,3-benzothiadiazol-5-yl)-3-benzyl-4-(1,4-benzodioxan-6-yl)-4-oxo-2-butenoate, FAB 481 sodium 2-(2,1,3-benzothiadiazol-5-yl)-3-(2-methoxybenzyl)-4-(1,4-benzodioxan-6-yl)-4-oxo-2-butenoate, sodium 2-(2,1,3-benzothiadiazol-5-yl)-3-(3-methoxybenzyl)-4-(1,4-benzodioxan-6-yl)-4-oxo-2-butenoate, sodium 2-(2,1,3-benzothiadiazol-5-yl)-3-(4-methoxybenzyl)-4-(1,4-benzodioxan-6-yl)-4-oxo-2-butenoate, sodium 2-(2,1,3-benzothiadiazol-5-yl)-3-(3,4-dimethoxybenzyl)-4-(1,4-benzodioxan-6-yl)-4-oxo-2-butenoate, sodium 2-(2,1,3-benzothiadiazol-5-yl)-3-(3,4,6-trimethoxybenzyl)-4-(1,4-benzodioxan-6-yl)-4-oxo-2-butenoate, m.p. 76° sodium 2-(2,1,3-benzothiadiazol-5-yl)-3-(3,4-diisopropoxy-5-methoxybenzyl)-4-(1,4-benzodioxan-6-yl)-4-oxo-2-butenoate, m.p. 70° sodium 2-(2,1,3-benzothiadiazol-5-yl)-3-(3,4,5-triisopropoxybenzyl)-4-(1,4-benzodioxan-6-yl)-4-oxo-2-butenoate, sodium 2-(2,1,3-benzothiadiazol-5-yl)-3-(4-trifluoromethylbenzyl)-4-(1,4-benzodioxan-6-yl)-4-oxo-2-butenoate, sodium 2-(2,1,3-benzothiadiazol-5-yl)-3-(4-cyanobenzyl)-4-(1,4-benzodioxan-6-yl)-4-oxo-2-butenoate, sodium 2-(2,1,3-benzothiadiazol-5-yl)-3-(4-methylbenzyl)-4-(1,4-benzodioxan-6-yl)-4-oxo-2-butehoate, sodium 2-(2,1,3-benzothiadiazol-5-yl)-3-(3-methyl-4-methoxybenzyl)-4-(1,4-benzodioxan-6-yl)-4-oxo-2-butenoate, sodium 2-(2,1,3-benzothiadiazol-5-yl)-3-(4-tert-butylbenzyl)-4-(1,4-benzodioxan-6-yl)-4-oxo-2-butenoate, sodium 2-(2,1,3-benzothiadiazol-5-yl)-3-[(2-methoxycarbonylmethyloxy-4-methoxy)benzyl]-4-(1,4-benzodioxan-6-yl)-4-oxo-2-butenoate, sodium 2-(2,1,3-benzothiadiazol-5-yl)-3-[(2-carboxymethyloxy-4-methoxy)benzyl]-4-(1,4-benzodioxan-6-yl)-4-oxo-2-butenoate, sodium 2-(2,1,3-benzothiadiazol-5-yl)-3-(4-ethoxycarbonylbenzyl)-4-(1,4-benzodioxan-6-yl)-4-oxo-2-butenoate, sodium 2-(2,1,3-benzothiadiazol-5-yl)-3-(4-benzyloxybenzyl)-4-(1,4-benzodioxaz-6-yl)-4-oxo-2-butenoate, sodium 2-(2,1,3-benzothiadiazol-5-yl)-3-(4-dimethylaminobenzyl)-5-hydroxy-5-(1,4-benzodioxan-6-yl)-4-oxo-2-butenoate, sodium 2-(2,1,3-benzothiadiazol-5-yl)-3-(4-nitrobenzyl)-4-(1,4-benzodioxan-6-yl)-4-oxo-2-butenoate, sodium 2-(2,1,3-benzothiadiazol-5-yl)-3-[(1,3-benzodioxol-5-yl)methyl]-4-(1,4-benzodioxan-6-yl)-4-oxo-2-butenoate, sodium 2-(2,1,3-benzothiadiazol-5-yl)-3-(3-fluoro-4-methoxybenzyl)-4-(1,4-benzodioxan-6-yl)-4-oxo-2-butenoate, sodium 2-(2,1,3-benzothiadiazol-5-yl)-3-[3-(N,N-dimethylamino)benzyl]-4-(1,4-benzodioxan-6-yl)-4-oxo-2-butenoate, sodium 2-(2,1,3-benzothiadiazol-5-yl)-3-(cyclohexylmethyl)-4-(1,4-benzodioxan-6-yl)-4-oxo-2-butenoate [sic], sodium 2-(2,1,3-benzothiadiazol-5-yl)-3-(cyclopentylmethyl)-4-(1,4-benzodioxan-6-yl)-4-oxo-2-butencate [sic].

Sodium 2-(2,1,3-benzothiadiazol-5-yl)-3-benzyl-4-(4-methylphenyl)-4-oxo-2-butenoate, sodium 2-(2,1,3-benzothiadiazol-5-yl)-3-(2-methoxybenzyl)-4-(4-methylphenyl)-4-oxo-2-butenoate, sodium 2-(2,1,3-benzothiadiazol-5-yl)-3-(3-methoxybenzyl)-4-(4-methylphenyl)-4-oxo-2-butenoate, sodium 2-(2,1,3-benzothiadiazol-5-yl)-3-(4-methoxybenzyl)-4-(4-methylphenyl)-4-oxo-2-butenoate, sodium 2-(2,1,3-benzothiadiazol-5-yl)-3-(3,4-dimethoxybenzyl)-4-(4-methylphenyl)-4-oxo-2-butenoate, sodium 2-(2,1,3-benzothiadiazol-5-yl)-3-(3,4,5-trimethoxybenzyl)-4-(4-methylphenyl)-4-oxo-2-butenoate, sodium 2-(2,1,3-benzothiadiazol-5-yl)-3-(3,4-diisopropoxy-5-methoxybenzyl)-4-(4-methylphenyl)-4-oxo-2-butenoate, sodium 2-(2,1,3-benzothiadiazol-5-yl)-3-(3,4,5-triisopropoxybenzyl)-4-(4-methylphenyl)-4-oxo-2-butenoate, sodium 2-(2,1,3-benzothiadiazol-5-yl)-3-(4-trifluoromethylbenzyl)-5-hydroxy-5-(4-methylphenyl)-4-oxo-2-butenoate, sodium 2-(2,1,3-benzothiadiazol-5-yl)-3-(4-cyanobenzyl)-4-(4-methylphenyl)-4-oxo-2-butenoate, sodium 2-(2,1,3-benzothiadiazol-5-yl)-3-(4-methylbenzyl)-4-(4-methylphenyl)-4-oxo-2-butenoate, sodium 2-(2,1,3-benzothiadiazol-5-yl)-3-(3-methyl-4-methoxybenzyl)-4-(4-methylphenyl)-4-oxo-2-butenoate, sodium 2-(2,1,3-benzothiadiazol-5-yl)-3-(4-tert-butylbenzyl)-4-(4-methylphenyl)-4-oxo-2-butenoate, sodium 2-(2,1,3-benzothiadiazol-5-yl)-3-[(2-methoxycarbonylmethyloxy-4-methoxy)benzyl]-4-(4-methylphenyl)-4-oxo-2-butenoate, sodium 2-(2,1,3-benzothiadiazol-5-3-[(2-carboxymethyloxy-4-methoxy)benzyl]-4-(4-methylphenyl)-4-oxo-2-butenoate, sodium 2-(2,1,3-benzothiadiazol-5-yl)-3-(4-ethoxycarbonylbenzyl)-4-(4-methylphenyl)-4-oxo-2-butenoate, sodium 2-(2,1,3-benzothiadiazol-5-yl)-3-(4-benzyloxybenzyl)-4-(4-methylphenyl)-4-oxo-2-butenoate, sodium 2-(2,1,3-benzothiadiazol-5-yl)-3-(4-dimethylaminobenzyl)-4-(4-methylphenyl)-4-oxo-2-butenoate, sodium 2-(2,1,3-benzothiadiazol-5-yl)-3-(4-nitrobenzyl)-4-(4-methylphenyl)-4-oxo-2-butenoate, sodium 2-(2,1,3-benzothiadiazol-5-yl)-3-[(1,3-benzodioxol-5-yl)methyl]-4-(4-methylphenyl)-4-oxo-2-butenoate, sodium 2-(2,1,3-benzothiadiazol-5-yl)-3-(3-fluoro-4-methoxybenzyl)-4-(4-methylphenyl)-4-oxo-2-butenoate, sodium 2-(2,1,3-benzothiadiazol-5-yl)-3-[3-(N,N-dimethylamino)benzyl]-4-(4-methylphenyl)-4-oxo-2-butenoate, sodium 2-(2,1,3-benzothiadiazol-5-yl)-3-(cyclohexylmethyl)-4-(4-methylphenyl)-4-oxo-2-butenoate [sic] and sodium 2-(2,1,3-benzothiadiazol-5-yl)-3-(cyclopentylmethyl)-4-(4-methylphenyl)-4-oxo-2-butenoate [sic].

Sodium 2-(2,1,3-benzothiadiazol-5-yl)-3-benzyl-4-phenyl-4-oxo-2-butenoate, sodium 2-(2,1,3-benzothiadiazol-5-yl)-3-(2-methoxybenzyl)-4-phenyl-4-oxo-2-butenoate, sodium 2-(2,1,3-benzothiadiazol-5-yl)-3-(3-methoxybenzyl)-4-phenyl-4-oxo-2-butenoate, sodium 2-(2,1,3-benzothiadiazol-5-yl)-3-(4-methoxybenzyl)-4-phenyl-4-oxo-2-butenoate, sodium 2-(2,1,3-benzothiadiazol-5-yl)-3-(3,4-dimethoxybenzyl)-4-phenyl-4-oxo-2-butenoate, sodium 2-(2,1,3-benzothiadiazol-5-yl)-3-(3,4,5-trimethoxybenzyl)-4-phenyl-4-oxo-2-butenoate, sodium 2-(2,1,3-benzothiadiazol-5-yl)-3-(3,4-diisopropoxy-5-rethoxybenzyl)-4-phenyl-4-oxo-2-butenoate, sodium 2-(2,1,3-benzothiadiazol-5-yl)-3-(3,4,5-triisopropoxybenzyl)-4-phenyl-4-oxo-2-butenoate, sodium 2-(2,1,3-benzothiadiazol-5-yl)-3-(4-trifluoromethylbenzyl)-5-hydroxy-5-phenyl-4-oxo-2-butenoate, sodium 2-(2,1,3-benzothiadiazol-5-yl)-3-(4-cyanobenzyl)-4-phenyl-4-oxo-2-butenoate, sodium 2-(2,1,3-benzothiadiazol-5-yl)-3-(4-methylbenzyl)-4-phenyl-4-oxo-2-butenoate, sodium 2-(2;1,3-benzothiadiazol-5-yl)-3-(3-methyl-4-methoxybenzyl)-4-phenyl-4-oxo-2-butenoate, sodium 2-(2,1,3-benzothiadiazol-5-yl)-3-(4-tert-butylbenzyl)-4-phenyl-4-oxo-2-butenoate, sodium 2-(2,1,3-benzothiadiazol-5-yl)-3-[(2-methoxycarbonylmethyloxy-4-methoxy) benzyl]-4-phenyl-4-oxo-2-butenoate, sodium 2-(2,1,3-benzothiadiazol-5-yl)-3-[(2-carboxymethyloxy-4-methoxy)benzyl]-4-phenyl-4-oxo-2-butenoate, sodium 2-(2,1,3-benzothiadiazol-5-yl)-3-(4-ethoxycarbonylbenzyl)-4-phenyl-4-oxo-2-butenoate, sodium 2-(2,1,3-benzothiadiazol-5-yl)-3-(4-benzyloxybenzyl)-4-phenyl-4-oxo-2-butenoate, sodium 2-(2,1,3-benzothiadiazol-5-yl)-3-(4-dimethylaminobenzyl)-4-phenyl-4-oxo-2-butenoate, sodium 2-(2,1,3-benzothiadiazol-5-yl)-3-(4-nitrobenzyl)-4-phenyl-4-oxo-2-butenoate, sodium 2-(2,1,3-benzothiadiazol-5-yl)-3-[(1,3-benzodioxol-5-yl)methyl]-4-phenyl-4-oxo-2-butenoate, sodium 2-(2,1,3-benzothiadiazol-5-yl)-3-(3-fluoro-4-methoxybenzyl)-4-phenyl-4-oxo-2-butenoate, sodium 2-(2,1,3-benzothiadiazol-5yl)-3-[3-(N,N-dimethylamino)benzyl]-4-phenyl-4-oxo-2-butenoate, sodium 2-(2,1,3-benzothiadiazol-5-yl)-3-(cyclohexylmethyl)-4-phenyl-4-oxo-2-butenoate [sic] and sodium 2-(2,1,3-benzothiadiazol-5-yl)-3-(cyclopentylmethyl)-4-phenyl-4-oxo-2-butenoate [sic].

Sodium 2-(2,1,3-benzothiadiazol-5-yl)-3-benzyl-4-(4-isopropoxyphenyl)-4-oxo-2-butenoate, sodium 2-(2,1,3-benzothiadiazol-5-yl)-3-(2-methoxybenzyl)-4-14-isopropoxyphenyl)-4-oxo-2-butenoate, sodium 2-(2,1,3-benzothiadiazol-5-yl)-3-(3-methoxybenzyl)-4-(4-isopropoxyphenyl)-4-oxo-2-butenoate, sodium 2-(2,1,3-benzothiadiazol-5-yl)-3-(4-methoxyberizyl)-4-(4-isopropoxyphenyl)-4-oxo-2-butenoate, sodium 2-(2,1,3-benzothiadiazol-5-yl)-3-(3,4-dimethoxybenzyl)-4-(4-isopropoxyphenyl)-4-oxo-2-butenoate, sodium 2-(2,1,3-benzothiadiazol-5-yl)-3-(3,4,5-trimethoxybenzyl)-4-(4-isopropoxyphenyl)-4-oxo-2-butenoate, sodium 2-(2,1,3-benzothiadiazol-5-yl)-3-(3,4-diisopropoxy-5-methoxybenzyl)-4-(4-isopropoxyphenyl)-4-oxo-2-butenoate, sodium 2-(2,1,3-benzothiadiazol-5-yl)-3-(3,4,5-triisopropoxybenzyl)-4-(4-isopropoxyphenyl)-4-oxo-2-butenoate, sodium 2-(2,1,3-benzothiadiazol-5-yl)-3-(4-trifluoromethylbenzyl)-5-hydroxy-5-(4-isopropoxyphenyl)-4-oxo-2-butenoate, sodium 2-(2,1,3-benzothiadiazol-5-yl)-3-(4-cyanobenzyl)-4-(4-isopropoxyphenyl)-4-oxo-2-butenoate, sodium 2-(2,1,3-benzothiadiazol-5-yl)-3-(4-methylbenzyl)-4-(4-isopropoxyphenyl)-4-oxo-2-butenoate, sodium 2-(2,1,3-benzothiadiazol-5-yl)-3-(3-methyl-4-methoxybenzyl)-4-(4-isopropoxyphenyl)-4-oxo-2-butenoate, sodium 2-(2,1,3-benzothiadiazol-5-yl)-3-(4-tert-butylbenzyl)-4-(4-isopropoxyphenyl)-4-oxo-2-butenoate, sodium 2-(2,1,3-benzothiadiazol-5-yl)-3[(2-methoxycarbonylmethyloxy-4-methoxy)benzyl]-4-(4-isopropoxyphenyl)-4-oxo-2-butenoate, sodium 2-(2,1,3-benzothiadiazol-5-yl)-3-[(2-carboxymethyloxy-4-methoxy)benzyl]-4-(4-isopropoxy-phenyl)-4-oxo-2-butenoate, sodium 2-(2,1,3-benzothiadiazol-5-yl)-3-(4-ethoxycarbonylbenzyl)-4-(4-isopropoxyphenyl)-4-oxo-2-butenoate, sodium 2-(2,1,3-benzothiadiazol-5-yl)-3-(4-benzyloxybenzyl)-4-(4-isopropoxyphenyl)-4-oxo-2-butenoate, sodium 2-(2,1,3-benzothiadiazol-5-yl)-3-(4-dimethylaminobenzyl)-4-(4-isopropoxyphenyl)-4-oxo-2-butenoate, sodium 2-(2,1,3-benzothiadiazol-5-yl)-3-(4-nitrobenzyl)-4-(4-isopropoxyphenyl)-4-oxo-2-buteroate, sodium 2-(2,1,3-benzothiadiazol-5-yl)-3-[(1,3-benzodioxol-5-yl)methyl]-4-(4-isopropoxyphenyl)-4-oxo-2-butenoate, sodium 2-(2,1,3-benzothiadiazol-5-yl)-3-(3-fluoro-4-methoxybenzyl)-4-(4-isopropoxyphenyl)-4-oxo-2-butenoate, sodium 2-(2,1,3-benzothiadiazol-5-yl)-3-[3-(N,N-dimethylamino)benzyl]-4-(4-isopropoxyphenyl)-4-oxo-2-butenoate, sodium -2-(2,1,3-benzothiadiazol-5-yl)-3-(cyclohexylmethyl)-4-(4-isopropoxyphenyl)-4-oxo-2-butenoate [sic] and sodium 2-(2,1,3-benzothiadiazol-5-yl)-3-(cyclopentylmethyl)-5-hydroxy-(4-isopropoxyphenyl)-4-oxo-2-butenoate [sic].

Sodium 2-(2,1,3-benzothiadiazol-5-yl)-3-benzyl-4-(4-benzyloxyphenyl)-4-oxo-2-butenoate, sodium 2-(2,1,3-benzothiadiazol-5-yl)-3-(2-methoxybenzyl)-4-(4-benzyloxyphenyl)-4-oxo-2-butenoate, sodium 2-(2,1,3-benzothiadiazol-5-yl)-3-(3-methoxybenzyl)-4-(4-benzyloxyphenyl)-4-oxo-2-butenoate, sodium 2-(2,1,3-benzothiadiazol-5-yl)-3-(4-methoxybenzyl)-4-(4-benzyloxyphenyl)-4-oxo-2-butenoate, sodium 2-(2,1,3-benzothiadiazol-5-yl)-3-(3,4-dimethoxybenzyl)-4-(4-benzyloxyphenyl)-4-oxo-2-butenoate, sodium 2-(2,1,3-benzothiadiazol-5-yl)-3-(3,4,5-trimethoxybenzyl)-4-(4-benzyloxyphenyl)-4-oxo-2-butenoate, sodium 2-(2,1,3-benzothiadiazol-5-yl)-3-(3,4-diisopropoxy-5-methoxybenzyl)-4-(4-benzyloxhenyl)-4-oxo-2-butenoate, sodium 2-(2,1,3-benzothiadiazol-5-yl)-3-(3,4,5-triisopropoxybenzyl)-4-(4-benzyloxphenyl)-4-oxo-2-butenoate, sodium 2-(2,1,3-benzothiadiazol-5-yl)-3-(4-trifluoromethylbenzyl)-5-hydroxy-5-(4-benzyloxyphenyl)-4-oxo-2-butenoate, sodium 2-(2,1,3-benzothiadiazol-5-yl)-3-(4-cyanobenzyl)-4-(4-benzyloxyphenyl)-4-oxo-2-butenoate, sodium 2-(2,1,3-benzothiadiazol-5-yl)-3-(4-methylbenzyl)-4-(4-benzyloyphenyl)-4-oxo-2-butenoate, sodium 2-(2,1,3-benzothiadiazol-5-yl)-3-(3-methyl-4-methoxybenzyl)-4-(4-benzyloxyphenyl)-4-oxo-2-butenoate, sodium 2-(2,1,3-benzothiadiazol-5-yl)-3-(4-tert-butylbenzyl)-4-(4-benzyloxyphenyl)-4-oxo-2-butenoate, sodium 2-(2,1,3-benzothiadiazol-5-yl)-3-[(2-methoxycarbonylmethyloxy-4-methoxy)benzyl]-4-(4-benzyloxyphenyl)-4-oxo-2-butenoate, sodium 2-(2,1,3-benzothiadiazol-5-yl)-3-[(2-carboxymethyloxy-4-methoxy)benzyl]-4-(4-benzyloxyphenyl)-4-oxo-2-butenoate, sodium 2-(2,1,3-benzothiadiazol-5-yl)-3-(4-ethoxycarbonylbenzyl)-4-(4-benzyloxyphenyl)-4-oxo-2-butenoate, sodium 2-(2,1,3-benzothiadiazol-5-yl)-3-(4-benzyloxybenzyl)-4-(4-benzyloxyphenyl)-4-oxo-2-butenoate, sodium 2-(2,1,3-benzothiadiazol-5-yl)-3-(4-dimethylaminobenzyl)-4-(4-benzyloxyphenyl)-4-oxo-2-butenoate, sodium 2-(2,1,3-benzothiadiazol-5-yl)-3-(4-nitrobenzyl)-4-(4-benzyloxyphenyl)-4-oxo-2-butenoate, sodium 2-(2,1,3-benzothiadiazol-5-yl)-3-[(1,3-benzodioxol-5-yl)methyl]-4-(4-benzyloxyphenyl)-4-oxo-2-butenoate, sodium 2-(2,1,3-benzothiadiazol-5-yl)-3-(3-fluoro-4-methoxybenzyl)-4-(4-benzyloxyphenyl)-4-oxo-2-butenoate, sodium 2-(2,1,3-benzothiadiazol-5-yl)-3-[3-(N,N-dimethylamino)benzyl]-4-(4-benzyloxyphenyl)-4-oxb-2-butenoate, sodium 2-(2,1,3-benzothiadiazol-5-yl)-3-(cyclohexylmethyl)-4-(4-benzyloxyphenyl)-4-oxo-2-butenoate [sic] and sodium 2-(2,1,3-benzothiadiazol-5-yl)-3-(cyclopentylmethyl)-5-hydroxy-(4-benzyloxyphenyl)-4-oxo-2-butenoate [sic ].

Sodium 2-(2,1,3-benzothiadiazol-5-yl)-3-benzyl-4-(3,4-dimethylphenyl)-4-oxo-2-butenoate, sodium 2-(2,1,3-benzothiadiazol-5-yl)-3-(2-methoxybenzyl)-4-(3,4-dimethylphenyl)-4-oxo-2-butenoate, sodium 2-(2,1,3-benzothiadiazol-5-yl)-3-(3-methoxybenzyl)-4-(3,4-dimethylphenyl)-4-oxo-2-butenoate, sodium 2-(2,1,3-benzothiadiazol-5-yl)-3-(4-methoxybenzyl)-4-(3,4-dimethylphenyl)-4-oxo-2-butenoate, sodium 2-(2,1,3-benzothiadiazol-5-yl)-3-(3,4-dimethoxybenzyl)-4-(3,4-dimethylphenyl)-4-oxo-2-butenoate, sodium 2-(2,1,3-benzothiadiazol-5-yl)-3-(3,4,5-trimethoxybenzyl)-4-(3,4-dimethylphenyl)-4-oxo-2-butenoate, sodium 2-(2,1,3-benzothiadiazol-5-yl)-3-(3,4-diisopropoxy-5-methoxybenzyl)-4-(3,4-dimethylphenyl)-4-oxo-2-butenoate, sodium 2-(2,1,3-benzothiadiazol-5-yl)-3-(3,4,5-triisopropoxybenzyl)-4-(3,4-dimethylphenyl)-4-oxo-2-butenoate, sodium 2-(2,1,3-benzothiadiazol-5-yl)-3-(4-trifluoromethylbenzyl)-5-hydroxy-5-(3,4-dimethylphenyl)-4-oxo-2-butenoate, sodium 2-(2,1,3-benzothiadiazol-5-yl)-3-(4-cyanobenzyl)-4-(3,4-dimethylphenyl)-4-oxo-2-butenoate, sodium 2-(2,1,3-benzothiadiazol-5-yl)-3-(4-methylbenzyl)-4-(3,4-dimethylphenyl)-4-oxo-2-butenoate, sodium 2-(2,1,3-benzothiadiazol-5-yl)-3-(3-methyl-4-methoxybenzyl)-4-(3,4-dimethylphenyl)-4-oxo-2-butenoate, sodium 2-(2,1,3-benzothiadiazol-5-yl)-3-(4-tert-butylbenzyl)-4-(3,4-dimethylphenyl)-4-oxo-2-butenoate, sodium 2-(2,1,3-benzothiadiazol-5-yl)-3-[(2-methoxycarbonylmethyloxy-4-methoxy)benzyl]-4-(3,4-dimethylphenyl)-4-oxo-2-butenoate, sodium 2-(2,1,3-benzothiadiazol-5-yl)-3-[(2-carboxymethyloxy-4-methoxy)benzyl]-4-(3,4-dimethylphenyl)-4-oxo-2-butenoate, sodium -2-(2,1,3-benzothiadiazol-5-yl)-3-(4-ethoxycarbonylbenzyl)-4-(3,4-dimethylphenyl)-4-oxo-2-butenoate, sodium 2-(2,1,3-benzothiadiazol-5-yl)-3-(4-benzyloxybenzyl)-4-(3,4-dimethylphenyl)-4-oxo-2-butenoate, sodium 2-(2,1,3-benzothiadiazol-5-yl)-3-(4-dimethylaminobenzyl)-4-(3,4-dimethylphenyl)-4-oxo-2-butenoate, sodium 2-(2,1,3-benzothiadiazol-5-yl)-3-(4-nitrobenzyl)-4-(3,4-dimethylphenyl)-4-oxo-2-butenoate, sodium 2-(2,1,3-benzothiadiazol-5-yl)-3-[(1,3-benzodioxol-5-yl)methyl]-4-(3,4-dimethylphenyl)-4-oxo-2-butenoate, sodium 2-(2,1,3-benzothiadiazol-5-yl)-3-(3-fluoro-4-methoxybenzyl)-4-(3,4-dimethylphenyl)-4-oxo-2-butenoate, sodium 2-(2,1,3-benzothiadiazol-5-yl)-3-[3-(N,N-dimethylamino)benzyl]-4-(3,4-dimethylphenyl)-4-oxo-2-butenoate, sodium 2-(2,1,3-benzothiadiazol-5-yl)-3-(cyclohexylmethyl)-4-(3,4-dimethylphenyl)-4-oxo-2-butenoate [sic] and sodium 2-(2,1,3-benzothiadiazol-5-yl)-3-(cyclopentylnethyl)-5-hydroxy-(3,4-dimethylphenyl)-4-oxo-2-butenoate [sic].

Sodium 2-(2,1,3-benzothiadiazol-5-yl)-3-benzyl-4-(1,3-benzodioxol-5-yl)-4-oxo-2-butenoate, sodium 2-(2,1,3-benzothiadiazol-5-yl)-3-(2-methoxybenzyl)-4-(1,3-benzodioxol-5-yl)-4,-oxo-2-butenoate, sodium 2-(2,1,3-benzothiadiazol-5-yl)-3-(3-methoxybenzyl)-4-(1,3-benzodioxol-5-yl)-4-oxo-2-butenoate, sodium 2-(2,1,3-benzothiadiazol-5-yl)-3-(4-methoxybenzyl)-4-(1,3-benzodioxol-5-yl)-4-oxo-2-butenoate, sodium 2-(2,1,3-benzothiadiazol-5-yl)-3-(3,4-dimethoxybenzyl)-4-(1,3-benzodioxol-5-yl)-4-oxo-2-butenoate, sodium 2-(2,1,3-benzothiadiazol-5-yl)-3-(3,4,5-trimethoxybenzyl)-4-(1,3-benzodioxol-5-yl)-4-oxo-2-butenoate, FAB 557 sodium 2-(2,1,3-benzothiadiazol-5-yl)-3-(3,4-diisopropoxy-5-methoxybenzyl)-4-(1,3-benzodioxol-5-yl)-4-oxo-2-butenoate, sodium 2-(2,1,3-benzothiadiazol-5-yl)-3-(3,4,5-triisopropoxybenzyl)-4-(1,3-benzodioxol-5-yl)-4-oxo-2-butenoate, sodium 2-(2,1,3-benzothiadiazol-5-yl)-3-(4-trifluoromethylbenzyl)-5-hydroxy-5-(1,3-benzodioxol-5-yl)-4-oxo-2-butenoate, sodium 2-(2,1,3-benzothiadiazol-5-yl)-3-(4-cyanobenzyl)-4-(1,3-benzodioxol-5-yl)-4-oxo-2-butenoate, sodium 2-(2,1,3-benzothiadiazol-5-yl)-3-(4-methylbenzyl)-4-(1,3-benzodioxol-5-yl)-4-oxo-2-butenoate, sodium 2-(2,1,3-benzothiadiazol-5-yl)-3-(3-methyl-4-methoxybenzyl)-4-(1,3-benzodioxol-5-yl)-4-oxo-2-butenoate, sodium 2-(2,1,3-benzothiadiazol-5-yl)-3-(4-tert-butylbenzyl)-4-(1,3-benzodioxol-5-yl)-4-oxo-2-butenoate, sodium 2-(2,1,3-benzothiadiazol-5-yl)-3-[(2-methoxycarbonylmethyloxy-4-methoxy)benzyl]-4-(1,3-benzodioxol-5-yl)-4-oxo-2-butenoate, sodium 2-(2,1,3-benzothiadiazol-5-yl)-3-[(2-carboxymethyloxy-4-methoxy)benzyl]-4-(1,3-benzodioxol-5-yl)-4-oxo-2-butenoate, sodium 2-(2,1,3-benzothiadiazol-5-yl)-3-(4-ethoxycarbonylbenzyl)-4-(1,3-benzodioxol-5-yl)-4-oxo-2-butenoate, sodium 2-(2,1,3-benzothiadiazol-5-yl)-3-(4-benzyloxybenzyl)-4-(1,3-benzodioxol-5-yl)-4-oxo-2-butenoate, sodium 2-(2,1,3-benzothiadiazol-5-yl)-3-(4-dimethylaminobenzyl)-4-(1,3-benzodioxol-5-yl)-4-oxo-2-butenoate, sodium 2-(2,1,3-benzothiadiazol-5-yl)-3-(4-nitrobenzyl)-4-(1,3-benzodioxol-5-yl)-4-oxo-2-butenoate, sodium 2-(2,1,3-benzothiadiazol-5-yl)-3-[(1,3-benzodioxol-5-yl)methyl]-4-(1,3-benzodioxol-5-yl)-4-oxo-2-butenoate, sodium 2-(2,1,3-benzothiadiazol-5-yl)-3-(3-fluoro-4-methoxybenzyl)-4-(1,3-benzodioxol-5-yl)-4-oxo-2-butenoate, sodium 2-(2,1,3-benzothiadiazol-5-yl)-3-[3-(N,N-dimethylamino)benzyl]-4-(1,3-benzodiox ol-5-yl)-4-oxo-2-butenoate, sodium 2-(2,1,3-benzothiadiazol-5-yl)-3-(cyclohexylmethyl)-4-(1,3-benzodioxol-5-yl)-4-oxo-2-butenoate [sic] and sodium 2-(2,1,3-benzothiadiazol-5-yl)-3-(cyclopentylmethyl)-5-hydroxy-(1,3-benzodioxol-5-yl)-4-oxo-2-butenoate [sic].

Sodium 2-(2,1,3-benzothiadiazol-5-yl)-3-benzyl-4-(3,4,5-trimethoxyphenyl)-4-oxo-2-butemoate, sodium 2-(2,1,3-benzothiadiazol-5-yl)-3-(2-methoxybenzyl)-4-(3,4,5-trimethoxyphenyl)-4-oxo-2-butenoate, sodium 2-(2,1,3-benzothiadiazol-5-yl)-3-(3-methoxybenzyl)-4-(3,4,5-trimethoxyphenyl)-4-oxo-2-butenoate, sodium 2-(2,1,3-benzothiadiazol-5-yl)-3-(4-methoxybenzyl)-4-(3,4,5-trimethoxyphenyl)-4-oxo-2-butenoate, sodium 2-(2,1,3-benzothiadiazol-5-yl)-3-3,4-dimethoxybenzyl)-4-(3,4,5-trimethoxyphenyl)-4-oxo-2-butenoate, sodium 2-(2,1,3-benzothiadiazol-5-yl)-3-(3,4,5-trimethoxybenzyl)-4-(3,4,5-trimethoxyphenyl)-4-oxo-2-butenoate, sodium 2-(2,1,3-benzothiadiazol-5-yl)-3-(3,4-diisopropoxy-5- methoxybenzyl)-4-(3,4,5-trimethoxyphenyl)-4-oxo-2-butenoate, sodium 2-(2,1,3-benzothiadiazol-5-yl)-3-(3,4,5-triisopropoxybenzyl)-4-(3,4,5-trimethoxyphenyl)-4-oxo-2-butenoate, sodium 2-(2,1,3-benzothiadiazol-5-yl)-3-(4-trifluoromethylbenzyl)-5-hydroxy-5-(3,4,5-trimethoxyphenyl)-4-oxo-2-butenoate, sodium 2-(2,1,3-benzothiadiazol-5-yl)-3-(4-cyanobenzyl)-4-(3,4,5-trimethoxyphenyl)-4-oxo-2-butenoate, sodium 2-(2,1,3-benzothiadiazol-5-yl)-3-(4-methylbenzyl)-4-(3,4,5-trimethoxyphenyl)-4-oxo-2-butenoate, sodium 2-(2,1,3-benzothiadiazol-5-yl)-3-(3-methyl-4-methoxybenzyl)-4-(3,4,5-trimethoxyphenyl)-4-oxo-2-butenoate, sodium 2-(2,1,3-benzothiadiazol-5-yl)-3-(4-tert-butylbenzyl)-4-(3,4,5-trimethoxyphenyl)-4-oxo-2-butenoate, sodium 2-(2,1,3-benzothiadiazol-5-yl)-3-[(2-methoxycarbonylmethyloxy-4-methoxy)benzyl]-4(3,4,5-trimethoxyphenyl)-4-oxo-2-butenoate, sodium 2-(2,1,3-benzothiadiazol-5-yl)-3-[(2-carboxymethyloxy-4-methoxy)benzyl]-4-(3,4,5-trimethoxhenyl)-4-oxo-2-butenoate, sodium 2-(2,1,3-benzothiadiazol-5-yl)-3-(4-methoxycarbonylbenzyl)-4-(3,4,5-trimethoxyphenyl)-4-oxo-2-butenoate, sodium 2-(2,1,3-benzothiadiazol-5-yl)-3-(4-benzyloxybenzyl)-4-(3,4,5-trimethoxyphenyl)-4-oxo-2-butenoate, sodium 2-(2,1,3-benzothiadiazol-5-yl)-3-(4-dimethylaminobenzyl)-4-(3,4,5-trimethoxyphenyl)-4-oxo-2-butenoate, sodium 2-(2,1,3-benzothiadiazol-5-yl)-3-(4-nitrobenzyl)-4-(3,4,5-trimethoxyphenyl)-4-oxo-2-butenoate, sodium 2-(2,1,3-benzothiadiazol-5-yl)-3-[(1,3-benzodioxol-5-yl)methyl]-4-(3,4,5-trimethoxyphenyl)-4-oxo-2-butenoate, sodium 2-(2,1,3-benzothiadiazol-5-yl)-3-(3-fluoro-4-methoxybenzyl)-4-(3,4,5-trimethoxyphanyl)-4-oxo-2-butenoate, sodium 2-(2,1,3-benzothiadiazol-5-yl)-3-[3-(N,N-dimethylamino)benzyl]-4-(3,4,5-trimethoxyphenyl)-4-oxo-2-butenoate, sodium 2-(2,1,3-benzothiadiazol-5-yl)-3-(cyclohexylmethyl)-4-(3,4,5-trimethoxyphenyl)-4-oxo-2-butenoate [sic] and sodium 2-(2,1,3-benzothiadiazol-5-yl)-3-(cyclopentylmethyl)-5-hydroxy-(3,4,5-trimethoxyphenyl)-4-oxo-2-butenoate [sic].

Sodium 2-(2,1,3-benzothiadiazol-5-yl)-3-benzyl-4-(3,4-dimethoxhenyl)-4-oxo-2-butenoate, sodium 2-(2,1,3-benzothiadiazol-5-yl)-3-(2-methoxybenzyl)-4-(3,4-dimethoxphenyl)-4-oxo-2-butenoate, sodium 2-(2,1,3-benzothiadiazol-5-yl)-3-(3-methoxybenzyl)-4-(3,4-dimethoxyphenyl)-4-oxo-2-butenoate, sodium 2-(2,1,3-benzothiadiazol-5-yl)-3-(4-methoxybenzyl)-4-(3,4-dimethoxyphenyl)-4-oxo-2-butenoate, sodium 2-(2,1,3-benzothiadiazol-5-yl)-3-(3,4-dimethoxybenzyl)-4-(3,4-dimethoxyphenyl)-4-oxo-2-butenoate, sodium 2-(2,1,3-benzothiadiazol-5-yl)-3-(3,4,5-trimethoxybenzyl)-4-(3,4-dimethoxyphenyl)-4-oxo-2-butenoate, sodium 2-(2,1,3-benzothiadiazol-5-yl)-3-(3,4-diisopropoxy-5-methoxybenzyl)-4-(3,4-dimethoxyphenyl)-4-oxo-2-butenoate, sodium 2-(2,1,3-benzothiadiazol-5-yl)-3-(3,4,5-triisopropoxybenzyl)-4-(3,4-dimethoxyphenyl)-4-oxo-2-butenoate, sodium 2-(2,1,3-benzothiadiazol-5-yl)-3-(4-trifluoromethylbenzyl)-5-hydroxy-5-(3,4-dimethoxyphenyl)-4-oxo-2-butenoate, sodium 2-(2,1,3-benzothiadiazol-5-yl)-3-(4-cyanobenzyl)-4-(3,4-dimethoxyphenyl)-4-oxo-2-butenoate, sodium 2-(2,1,3-benzothiadiazol-5-yl)-3-(4-methylbenzyl)-4-(3,4-dimethoxyphenyl)-4-oxo-2-butenoate, sodium 2-(2,1,3-benzothiadiazol-5-yl)-3-(3-methyl-4-methoxybenzyl)-4-(3,4-dimethoxyphenyl)-4-oxo-2-butenoate, sodium 2-(2,1,3-benzothiadiazol-5-yl)-3-(4-tert-butylbenzyl)-4-(3,4-dimethoxyphenyl)-4-oxo-2-butenoate, sodium 2-(2,1,3-benzothiadiazol-5-yl)-3-[(2-methoxycarbonylmethyloxy-4-methoxy)benzyl]-4-(3,4-dimethoxyphenyl)-4-oxo-2-butenoate.

sodium 2-(2,1,3-benzothiadiazol-5-yl)-3-[(2-carboxymethyloxy-4-methoxy)benzyl]-4-(3,4-dimethoxyphemyl)-4-oxo-2-butenoate, sodium 2-(2,1,3-benzothiadiazol-5-yl)-3-(4-methoxycarbonylbenzyl)-4-(3,4-dimethoxyphenyl)-4-oxo-2-butenoate, sodium 2-(2,1,3-benzothiadiazol-5-yl)-3-(4-benzyloxybenzyl)-4-(3,4-dimethoxyphenyl)-4-oxo-2-butenoate, sodium 2-(2,1,3-benzothiadiazol-5-yl)-3-(4-dimethylaminobenzyl)-4-(3,4-dimethoxyphenyl)-4-oxo-2-butenoate, sodium 2-(2,1,3-benzothiadiazol-5-yl)-3-(4-nitrobenzyl)-4-(3,4-dimethoxyphenyl)-4-oxo-2-butenoate, sodium 2-(2,1,3-benzothiadiazol-5-yl)-3-[(1,3-benzodioxol-5-yl)methyl]-4-(3,4-dimethocxyphenyl)-4-oxo-2-butenoate, sodium 2-(2,1,3-benzothiadiazol-5-yl)-3-(3-fluoro-4-methoxybenzyl)-4-(3,4-dimethoxyphenyl)-4-oxo-1-2-butenoate, sodium 2-(2,1,3-benzothiadiazol-5-yl)-3-[3-(N,N-dimethylamino)benzyl]-4-(3,4-dimethoxyphenyl)-4-oxo-2-butenoate, sodium 2-(2,1,3-benzothiadiazol-5-yl)-3-(cyclohexylmethyl)-4-(3,4-dimethoxyphenyl)-4-oxo-2-butenoate [sic] and sodium 2-(2,1,3-benzothiadiazol-5-yl)-3-(cyclopentylmethyl)-5-(3,4-dimethoxyphenyl)-4-oxo-2-butenoate [sic].

Sodium 2-(2,1,3-benzothiadiazol-5-yl)-3-benzy-4-(4-methylthiophenyl)-4-oxo-2-butenoate, sodium 2-(2,1,3-benzothiadiazol-5-yl)-3-(2-methoxybenzyl)-4-(4-methylthiophenyl)-4-oxo-2-butenoate, sodium 2-(2,1,3-benzothiadiazol-5-yl)-3-(3-methoxybenzyl)-4-(4-methylthiophenyl)-4-oxo-2-butenoate, sodium 2-(2,1,3-benzothiadiazol-5-yl)-3-(4-methoxybenzyl)-4-(4-methylthiophenyl)-4-oxo-2-butenoate, sodium 2-(2,1,3-benzothiadiazol-5-yl)-3-(3,4-dimethoxybenzyl)-4-(4-methylthiophenyl)-4-oxo-2-butenoate, sodium 2-(2,1,3-benzothiadiazol-5-yl)-3-(3,4,5-trimethoxybenzyl)-4-(4-methylthiophenyl)-4-oxo-2-butenoate, sodium 2-(2,1,3-benzothiadiazol-5-yl)-3-(3,4,-diisopropoxy-5-methoxybenzyl)-4-(4-methylthiophenyl)-4-oxo-2-butenoate, sodium 2-(2,1,3-benzothiadiazol-5-yl)-3-(3,4,5-triisopropoxybenzyl)-4-(4-methylthiophenyl)-4-oxo-2-butenoate,
sodium 2-(2,1,3-benzothiadiazol-5-yl)-3-(4-trifluoromethylbenzyl)-5hdroxy-5-(4-methylthiophenyl)-4-oxo-2-butenoate,
sodium 2-(2,1,3-benzothiadiazol-5-yl)-3-(4-cyanobenzyl)-4-(4-methylthiophenyl)-4-oxo-2-butenoate,
sodium 2-(2,1,3-benzothiadiazol-5-yl)-3-(4-methylbenzyl)-4-(4-methylthiophenyl)-4-oxo-2-butenoate,
sodium 2-(2,1,3-benzothiadiazol-5-yl)-3-(3-methyl-4-methoxybenzyl)-4-(4-methylthiophenyl)-4-oxo-2-butenoate,
sodium 2-(2,1,3-benzothiadiazol-5-yl)-3-(4-tert-butylbenzyl)-4-(4-methylthiophenyl)-4-oxo-2-butenoate,
sodium 2-(2,1,3-benzothiadiazol-5-yl)-3-[(2-methoxycarbonylmethyloxy-4-methoxy)benzyl]-4-(4-methylthiophenyl)-4-oxo-2-butenoate,
sodium 2-(2,1,3-benzothiadiazol-5-yl)-3-[(2-carboxymethyloxy-4-methoxy)benzy]-4-4-methylthiophenyl)-4-oxo-2-butenoate,
sodium 2-(2,1,3-benzothiadiazol-5-yl)-3-(4-ethoxycarbonylbenzyl)-4-(4-methylthiophenyl)-4-oxo-2-butenoate,
sodium 2-(2,1,3-benzothiadiazol-5-yl)-3-(4-benzyloxybenzyl)-4-(4-methylthiophenyl)-4-oxo-2-butenoate,
sodium 2-(2,1,3-benzothiadiazol-5-yl)-3-(4-dimethylaminobenzyl)-4-(4-methylthiophenyl)-4-oxo-2-butenoate,
sodium 2-(2,1,3-benzothiadiazol-5-yl)-3-(4-nitrobenzyl)-4-(4-methylthiophenyl)-4-oxo-2-butenoate,
sodium 2-(2,1,3-benzothiadiazol-5-yl)-3-[(1,3-benzodioxol-5-yl)methyl]-4-(4-methylthiophenyl)-4-oxo-2-butenoate,
sodium 2-(2,1,3-benzothiadiazol-5-yl)-3-(3-fluoro-4-methoxybenzyl)-4-(4-methylthiophenyl)-4-oxo-2-butenoate,
sodium 2-(2,1,3-benzothiadiazol-5-yl)-3-[3-(N,N-dimethylamino)benzyl]-4-(4-methylthiophenyl)-4-oxo-2-butenrate,
sodium 2-(2,1,3-benzothiadiazol-5-yl)-3-(cyclohexylmethyl)-4-(4-methylthiophenyl)-4-oxo-2-butenoate [sic ] and
sodium 2-(2,1,3-benzothiadiazol-5-yl)-3-(cyclopentylmethyl)-5-hydroxy-(4-methylthiopheayl)-4-oxo-2-butenoate [sic].
Sodium 2-(2,1,3-benzoxadiazol-5-yl)-3-benzyl-4-(4-methoxyphenyl)-4-oxo-2-butenoate,
sodium 2-(2,1,3-benzoxadiazol-5-yl)-3-(2-methoxybenzyl)-4-(4-methoxyphenyl)-4-oxo-2-butenoate,
sodium 2-(2,1,3-benzoxadiazol-5-yl)-3-(3-methoxybenzyl)-4-(4-methoxyphenyl)-4-oxo-2-butenoate,
sodium 2-(2,1,3-benzoxadiazol-5-yl)-3-(4-methoxybenzyl)-4-(4-methoxyphenyl)-4-oxo-2-butenoate,
sodium 2-(2,1,3-benzoxadiazol-5-yl)-3-(3,4-dimethoxybenzyl)-4-(4-methoxyphenyl)-4-oxo-2-butenoate,
sodium 2-(2,1,3-benzoxadiazol-5-yl)-3-(3,4,5-trimethoxybenzyl)-4-(4-methophenyl)-4-oxo-2-butenoate,
sodium 2-(2,1,3-benzoxadiazol-5-yl)-3-(3,4-diisopropoxy-5-methoxybenzyl)-4-(4-methoxyphenyl)-4-oxo-2-butenoate,
sodium 2-(2,1,3-benzoxadiazol-5-yl)-3-(3,4,5-triisopropoxybenzyl)-4-(4-methoxyphenyl)-4-oxo-2-butenoate,
sodium 2-(2,1,3-benzoxadiazol-5-yl)-3-(4-trifluoromethylbenzy)-5-hyroxy-5-(4-methoxyphenyl)-4-oxo-2-butenoate,
sodium 2-(2,1,3-benzoxadiazol-5-yl)-3-(4-cyanobenzyl)-4-(4-methoxyphenyl)-4-oxo-2-butenoate,
sodium 2-(2,1,3-benzoxadiazol-5-yl)-3-(4-methylbenzyl)-4-(4-methoxyphenyl)-4-oxo-2-butenate,
sodium 2-(2,1,3-benzoxadiazol-5-yl)-3-(3-methyl-4-methoxybenzyl)-4-(4-methoxhenyl)-4-oxo-2-butenoate,
sodium 2-(2,1,3-benzoxadiazol-5-yl)-3-(4-tert-butylbenzyl)-4-(4-methoxyphenyl)-4-oxo-2-butenoate,
sodium 2-(2,1,3-benzoxadiazol-5-yl)-3-[(2-methoxycarbonylmethyloxy-4-methoxy)benzyl]-4-(4-methoyphenyl)-4-oxo-2-butexioate,
sodium 2-(2,1,3-benzoxadiazol-5-yl)-3-[(2-carboxymethyloxy-4-methoxy)benzyl]-4-(4-methoxyphenyl)-4-oxo-2-butenoate,
sodium 2-(2,1,3-benzoxadiazol-5-yl)-3-(4-ethoxycarbonylbenzyl)-4-(4-methoxyphenyl)-4-oxo-2-butenoate,
sodium 2-(2,1,3-benzoxadiazol-5-yl)-3-(4-benzyloxybenzyl)-4-(4-methoxphenyl)-4-oxo-2-butenoate,
sodium 2-(2,1,3-benzoxadiazol-5-yl)-3-(4-dimethylaminobenzyl)-4-(4-methoxyphenyl)-4-oxo-2-butenoate,
sodium 2-(2,1,3-benzoxadiazol5-yl)-3-(4-nitrobenzyl)-4-(4-methoxyphenyl)-4-oxo-2-butenoate,
sodium 2-(2,1,3-benzoxadiazol-5-yl)-3-[(1,3-benzodioxol-5-yl)methyl]-4-(4-methoxyphenyl)-4-oxo-2-butenoate,
sodium 2-(2,1,3-benzoxadiazol-5-yl)-3-(3-fluoro-4-methoxybenzyl)-4-(4-methoxyphenyl)-4-oxo-2-butenoate,
sodium 2-(2,1,3-benzoxadiazol-5-yl)-3-[3-(N,N-dimethylamino)benzyl]-4-(4-methoxyphenyl)-4-oxo-2-butenoate,
sodium 2-(2,1,3-benzoxadiazol-5-yl)-3-(cyclopentylmethyl)-4-(4-methoxyphenyl)-4-oxo-2-butenoate [sic] and
sodium 2-(2,1,3-benzoxadiazol-5-yl)-3-(cyclopentylmethyl)-4-(4-methoxyphenyl)-4-oxo-2-butenoate [sic].

EXAMPLE 3

0.38 g of benzaldehyde and 1.20 g of ethyl 4-(2,1,3-benzothiadiazol-5-yl)-2-(1,3-benzodioxol-5-yl)-4-oxo-butanoate ("B") is added to a solution of 80 mg of sodium in 5 ml of methanol and the mixture is heated under reflux for one hour. After addition of 5 ml of acetic acid, the mixture is heated for a futher 16 hours. The solvent is removed and worked up in the customary manner. 5-(2,1, 3-Benzothiadiazol-5-yl)-4-benzyl-5-hydroxy-3-(1,3-benzodioxol-5-yl)-5H-furan-2-one, amorphous, is obtained.

The following are obtained an analogously by reaction of "B"

with 4-methoxybenaldehyde
  5-(2,1,3-benzothidiazol-5-yl)-4-(4-methoxyphenylmethyl)-5-hydroxy-3-(1,3-benzodioxol-5-yl)-5H-furan-2-one,
with 3,4-dimethoxybenzaldehyde
  5-(2,1,3-benzothiadiazol-5-yl)-4-(3,4-dimethoxybenzyl)-5-hydroxy-3-(1,3-benzodioxol-5-yl)-5H-furan-2-one,
with 3,4,5-trimethoxybenzaldehyde
  5-(2,1,3-benzothioadiazol-5-yl)-4-(3,4,5-trimethoxybenzyl)-5-hydroxy-3-(1,3-benzodioxol-5-yl)-5H-furan-2-one,
with 3,4-diisopropoxy-5-methoxybenzaldehyde
  5-(2,1,3-benzothiadiazol-5-yl)-4-(3,4-diisopropoxy-5-methoxybenzyl)-5-hydroxy-3-(1,3-benzodioxol-5-yl)-5H-furan-2-one,
with 3,4,5-triisopropoxybenzaldehyde
  5-(2,1,3-benzothiadiazol-5-yl)-4-(3,4,5-triisopropoxybenzyl)-5-hydroxy-3-(1,3-benzodioxol-5-yl)-5H-furan-2-one,
with 4-chlorobenzaldehyde
  5-(2,1,3-benzothiadiazol-5-yl)-4-(4-chlorobenzyl)-5-hydroxy-3-(1,3-benzodioxol-5-yl)-5H-furan-2-one,
with 4-bronobenzaldehyde
  5-(2,1,3-benzothiadiazol-5-yl)-4-(4-bromobenzyl)-5-hydroxy-3-(1,3-benzodioxol-5-yl)-5H-furan-2-one,
with 4-trifluoromethylbenzaldehyde
  5-(2,1,3-benzothiadiazol-5-yl)-4-(4-trifluoromethylbenzyl)-5-hydroxy-3-(1,3-benzodioxol-5-yl)-5H-furan-2-one,
with 4-cyanobenzaldehyde
  5-(2,1,3-benzothiadiazol-5-yl)-4-(4-cyanobenzyl)-5-hydroxy-3-(1,3-benzodioxol-5-yl)-5H-furan-2-one,
with 4-methylbenzaldehyde
  5-(2,1,3-benzothiadiazol-5-yl)-4-(4-methylbenzyl)-5-hydroxy-3-(1,3-benzodioxol-5-yl)-5H-furan-2-one,
with 3-methyl-4-metoxybenzaldehyde
  5-(2,1,3-benzothiadiazol-5-yl)-4-(3-methyl-4-methoxybenzyl)-5-hydroxy-3-(1,3-benzodioxol-5-yl)-5H-furan-2-one,
with 4-tert-butylbenzaldehyde
  5-(2,1,3-benzothiadiazol-5-yl)-4-(4-tert-butylbenzyl)-5-hydroxy-3-(1,3-benzodioxol-5-yl)-5H-furan-2-one,
with (2-methoxycarbonylmethyloxy-4-methoxy)benzaldehyde
  5-(2,1,3-benzothiadiazol-5-yl)-4-[(2-methoxycarbonylmethyloxy-4-methoxy)benzyl]-5-hydroxy-3-(1,3-benzodioxol-5-yl)-5H-furan-2-one,
with (2-carboxethyloxy-4-methoxy)benzaldehyde
  5-(2,1,3-benzothiadiazol-5-yl)-4-[(2-carboxymethyloxy-4-methoxy)benzyl]-5-hydroxy-3-1,3-benzodioxol-5-yl)-5H-furan-2-one,
with 4-methoycarbonylbenzaldehyde
  5-(2,1,3-benzothiadiazol-5-yl)-4-(4-ethoxycarbonylbenzyl)-5-hydroxy-3-(1,3-benzodioxol-5-yl)-5H-furan-2-one,
with 4-methanesulfonylbenzaldehyde
  5-(2,1,3-benzothiadiazol-5-yl)-4-(4-methanesulfonylbenzyl)-5-hydroxy-3-(1,3-benzodioxol-5-yl)-5H-furan-2-one,
with 4-benzyloxybenaldehyde
  5-(2,1,3-benzothiadiazol-5-yl)-4-(4-benzyloxybenzyl)-5-hydroxy-3-(1,3-benzodioxol-5-yl) 5-furan-2-one,
with 4-dimethylaminobenzaldehyde
  5(2,1,3-benzothiadiazol-5-yl)-4-(4-dimethylaminobenzyl)-5-hydroxy-3-(1,3-benzodioxol-5-yl)-5H-furan-2-one,
with 4-nitrobenzaldehyde
  5-(2,1,3-benzothiadiazol-5-yl)-4-(4-nitrobenzyl)-5-hydroxy-3-(1,3-benzodioxol-5-yl)-5H-furan-2-one,
with 4-formylbenzadehyle
  5-(2,1,3-benziothiadiazol-5-yl)-4-(4-formylbenzyl)-5-hydroxy-3-(1,3-benzodioxyl-5-yl)-5H-furan-2-one,
with (2,1,3-benzodioxol-5-yl)carbaldehyde
  5-(2,1,3-benzothiadiazol-5-yl)-4-1(1,3-benzodioxol-5-yl)methyl]-5-hydroxy-3-(1,3-benzodioxol-5yl)-5H-furan-2-one,
with 2-(1,3-benzodioxol-5-yloxy)benzaldehyde
  5-(2,1,3-benzothiadiazol-5-yl)-4-[2-(1,3-benzodioxol-5-yloxy)benzyl]-5-hydroxy-3-(1,3-benzodioxol-5-yl)-5H-furan-2-one,
with cyclohexanecarbaldehyde
  5-(2,1,3-benzothiadiazol-5-yl)-4-cyclohexylmethyl-5-hydroxy-3-(1,3-benzodioxol-5-yl)-5H-furan-2-one and
with cyclopentanecarbaldehyde
  5-(2,1,3-benzothiadiazol-5-yl)-4-cyclopentylmethyl-5-hydroxy-3-(1,3-benzodioxol-5-yl)-5H-furan-2-one.

EXAMPLE 4

0.5 g of (2,1,3-benzothiadiazol-5-yl) carbaldehyde ("C") and 1.20 g of ethyl 2-(1,3-benzodioxol-5-yl)-3-(4-methoxyphenyl)-4-oxo-butanoate are added to a solution of 80 mg of sodium in 5 ml of methanol and the mixture is heated under reflux for one hour. After addition of 5 ml of acetic acid, it is heated for a further 16 hours. The solvent is removed and the residue is worked up in the customary manner. 4-(2,1,3-Benzothiadiazol-5ylmethyl)-3-(1,3-benzodioxol-5-yl)-5-hydroxy-5-(methoxyphenyl)-5H-furan-2-one, m.p. 172°, is obtained.

The following are obtained analogously by reaction of "C"

with ethyl 2-(1,3-benzodioxol-5-yl)-3-(3,4-dimethoxyphenyl)-4-oxobutanoate
  4-(2,1,3-benzothiadiazol-5-ylmethyl)-3-(1,3-benzodioxol-5-yl)-5-hydroxy-5-(3,4-dimethoahenyl)-5H-2 furan-2-one,
with ethyl 2-(1,3-benzodioxol-5-yl)-3-(3,4,5-trimethoxyphenyl)-4-oxobutanoate
  4-(2,1,3-benzothiadiazol-5-ylmethyl)-3-(1,3-benzodioxol-5-yl)-5-hydroxy-5-(3,4,5-trimethoxyphenyl)-5H-furan-2-one,
with ethyl 2-(1,3-benzodioxol-5-yl)-3-(3,4-diisopropoxy-5-methoxyphenyl)-4-oxobutanoate
  4-(2,1,3-benzothiadiazol-5-ylmethyl)-3-(1,3-benzodioxol-5-yl)-5-hydroxy-5-(3,4-diisopropoxy-5-methoxyphenyl)-5H-furan-2-one,
with ethyl 2-(1,3-benzodioxol-5-yl)-3-(3,4,5-triisopropoxyphenyl)-4-oxobutanoate
  4-(2,1,3-benzothiadiazol-5-ylmethyl)-3-(1,3-benzodixol-5-yl)-5-hydroxy-5-(3,4,5-triisopropoxy)-5H-furan-2-one,
with ethyl 2-(1,3-benzodioxol-5-yl)-3-(4-chlorophenyl)-4-oxobutanoate
  4-(2,1,3-benzothiadiazol-5-ylmethyl)-3-(1,3-benzodioxol-5-yl)-5-hydroxy-5-(4-chlorophenyl)-5H-furan-2-one, with ethyl 2-(1,3-benzodioxol-5-yl)-3-(4-bromophenyl)-4-oxobutanoate
  4-(2,1,3-benzothiadiazol-5-ylmethyl)-3-(1,3-benzodioxol-5-yl)-5-hydroxy-5-(4-bromophenyl)-5H-furan-2-one,
with ethyl 2-(1,3-benzodioxol-5-yl)-1,3-(4-trifluoromethylphenyl)-4-oxobutanoate
  4-(2,1,3-benzothiadiazol-5-ylmethyl)-3-(1,3-benzodioxol-5-yl)-5-hydroxy-5-(4-trifluoromethylphenyl)-5H-furan-2-one,
with ethyl 2-(1,3-benzodioxol-5-yl)-3-(4-cyanophenyl)-4-oxobutanoate
  4-(2,1,3-benzothiadiazol-5-ylmethyl)-3-(1,3-benzodioxol-5-yl)-5-hydroxy-5-(4-cyanophenyl)-5H-furan-2-one,
with ethyl 2-(1,3-benzodioxol-5-yl)-3-(4-methylphenyl)-4-oxobutanaoate
  4-(2,1,3-benzothiadiazol-5-ylmethyl)-3-(1,3-benzodioxol-5-yl)-5-hydroxy-5-(4-methylphenyl)-5H-furan-2-one,
with ethyl 2-(1,3-benzodioxol-5-yl)-3-(3-methyl-4-methoxyphenyl)-4-oxobutanoate
  4-(2,1,3-benzothiadiazol-5-ylmethyl)-3-(1,3-benzodioxol-5-yl)-5-hydroxy-5-(3-methyl-4-methoxyphenyl)-5H-furan-2-one,
with ethyl 2-(1,3-benzodioxol-5-yl)-3-(4-tert-butylphenyl)-4-oxobutanoate
  4-(2,1,3-benzothiadiazol-5-ylmethyl)-3-(1,3-benzodioxol-5-yl)-5-hydroxy-5-(4-tert-butylphenyl)-5H-furan-2-one,
with ethyl 2-(1,3-banzodioxol-5-yl)-3-[(2-methoxycarbonylmethyloxy-4-methoxy)phenyl]-4-oxobutanoate
  4-(2,1,3-benzothiadiazol-5-ylmethyl)-3-(1,3-benzodioxol-5-yl)-5-hydroxy-5-[(2-methoxycarbonylmethyloxy-4-methoxy)phenyl]-5H-furan-2-one,
with ethyl 2-(1,3-benzodioxol-5-yl)-3-[(2-carboxymethyloxy-4-methoxy)phenyl]-4-oxobutanoate
  4-(2,1,3-benzothiadiazol-5-ylmethyl)-3-(1,3-benzodioxol-5-yl)-5-hyroxy-5-[(2-carboxymethyloxy-4-methoxy)phenyl]-5H-furan-2-one,
with ethyl 2-(1,3-benzodioxol-5-yl)-3-(4-ethoxycarbonylphenyl)-4-oxobutanoate
  4-(2,1,3-benzothiadiazol-5-ylmethyl)-3-(1,3-benzodioxol-5-yl)-5-hydroxy-5-(4-ethoxycarbonylphenyl)-5H-furan-2-one,
with ethyl 2-(2,1,3-benzodioxol-5-yl)-3-(4-methanesulfonylphenyl)-4-oxobutanoate
  4-(2,1,3-benzothiadiazol-5-ylmethyl)-3-(1,3-benzodioxol-5-yl)-5-hydroxy-5-(4-methanesulfonylphenyl)-5H-furan-2-one,
with ethyl 2-(1,3-benzodioxol-5-yl)-3-(4-benzyloxyphenyl)-4-oxobutanoate
  4-(2,1,3-benztothiadiazol-5-ylmethyl)-3-(1,3-benzodioxol-5-yl)-5-hydroxy-5-(4-benzyloxphenyl)-5H-furan-2-one,
with ethyl 2-(1,3-benzodioxol-5-yl)-3-(4-dimethylaminophenyl)-4-oxobutanoate
  4-(2,1,3-benzothiadiazol-5-ylmethyl)-3-(1,3-benzodioxol-5-yl)-5-hydroxy-5-(4-dimethylaminophenyl)-5H-furan-2-one,
with ethyl 2-(1,3-benzodioxol-5-yl)-3-(4-nitrophenyl)-4-oxobutancate
  4-(2,1,3-benzothiadiazol-5-ylmethyl)-3-(1,3-benzodioxol-5-yl)-5-hydroxy-5-(4-nitrophenyl)-5H-furan-2-one and with ethyl 2-(1,3-benzodioxol-5-yl)-3-(4-formylphenyl)-4-oxobutanoate
  4-(2,1,3-benzothiadiazol-5-ylmethyl)-3-(1,3-benzodioxol-5-yl)-5-hydroxy-5-(4-formylphenyl)-5H-furan-2-one.

EXAMPLE 5

A solution of 1 g of 3-(2,1,3-benzothiadiazol-5-yl)-4-(4-nitrobenzyl)-5-hydroxy-5-(4-methoxyphenyl)-5H-furan-2-one in 25 ml of methanol is hydrogenated to completion at normal pressure and 20° on 1 g of Raney nickel. The mixture is filtered, the solvent is removed and 3-(2,1,3-benzothiaaiazol-5-yl)-4-(4-aminobenzyl)-5-hydroxy-5-(4-methyhenyl)-5H-furan-2-one is obtained.

EXAMPLE 6

By reaction with equimolar amounts of acetyl chloride in pyridine. and catalytic a mounts of dimethylaminopyridine, starting from 3-(2,1,3-benzothiadiazol-5-yl)-4-(4-aminobenzyl)-5-hydroxy-5-(4-methoxyphenyl)-5H-furan-2-one
  3-(2,1,3-benzothiadiazol-5-yl)-4-(4-acetamidobenzyl)-5-hydroxy-5-(4-methoxyphenyl)-5H-furan-2-one is obtained.

EXAMPLE 7

By reaction with equimolar amounts of phenyl isocyanate in dichloromethane,
starting from 3-(2,1,3-benzothiediazol-5-yl)-4-(4-aminobenzyl)-5-hydroxy-5-(4-methoxyphenyl)-5H-furan-2-one
  3-(2,1,3-benzothiadiazol-5-yl)-4-[4-(phenylureido)benzyl]-5-hydroxy-5-(4-nethoxyphenyl)-5H-furan-2-one is obtained.

EXAMPLE 8

By reaction with equimolar amounts of butyl isocyanate in dichloromethane,
starting from 3-(2,1,3-benzothiadiazol-5-yl)-4-(4-aminobenzyl)-5-hydroxy-5-(4-methoxyphenyl)-5H-furan-2-one
  3-(2,1,3-benzothiadiazol-5-yl)-4-[4-(butylureido)benzyl]-5-hydroxy-5-(4-methoxypheyl)-5-furan-2-one is obtained.

EXAMPLE 9

By reaction with equimolar amounts of butyl iodide in THF,
starting from 3-(2,1,3-benzothiadiazol-5-yl)-4-(4-acetamidobenzyl)-5-hydroxy-5-(4-methoxyphenyl)-5H-furan-2-one
  3-(2,1,3-benzothiadiazol-5-yl)-4-[4-(N-butylacetamido)benzyl]-5-hydroxy-5-(4-methoxhenyl)-5H-furan-2-one is obtained.

EXAMPLE 10

By reaction with equimolar amounts of butylsulfonyl chloride and caesium carbonate in DMF,
starting from 3-(2,1,3-benzothiadiazol-5-yl)-4-(4-aminobenzyl)-5-hydroxy-5-(4-methoxyphenyl)-5H-7furan-2-one
  3-(2,1,3-benzothiadiazol-5-yl)-4-[4-(butylsulfonamido)benzyl]-5-hydroxy-5-(4-methoxyphenyl)-5H-furan-2-one is obtained.

By analogous reaction with tolylsulfonyl chloride, starting from 3-(2,1,3-benzothiadiazol-5-yl)-4-(4-aminobenzyl)-5-hydroxy-5-(4-methophenyl)-5H-furan-2-one 3-(2,1,3-benzothiadiazol-5-yl)-4-[4-(tolylsulfonamido) benzyl]-5-hydroxy-5-(4-methoxyphenyl)-5H-furan-2-one is obtained.

EXAMPLE 11

By treatment of 0.25 g of 3-(2,1,3-benzothiadiazol-5-yl)-4-[4-(N-butylacetamido)benzyl]-5-hydroxy-5-(4-methoxyphenyl)-5H-furan-2-one in 20 ml of ethanol with 10 ml of KOH solution, after customary working up potassium 2-(2,1,3-benzothiadiazol-5-yl)-3-[4-(N-butyl-amino) benzyl]-4-(4-methoxyphenyl)-4-oxo-2-butenoate is obtained.

EXAMPLE 12

By reaction of equimolar amounts of 4,4'-dimethoxybenzil and ethyl 1-(2,1,3-benzothiadiazol-5-yl) acetate and an equimolar amount of sodium ethoxide in ethanol, after customary working up ethyl 2-(2,1,3-benzothiadiazol-5-yl)-3-(4-methoxyphenyl)-4-(4-methoxyphenyl)-4-oxo-2-butenoate is obtained.

By a subsequent ester hydrolysis using sodium hydroxide solution, sodium 2-(2,1,3-benzothiadiazol-5-yl)-3-(4-methoxyphenyl)-4-(4-methoxyphenyl)-4-oxo-2-butenoate is obtained.

EXAMPLE 13

Analogously to Example 1, by reaction of ethyl 2-(2,1,3-benzothiadiazole-6-methoxy-5-yl)-4-(1,4-benzodioxan-6-yl)-4-oxobutanoate [sic] with cyclohexane carbaldehyde 3-(2,1,3-benzothiadiazole-6-methoxy-5-yl)-4-cyclohexylmethyl-5-hydroxy-5-(1,4-benzodioxan-6-yl)-5H-furan-2-one [sic] is obtained.

By treatment with sodium hydroxide solution analogously to Example 2, sodium 2-(2,1,3-benzothiadiazole-6-methoxy-5-yl)-3-(cyclohexylmethyl)-4-(1,4-benzodioxan-6-yl)-4-oxo-2-butenoate [sic] is obtained therefrom.

EXAMPLE 14

The following are obtained analogously to Example 1 by reaction
of ethyl 2-(2,1,3-benzothiadiazol-5-yl)-4-(3-fluoro-4-methoxyphenyl)-4-oxobutanoate ("D") with benzaldehyde 3-(2,1,3-benzothiadiazol-5-yl)-4-benzyl-5-hydroxy-5-(3-fluoro-4-methoxyphenyl)-5H-furan-2-one, m.p. 65°
of "D" with 3,4,5-trimethoxybenzaldehyde ("E")

3-(2,1,3-benzothiadiazol-5-yl)-4-(3,4,5-trimethoxybenzyl)-5-hydroxy-5-(3-fluoro-4-methoxyphenyl)-5H-furan-2-one, FAB 539 and therefrom analogously to Example 2 sodium 2-(2,1,3-benzothiadiazol-5-yl)-3-(3,4,5-trimethoxybenzyl)-4-(3-fluoro-4-methoxyphenyl)-4-oxo-2-butenoate, m.p. 254° (decomposition)
of "A" with (7-methoxy-1,3-benzodioxol-5-yl)carbaldehyde 3-(2,1,3-benzothiadiazol-5-yl)-4-[(7-methoxy-1,3-benzodioxol-5-yl)methyl]-5-hydroxy-5-(4-methoxyphenyl)-5H-furan-2-one, m.p. 61°
of ethyl 2-(2,1,3-benzothiadiazol-5-yl)-4-(3-methoxyphenyl)-4-oxobutanoate with "B"

3-(2,1,3-benzothiadiazol-5-yl)-4-(3,4,5-trimethoxybenzyl)-5-hydroxy-5-(3-methoxphenyl)-5H-furan-2-one, m.p. 61° of ethyl 2-(2,1,3-benzothiadiazol-5-yl)-4-(2-methoxyphenyl)-4-oxobutanoate with "E"
3-(2,1,3-benzothiadiazol-5-yl)-4-(3,4,5-trimethoxybenzyl)-5-hydroxy-5-(2-methoxyphenyl)-5H-furan-2-one, m.p. 180°
of "A" with 4-methylthiobenzaldehyde
3-(2,1,3-benzothiadiazol-5-yl)-4-(4-methylthiobenzyl-5-hydroxy-5-(4-methoxyphenyl)-5H-furan-2-one, m.p. 64°
of "A" with 3-benzyloxy-4-methoxybenzaldehy [sic]
3-(2,1,3-benzothiadiazol-5-yl)-4-(3-benzyloxy-4-methoxybenzyl)-5-hydroxy-5-(4-methoxyphenyl)-5H-furan-2-one, m.p. 58°
of "A" with (2,3-dihydrobe nzofuran-5-yl)carbaldehyde
3-(2,1,3-benzothiadiazol-5-yl)-4-(2,3-dihydrobenzofuran-5-ylmethyl)-5-hydroxy-5-(4-methoxyphenyl)-5H-furan-2-one, m.p. 74°
of "A" with isobutyraldehyde
3-(2,1,3-benzothiadiazol-5-yl)-4-(2-methylpropyl)-5-hydroxy-5-(4-methoxyphenyl)-5H-furan-2-one, m.p. 129°
of "A" with 3,5-dimethoxybenzaldehyde
3-(2,1,3-benzothiadiazol-5-yl)-4-(3,5-dimethoxybenzyl)-5-hydroxy-5-(4-methoxyphenyl)-5H-furan-2-one, m.p. 54°
of "A" with 4-tert-butoxybenzaldehyde
3-(2,1,3-benzothiadiazol-5-yl)-4-(4-tert-butoxybenzyl)-5-hydroxy-5-(4-methoxyphenyl)-5H-furan-2-one, m.p. 68° and therefrom by reaction with TFA
3-(2,1,3-benzothiadiazol-5-yl)-4-(4-hydroxybenzyl)-5-hydroxy-5-(4-methoxyphenyl)-5H-furan-2-one, m.p . 83°
of "A" with 4-trifluoromethoxybenzaldehyde
3-(2,1,3-benzothiadiazol-5-yl)-4-(4-trifluoromethoxybenzyl)-5-hydroxy-5-(4-methoxyphenyl)-5H-furan-2-one, m.p. 56°
of "A" with 3,5-dimethoxy-4-isoprop oxybenzaldehyde
3-(2,1,3-benzothiadiazol-5-yl)-4-(3,5-dimethoxy-4-isopropoxybenzyl)-5-hydroxy-5-(4-methoxyphenyl)-5H-furan-2-one, m.p. 62°
of "A" with 3,5-dimethoxy-4-pentyloxybenzaldehyde
3-(2,1,3-benzothiadiazol-5-yl)-4-(3,5-dimethoxy-4-pentyloxybenzyl)-5-hydroxy-5-(4-methoxyphenyl)-5H-furan-2-one, FAB 576
of "A" with 3,5-dimethoxy-4-hexyloxybenzaldehyde
3-(2,1,3-benzothiadiazol-5-yl)-4-(3,5-dimethoxy-4-hexyloxybenzyl)-5-hydroxy-5-(4-methoxyphenyl)-5H-furan-2-one, FAB 590
of "A" with 4-phenoxybenzaldehyde
3-(2,1,3-benzothiadiazol-5-yl)-4-(4-phenoxybenzyl)-5-hydroxy-5-(4-methoxyphenyl)-5H-furan-2-one, rnp. 70°
of "A" with 4,5-dimethoxy-3-isopropoxybenzaldehyde
3-(2,1,3-benzothiadiazol-5-yl)-4-(4,5-dimethoxy-3-isopropoxybenzyl)-5-hydroxy-5-(4-methoxyphenyl)-5H-furan-2-one, EI 548
of ethyl 2-(2,1,3-benzothiadiazol-5-yl)-4-(2,5-dimethoxphenyl)-4-oxobutan sote with "E"
3-(2,1,3-benzothiadiazol-5-yl)-4-(3,4,5-trimethoxybenzyl)-5-hydroxy-5-(2,5-dimethoxyphenyl)-5H-furan-2-one, m.p. 73°
of ethyl 2-(2,1,3-benzothiadiazol-5-yl)-4-(3-chloro-4-methoxyphenyl)-4-oxobutanoate with "E"
3-(2,1,3-benzothiadiazol-5-yl)-4-(3,4,5-trimethoxybenzyl)-5-hydroxy-5-(3-chloro-4-methoxyphenyl)-5H-furan-2-one, m.p. 158° of ethyl 2-(2,1,3-benzothiadiazol-5-yl)-4-(3-methyl-4-mathoxyphenyl)-4-oxobutanoate with "E"

3-(2,1,3-benzothiadiazol-5-yl)-4-(3,4,5-trimethoxybenzyl)-5-hydroxy-5-(3-methyl-4-methoxyphenyl)-5H-furan-2-one, m.p. 80° of ethyl 2-(2,1,3-benzothiadiazol-5-yl)-4-(2,5-dimethoxyphenyl)-4-oxobutanoate with 3,4-diisopropoxy-5-methoxybenzaldehyde 3-(2,1,3-benzothiadiazol-5-yl)-4-(3,4-diisopropoxy-5-methoxybenzyl)-5-hydroxy-5-(2,5-dimethoxyphenyl)-5H-furan-2-one, m.p 70° of ethyl 2-(2,1,3-benzothiadiazol-5-yl)-4-(2,3-dihydrobenzofuran-5-yl)-4-oxobutanoate with "E"

3-(2,1,3-benzothiadiazol-5-yl)-4-(3,4,5-trimethoxybenzyl)-5-hydroxy-5-(2,3-dihydrobenzofuran-5-yl)-5H-furan-2-one, EI 532 of ethyl 2-(2,1,3-benzothiadiazol-5-yl)-4-(3-fluoro-4-methoxyphenyl)-4-oxobutanoate with 3,5-dimethoxy-4-isopropoxybenzaldehyde 3-(2,1,3-benzothiadiazol-5-yl)-4-(3,5-dimethoxy-4-isopropoxybenzyl)-5-hydroxy-5-(3-fluoro-4-methoxyphenyl)-5H-furan-2-one, EI 566 of "A" with 3,4-dimethoxy-5-propoxybenzaldehyde 3-(2,1,3-benzothiadiazol-5-yl)-4-(3,4-dimethoxy-5-propoxybenzyl)-5-hydroxy-5-(4-methoxhenyl)-5H-furan-2-one, m.p. 70°

The compounds below are obtained analogously 3-(2,1,3-benzothiadiazol-5-yl)-4-(3,4-diisopropoxy-5-methoxybenzyl)-5-hydroxy-5-(4-propoxyphenyl)-5H-furan-2-one. m.p. 150°

3-(2,1,3-benzothiadiazol-5-yl)-4-(3,4-diisopropoxy-5-methoxybenzyl)-5-hydroxy-5-(2,4-dimethoxyphenyl)-5H-furan-2-one, m.p. 164°

3-(2,1,3-benzothiadiazol-5-yl)-4-(4-benzyloxy-2-methoxybenzyl)-5-hydroxy-5-(4-methoxyphenyl)-5H-furan-2-one, EI 566

3-(2,1,3-benzothiadiazol-5-yl)-4-(2,3,4-trimethoxybenzyl)-5-hydroxy-5-(4-methoxyphenyl)-5H-furan-2-one, m.p. 70°

3-(2,1,3-benzothiadiazol-5-yl)-4-(3,4,5-trimethoxybenzyl)-5-hydroxy-5-(2,4-dimethoxyphenyl)-5H-furan-2-one, m.p. 70°

3-(2,1,3-benzothiadiazol-5-yl)-4-(3,4,5-triethoxybenzyl)-5-hydroxy-5-(4-methoxyphenyl)-5H-furan-2-one, m.p. 139°

3-(2,1,3-benzothiadiazol-5-yl)-4-(3,4,5-trimethoxybenzyl)-5-hydroxy-5-(4-difluoromethoxyphenyl)-5H-furan-2-one, FAB 557

3-(2,1,3-benzothiadiazol-5-yl)-4-(3-hydroxy-4-methoxybenzyl)-5-hydroxy-5-(4-methoxyphenyl)-5H-furan-2-one, FAB 477

3-(2,1,3-benzothiadiazol-5-yl)-4-(2,4-dimethoxybenzyl)-5-hydroxy-5-(4-methoxyphenyl)-5H-furan-2-one, EI 490

3-(2,1,3-benzothiadiazol-5-yl)-4-(2,4,5-trimethoxybenzyl)-5-hydroxy-5-(4-methoxyphenyl)-5H-furan-2-one, m.p 70°

3-(2,1,3-benzothiadiazol-5-yl)-4-(3,4,5-trimethoxybenzyl)-5-hydroxy-5-(3-fluoro-4-isopropoxyphenyl)-5H-furan-2-one, FAB 567

3-(2,1,3-benzothiadiazol-5-yl)-4-(3,4,5-trimethoxybenzyl)-5-hydroxy-5-(3-fluoro-4-propoxyphenyl)-5H-furan-2-one, FAB 567

3-(2,1,3-benzothiadiazol-6-methyl-5-yl)-4-(3,5-dimethoxy-4-isopropoxy benzyl)-5-hydroxy-5-(4-methoxyphenyl)-5H-furan-2-one, m.p 74°

3-(2,1,3-benzothiadiazol-5-yl)-4-(3,4,5-dimethoxy-4-benzyloxybenzyl)-5-hydroxy-5-(4-methoxyphenyl)-5H-furan-2-one, m.p. 61° and therefrom by reaction with trifluoroacetic acid/thioanisole 3-(2,1,3-benzothiadiazol-5-yl)-4-(3,5-dimethoxy-4-hydroxybenzyl)-5-hydroxy-5-(4-methoxyphenyl)-5H-furan-2-one, m.p. 69°

3-(2,1,3-benzothiadiazol-5-yl)-4-(3,5-dimethoxy-4-propoxybenzyl)-5-hydroxy-5-(4-methoxyphenyl)-5H-furan-2-one, m.p. 60°

3-(2,1,3-benzothiadiazol-5-yl)-4-(3,4-dimethoxy-5-isopropoxybenzyl)-5-hydroxy-5-(1,4-benzodioxan-6-yl)-5H-furan-2-one, FAB 577

3-(2,1,3-benzothiadiazol-6-methyl-5-yl)-4-(3,4,5-trimethoxybenzyl )-5-hydroxy-5-(4-methoxyphenyl)-5H-furan-2-one, m.p. 183°

3-(2,1,3-benzothiadiazol-5-yl)-4-(4-isopropoxybenzyl)-5-hydroxy-5-(4-methoxyphenyl)-5H-furan-2-one, FAB 489

3-(2,1,3-benzothiadiazol-5-yl)-4-(4-hexyloxybenzyl)-5-hydroxy-5-(4-methoxyphenyl)-5H-furan-2-one, FAB 531

3-(2,1,3-benzothiadiazol-5-yl)-4-(3,5-dimethoxy-4-isopropoxybenzyl)-5-hydroxy-5-(1,4-benzodioxan-6-yl)-5H-furan-2-one, m.p. 145°

3-(2,1,3-benzothiadiazol-5-yl)-4-(3-methoxy-5-butoxybenzyl)-5-hydroxy-5-(4-methoxyphenyl)-5H-furan-2-one, FAB 533

3-(2,1,3-benzothiadiazol-5-yl)-4-(3,4-diisopropoxybenzyl)-5-hydroxy-5-(4-methoxyphenyl)-5H-furan-2-one, m.p. 52°

3-(2,1,3-benzothiadiazol-5-yl)-4-(3,4,5-trimethoxybenzyl)-5-hydroxy-5-(2-fluoro-4-methoxyphenyl)-5H-furan-2-one, FAB 539

3-(2,1,3-benzothiadiazol-5-yl)-4-(3,4-dimethoxy-5-isopropoxybenzyl)-5-hydroxy-5-(3-fluoro-4-methoxyphenyl)-5H-furan-2-one, m.p. 126°

3-(2,1,3-benzothiadiazol-5-yl)-4-(3,4-dimethoxy-5-benzyloxybenzyl)-5-hydroxy-5-(4-methoxyphenyl)-5H-furan-2-one, FAB 597

3-(2,1,3-benzothiadiazol-5-yl)-4-(3,4,5-trimethoxybenzyl)-5-hydroxy-5-(4-fluoro-2-methoxyphenyl)-5H-furan-2-one, FAB 539

3-(2,1,3-benzothiadiazol-5-yl)-4-(3,5-dimethoxy-5-ethoxybenzyl)-5-hydroxy-5-(4-methoxyphenyl)-5H-furan-2-one, m.p. 123°

3-(2,1,3-benzothiadiazol-5-yl)-4-(4-methoxycarbonylbenzyl)-5-hydroxy-5-(4-methoxyphenyl)-5H-furan-2-one, m.p. 71°

3-(2,1,3-benzothiadiazol-5-yl)-4-(3,4-diisopropoxybenzyl)-5-hydroxy-5-(3-fluoro-4-methoxyphenyl)-5H-furan-2-one, FAB 565

3-(2,1,3-benzothiadiazol-5-yl)-4-(3,4,5-trimethoxybenzyl)-5-hydroxy-5-(4-benzyloxyphenyl)-5H-furan-2-one, FAB 489

3-(2,1,3-benzothiadiazol-4-methyl-5-yl)-4-(3,4,5-trimethoxybenzyl)-5-hydroxy-5-(4-methoxyphenyl)-5H-furan-2-one, m.p. 168

3-(2,1,3-benzothiadiazol-5-yl)-4-(3,5-dimethoxy-4-isobutoxybenzyl)-5-hydroxy-5-(4-methoxyphenyl)-5H-furan-2-one, m.p. 154° and [sic]

EXAMPLE 15

The following is obtained analogously to Example 4 by reaction of "C" g with ethyl 2-(7-methoxy-1,3-benzodioxol- 5-yl)-4-(4-methoxyphenyl)-4-oxobutanoate-4-(2,1,3-benzothiadiazol-5-yl)-3-(7-methoxy-1,3-benzodioxol-5-yl)-5-hydroxy-5-(4-methoxyphenyl)-5H-furan-2-one, m.p. 191°.

EXAMPLE 16

The following are obtained analogously to Example 2 from 3-(2,1,3-benzothiadiazol-5-yl)-4-(3,4-diisoropoxy-5-methoxybenzyl)-5-hydroxy-5-(3-fluoro-4-ethoxyphenyl)-5furan-2-one sodium $_2$-(2,1,3-benzothiadiazol-5-yl)-3-(3,4-diisopropoxy-5-methoxybenzyl)-4-(3-fluoro-4-methoxyphenyl)-4-oxo-2-butenoate, FAB 617 from 3-(2,1,3-benzothiadiazol-5-yl)-4-(3,5-dimethoxy-4-isopropoxybenzyl)-5-hydroxy-5-(4-methoxyphenyl)-5H-furan-2-one sodium 2-(2,1,3-benzothiadiazol-5-yl)-3-(3,5-dimethoxy-4-isopropoxybenzyl)-4-(4-methoxyphenyl)-4-oxo-2-butenoate, m.p. 65°.

The compounds below are obtained analogously sodium $_2$-(2,1,3-benzothiadiazol-5-yl)-3-(3,4-dimethoxy-5-isopropoxybenzyl)-4-(4-methoxyphenyl)-4-oxo-2-butenoate, m.p. 57° and sodium 2-(2,1,3-benzothiadiazol-5-yl)-3-(3,5-dimethoxy-4-isopropoxybenzyl)-4-(3-fluoro-4-methoxyphenyl)-4-oxo-2-butenoate, FAB 589.

The following is obtained analogously by treatment with KOH potassium 2-(2,1,3-benzothiadiazol-5-yl)-3-(3,4,5-trimethoxybenzyl)-4-(4-methoxyphenyl)-4-oxo-2-butenoate, m.p. 202°

The following examples relate to pharmaceutical preparations:

EXAMPLE A: Injection Vial

A solution of 100 g of an active compound of the formula I and 5 g of disodium hydrogen phosphate is adjusted to pH 6.5 in 3 l of double-distilled water using 2 N hydrochloric acid, sterile filtered, dispensed into injection vials, lyophilized under sterile conditions and aseptically sealed. Each injection vial contains 5 mg of active compound.

EXAMPLE B: Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE C: Solution

A solution of 1 g of an active compound of the formula I, 9.38 g of $NaH_2PO_4.2 H_2O$, 28.48 g of $Na_2HPO_4.12 H_2O$ and 0.1 g of benzalkonium chloride in 940 ml of double-distilled water is prepared. The solution is adjusted to pH 6.8, made up to 1 l and sterilized by irradiation. This solution can be used in the form of eye drops.

EXAMPLE D: Ointment 500 mg of an active compound of the formula I is mixed with 99.5 g of petroleum jelly under aseptic conditions.

EXAMPLE E: Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

EXAMPLE F: Coated Tablets.

Analogously to Example E, tablets are pressed which are then coated in a customary manner with a coating of sucrose, potato starch, talc, traganth and colourant.

EXAMPLE G: Capsules 2 kg of active compound of the formula I are filled into hard gelatine capsules in the customary manner such that each capsule contains 20 mg of the active compound.

EXAMPLE H: Ampoulos

A solution of 1 kg of active compound of the formula I in 60 l of double-distilled water is sterile filtered, dispensed into ampoules, lyophilized under sterile conditions and aseptically sealed. Each ampoule contains 10 mg of active compound.

We claim:
1. A compound of formula I

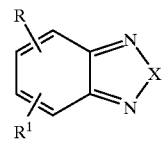

in which
R is

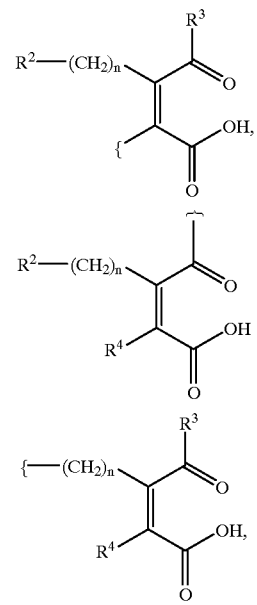

X is O or S,
$R^1$ is H, Hal, OH, OA, A, alkylene-O-A, $NO_2$, $NH_2$, NHacyl, $SO_2NH_2$, $SO_3$-A, $SO_2NHA$, CN or formyl,
$R^2,R^3,R^4$ in each case independently of one another are a phenyl group which is unsubstituted or mono- or polysubstituted by Hal, OH, OA, O-alkylene-$R^5$, A, S-A, S-OA, $SO_2A$, S-$OR^5$, $SO_2R^5$, $NO_2$, $NH_2$, NHA, NA$_2$, NHacyl, NHSO$_2$A, NHSO$_Z$R$^5$, NASO$_2$A, NASO$_2$-R$^5$, NH(CO)NH$_2$, NH(CO)NHA, formyl, NH(CO)NHR$^5$, NHCOOA, NAacyl, NHCOOCH$_2$R$^5$, NHSO$_2$CH$_2$R$^5$, NHCOO-alkylene-OA, NH(CO)NA$_2$, 1-piperidinyl-CO—NH, 1-pyrrolidinyl-CONH, O(CH$_2$)$_n$COOA, O(CH$_2$)$_n$COOH, O(CH$_2$)$_n$OH, O(CH$_2$)$_n$OA, CH$_2$OH, CH$_2$OA, COOH, COOA, CH$_2$COOH or CH$_2$COOA,

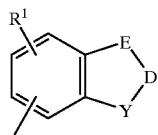

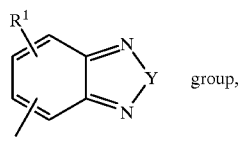 group, where
R$^2$ is additionally A or cycloalkyl,
R$^5$ is a phenyl group which is unsubstituted or mono- or polysubstituted by Hal, OH, OA, A, S-A, NO$_2$, NH$_2$, NHA, NA$_2$, NHacyl, NHSO$_2$A, NASO$_2$A, NH(CO)NH$_2$, NH(CO)NHA, formyl, NHCOOA, NAacyl, NHCOO-alkylene-OA, NH(CO)NA$_2$, N-piperidinyl-CO-NH, N-pyrrolidinyl-CONH, O(CH$_2$)$_n$COOA, O(CH$_2$)$_n$COOH, O(CH$_2$)$_n$OH, O(CH$_2$)$_n$OA, CH$_2$OH CH$_2$OA, COOH, COOA, CH$_2$COOH or CH$_2$COOA,
A is alkyl having 1–6 C atoms, in which one or two CH$_2$ groups can be replaced by O or S atoms or by —CR$^6$=CR$^{6'}$ groups and/or 1–7 H atoms can be replaced by F,
D is carbonyl or [C(R$^6$R$^{6'}$)]$_m$,
E is CH$_2$, S or O,
Y is O or S,
R$^6$ and R$^6$ in each case independently of one another are H, F or A,
Hal is fluorine, chlorine, bromine or iodine,
n is 0, 1 or 2 and
m is 1 or 2,
or a tautomeric ring-closed form,
or a pharmaceutically acceptable salt thereof.
2.
a) 2-(2,1,3-Benzothiadiazol-5-yl)-3-(3,4,5-trimethoxybenzyl)-4-(4-methoxyphenyl)-4-oxo-2-butenoic acid;
b) 2-(2,1,3-benzothiadiazol-5-yl)-3-(3,4,5-trimethoxybenzyl)-4-(3-fluoro-4-methoxyphenyl)-4-oxo-2-butenoic acid;
c) 3-(2,1,3-benzothiadiazol-5-yl)-4-(3,4,5-trimethoxybenzyl)-5-hydroxy-5-(4-methoxyphenyl)-5H-furan-2-one;
d) 3-(2,1,3-benzothiadiazol-5-yl)-4-(3,4,5-trimethoxybenzyl)-5-hydroxy-5-(3-fluoro-4-methoxyphenyl)-5H-furan-2-one;
e) 2-(2,1,3-benzothiadiazol-5-yl)-3-benzyl-4-(1,4-benzodioxan-6-yl)-4-oxo-2-butenoic acid;
f) 2-(2,1,3-benzothiadiazol-5-yl)-3-benzyl-4-(3-fluoro-4-methoxyphenyl)-4-oxo-2-butenoic acid;
g) 2-(2,1,3-benzothiadiazol-5-yl)-3-cyclohexylmethyl-4-(3-fluoro-4-methoxyphenyl)-4-oxo-2-butenoic acid;
h) 2-(2,1,3-benzothiadiazol-5-yl)-3-[3-(N,N-dimethylamino)benzyl]-4-(4-methoxyphenyl )-4-oxo-2-butenoic acid;

or a pharmaceutically acceptable salt thereof, according to claim 1.

3. A proces for the preparation of a compound of formula I according to claim 1, in which a) R is

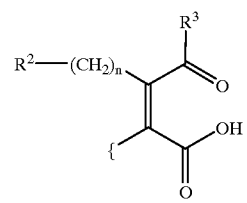

comprising reacting a compound of formula II

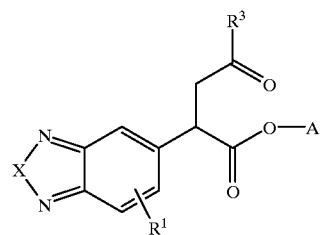 II in which

R$^1$, R$^3$ and X have the meaning indicated in claim 1, and A is alkyl having 1–4 C atoms or benzyl, with a compound of formula III R$^2$—(CH$_2$)$_k$—CHO     III in which
R$^2$ has the meaning indicated in claim 1 and
k is 0 or 1, and then cleaving the ester, or in which

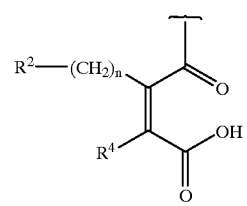

b) R is
comprising reacting a compound of formula IV

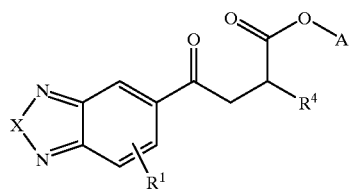

in which
R$^1$,R$^4$ and X have the meaning indicated in claim 1, and
A is alkyl having 1–4 C atoms or benzyl,
with a compound of formula III, as indicated,
and then cleaving the ester, or in which c) R is

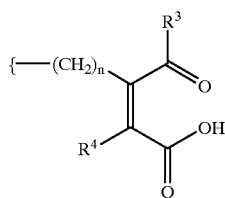

comprising reacting a compound of formula V

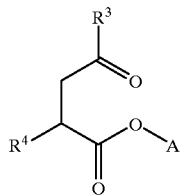

in which
R$^3$ and R$^4$ have the meaning indicated in claim 1, and
A is alkyl having 1–4 C atoms or benzyl,
with a compound of formula VI,

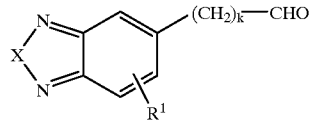

in which
R$^1$ and X have the meanings indicated in claim 1,
and k is 0 or 1,
and then cleaving the ester, and/or converting in a compound of formula I one or more radicals R$^1$, R$^2$, R$^3$ and/or R$^4$ into one or more radicals R$^1$, R$^2$, R$^3$ and/or R$^4$, comprising
   i) reducing a nitro group to an amino group,
   ii) acylating or alkylating an amino group, or
   iii) converting an amino group into a sulfonamido group,
and/or converting a base or acid of formula I into one of its salts.

4. A process for the production of a pharmaceutical composition, comprising combining into a suitable dose form a compound of claim 1 and at least one solid, liquid or semiliquid pharmaceutically acceptable excipient or auxiliary.

5. A pharmaceutical composition, comprising at least one compound of claim 1 and a pharmaceutically acceptable carrier.

6. A pharmaceutical composition for the control of hypertension, cardiac insufficiency, renal insufficiency, cerebral infarct, coronary heart disease, renal, cerebral or myocardial ischaemia, subarachnoid haemorrhage, inflammations, asthma or endotoxic shock, comprising a compund of claim 1 and a pharmaceutically acceptable carrier.

7. A method to treat hypertension, cardiac insufficiency, renal insufficiency, cerebral infarct, coronary heart disease, renal, cerebral or myocardial ischaemia, subarachnoid haemorrhage, inflammations, asthma or endotoxic shock, comprising administering to a patient in need thereof an effective dose of a compound of claim 1.

8. A compound of claim 1, in which alkylene is $C_{1-6}$, cycloalkyl is $C_{3-6}$, and acyl is $C_{1-6}$ alkanoyl.

9. A compound of claim 8, which is in the form of an (E) isomer.

10. A compound of claim 8, which is in the form of a (Z) isomer.

11. A compound of claim 8, wherein A is alkyl having 1–4 C atoms.

12. A compound of claim 8, wherein A is methyl.

13. A compound of claim 8, wherein alkylene is methylene, ethylene, propylene or butylene.

14. A compound of claim 8, wherein acyl is formyl, acetyl or propionyl.

15. A compound of claim 8, wherein E is O.

16. A compound of claim 8, wherein D is $CH_2$ or carbonyl.

17. A compound of claim 8, wherein Hal is F, Cl or Br.

18. A compound of claim 8, wherein R$^2$, R$^3$ or R$^4$ is phenyl which is monosubstituted.

19. A compound of claim 8, wherein R$^5$ is phenyl which is monosubstituted.

20. The method of claim 7, wherein the disease treated is hypertension or cardiac insufficiency.

21. A method of antagonizing an endothelin receptor in a patent, comprising administering to said patient a compound of claim 1 and a pharmaceutically acceptable carrier.

* * * * *